United States Patent
Rwei et al.

(10) Patent No.: US 11,344,498 B2
(45) Date of Patent: May 31, 2022

(54) COMPOSITIONS AND METHODS FOR ON-DEMAND HIGH-EFFICIENCY TRIGGERABLE ANESTHESIA

(71) Applicant: The Children's Medical Center Corporation, Boston, MA (US)

(72) Inventors: Alina Y. Rwei, Brighton, MA (US); Changyou Zhan, Jamaica Plain, MA (US); Kathleen J. Cullion, Boston, MA (US); Daniel S. Kohane, Newton, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 192 days.

(21) Appl. No.: 15/767,116

(22) PCT Filed: Oct. 7, 2016

(86) PCT No.: PCT/US2016/056139
§ 371 (c)(1),
(2) Date: Apr. 9, 2018

(87) PCT Pub. No.: WO2017/062875
PCT Pub. Date: Apr. 13, 2017

(65) Prior Publication Data
US 2019/0070115 A1    Mar. 7, 2019

Related U.S. Application Data

(60) Provisional application No. 62/329,721, filed on Apr. 29, 2016, provisional application No. 62/239,164, filed on Oct. 8, 2015.

(51) Int. Cl.
*A61P 23/02* (2006.01)
*A61K 9/127* (2006.01)
*A61K 9/14* (2006.01)
*A61K 41/00* (2020.01)
*A61K 31/4174* (2006.01)
*A61K 31/445* (2006.01)
*A61K 9/00* (2006.01)
*A61K 31/519* (2006.01)
*A61K 45/06* (2006.01)

(52) U.S. Cl.
CPC .......... *A61K 9/1278* (2013.01); *A61K 9/0019* (2013.01); *A61K 31/4174* (2013.01); *A61K 31/445* (2013.01); *A61K 31/519* (2013.01); *A61K 41/0028* (2013.01); *A61K 45/06* (2013.01); *A61P 23/02* (2018.01)

(58) Field of Classification Search
None
See application file for complete search history.

(56) References Cited

U.S. PATENT DOCUMENTS

| | | | |
|---|---|---|---|
| 7,063,860 B2 | 6/2006 | Chancellor | |
| 8,110,217 B2 | 2/2012 | Chancellor | |
| 8,658,699 B2 | 2/2014 | Kohane | |
| 8,975,268 B2 | 3/2015 | Berde | |
| 8,975,281 B2 | 3/2015 | Berde | |
| 2005/0202093 A1* | 9/2005 | Kohane | A61K 9/0085 424/489 |
| 2011/0212027 A1 | 9/2011 | Hoare | |
| 2011/0230568 A1 | 9/2011 | Hoare | |
| 2013/0156706 A1* | 6/2013 | Bettinger | A61K 49/222 424/9.52 |

FOREIGN PATENT DOCUMENTS

WO    2011075557    6/2011

OTHER PUBLICATIONS

Shibaguchi, Hirotomo, et al. "Sonodynamic cancer therapy: a non-invasive and repeatable approach using low-intensity ultrasound with a sonosensitizer." Anticancer research 31.7 (2011): 2425-2429. (Year: 2011).*
Kneidl, Barbara, et al. "Thermosensitive liposomal drug delivery systems: state of the art review." International journal of nanomedicine 9 (2014): 4387. (Year: 2014).*
Abreu, Ana S., et al. "Nanoliposomes for encapsulation and delivery of the potential antitumoral methyl 6-methoxy-3-(4-methoxyphenyl)-1 H-indole-2-carboxylate." Nanoscale research letters 6.1 (2011): 482. (Year: 2011).*
Adams, et al., "The local anesthetic activity of tetrodotoxin alone and in combination with vasoconstrictors and local anesthetics", Anesth Analg, 55(4):568-573 (1976).
Afonso, et al., "Dexmedetomidine: current role in anesthesia and intensive care", Revista Brasileira De Anestesiologia, 62(1):118-133 (2012).
Agarwal, et al., "Remote triggered release of doxorubicin in tumors by synergistic application of thermosensitive liposomes and gold nanorods", ACS Nano, 5(6), 4919-26 (2011).

(Continued)

*Primary Examiner* — Nissa M Westerberg
(74) *Attorney, Agent, or Firm* — Pabst Patent Group LLP

(57) ABSTRACT

Compositions and methods for administration of local anesthetics that are delivered by a single injection and enable repeated on-demand or high influx analgesia over extended periods have been developed. Pharmaceutical compositions including an effective amount of one or more sodium channel blockers including site 1 sodium channel blockers, optionally one or more alpha-2-adrenergic agonists, which are optionally encapsulated in liposomes, particles or microbubbles, and one or more triggerable elements are provided. The triggerable elements allow delivery of the encapsulated anesthetic drugs when an appropriate triggering stimuli are applied. Exemplary triggering agents or stimuli include near-infrared irradiation, UV- and visible light, ultrasound and magnetic field. In one embodiment, ultrasound is used to trigger a burst of microbubbles to enhance penetration of local anesthetic.

22 Claims, 20 Drawing Sheets

(56) References Cited

OTHER PUBLICATIONS

Akiyama, et al., "The effects of PEG grafting level and injection dose on gold nanorod biodistribution in the tumor-bearing mice", J Control Release., 139(1):81-84 (2009).
An, et al., "Dexamethasone as adjuvant to bupivacaine prolongs the duration of thermal antinociception and prevents bupivacaine-induced rebound hyperalgesia via regional mechanism in a mouse sciatic nerve block model", PLoS ONE, 10(4):e0123459, (2015).
Anderson, et al., "In vivo biocompatibility of implantable delivery systems and biomaterials", Eur. J. Pharm. Biopharm, 40(1), 1-8 (1994).
Barash, et al., "Prolonged duration local anesthesia with minimal toxicity", Proc. Natl. Acad. Sci., 106(17), 7125-30 (2009).
Bartlett, et al., "Phosphorus assay in column chromatography", J Biol Chem, 234(3):466-8(1959).
Benyamin, et al., "Opioid complications and side effects", Expert Rev. Neurother., 11(2 Suppl): S105-20 (2008).
Black, et al., "From molecular mechanochemistry to stress-responsive materials", J. Mater. Chem., 21:1655-1663 (2011).
Bligh et al., "A rapid method of total lipid extraction and purification", Can. J. Biochem. Physiol., 37(8):911-917 (1959).
Brantley, et al., "Polymer mechanochemistry: The design and study of mechanophores", Polymer International, 62 (1), 2-12 (2013).
Brigger et.al "Nanoparticles in cancer therapy and diagnosis", Adv Drug Deliv Rev 54, 631-651 (2002).
Brummett, et al., "Perineural administration of dexmedetomidine in combination with bupivacaine enhances sensory and motor blockade in sciatic nerve block without inducing neurotoxicity in rat", Anesthesiology, 109:502-511 (2008).
Brummett, et al., "Perineural dexmedetomidine added to ropivacaine causes a dose-dependent increase in the duration of thermal antinociception in sciatic nerve block in rat", Anesthesiology, 111:1111-1119(2009).
Brummett, et al., "Perineural dexmedetomidine added to ropivacaine for sciatic nerve block in rats prolongs the duration of analgesia by blocking the hyperpolarization-activated cation current", Anesthesiology, 115:836-843 (2011).
Carter, et al., "Porphyrin-phospholipid liposomes permeabilized by near-infrared light", Nature Communications, 5: 3546 (2014).
Caruso, et al., "Mechanically-induced chemical changes in polymeric materials", Chem. Rev., 109(11):5755-5798 (2009).
Castillo, et al., "Glucocorticoids prolong rat sciatic nerve blockade in vivo from bupivacaine microspheres", Anesthesiology, 85(5):1157-1166 (1996).
Catterall, "Neurotoxins that act on voltage-sensitive sodium channels in excitable membranes", Annu. Rev. Pharmacol. Toxicol., 20:15-43 (1980).
Chang, et al., "Clinically proven Liposome-Based drug delivery: formulation, characterization and therapeutic efficacy", Scientific Rep., 1,195 (2012).
Chau et al., "The chemical synthesis of tetrodoxin: an ongoing quest", Mar Drugs, 9(10): 2046-2074 (2011).
Chen, et al., "Injectable microparticle-gel system for prolonged and localized lidocaine release. II. In vivo anesthetic effects", J. Biomed. Mater. Res., 70(3):459-466 (2004).
Cintas, et al., "Enabling technologies built on a sonochemical platform: challenges and opportunities", Ultrason. Sonochem., 25:8-16 (2015).
Cohen, et al., "Prolonged analgesia from Bupisome and Bupigel formulations: from design and fabrication to improved stability", J. Controlled Release, 160(2):346-52 (2012).
Colombo, et al., "Prolonged duration local anesthesia with lipid-protein-sugar particles containing bupivacaine and dexamethasone", Mater. Res., Part A, 75(2):458-464 (2005).
Curley, et al., "Prolonged regional nerve blockade. Injectable biodegradable bupivacaine/polyester microspheres", Anesthesiology, 386 84(6):1401-10 (1996).
Dai, et al., "In vivo multimodality imaging and cancer therapy by near-infrared light-triggered trans-platinum pro-drug-conjugated upconverison nanoparticles", J. Am. Chem. Soc., 135(50):18920-18929 (2013).
Dubinsky, et al., "High-intensity focused ultrasound: current potential and oncologic applications", Am. J. Roentgenology., 190(1):191-199 (2008).
El-Sayed, "Some interesting properties of metals confined in time and nanometer space of different shapes", Acc. Chem. Res., 34(4):257-264 (2001).
Epstein-Barash, et al., "A microcomposite hydrogel for repeated on-demand ultrasound-triggered drug delivery", Biomaterials, 31(19):5208-17 (2010).
Epstein-Barash, et al., "Prolonged duration local anesthesia with minimal toxicity", Proc. Natl. Acad. Sci., 106(17):7125-30 (2009).
Ferrara, "Driving delivery vehicles with ultrasound", Adv. Drug Delivery Rev., 60(10):1097-1102 (2008).
Fleming, et al., "A synthesis of (+)-saxitoxin.", J. Am. Chem. Soc., 3926 (2006).
Fletcher, et al., "Influence of timing of administration on the analgesic effect of bupivacaine infiltration in carrageenin-injected rats", Anesthesiology, 84(5):1129-37 (1996).
Forkink, et al., "Detection and manipulation of mitochondrial reactive oxygen species in mammalian cells", Biochim. Biophys. Acta, Bioenerg., 1797:1034-1044 (2010).
Gabizon, et al., "Clinical studies of liposome-encapsulated doxorubicin", Acta Oncol., 33:779-786 (1994).
Goodwin, et al., "Synthetic micelle sensitive to IR light via a two-photon process", J.Am. Chem. Soc. 127, 9952-9953(2005).
Grant, et al., "Physical biochemistry of a liposomal amphotericin B mixture used for patient treatment", Biochem. Biophys. Acta, 984(1):11-20 (1989).
Gregoriadis, "Liposomes as carriers of drugs. Observations on vesicle fate after injection and its control", Subcell. Biochem., 14:363-378 (1989).
Gregoriadis, "Liposomes as carriers of enzymes or drugs: a new approach to the treatment of storage diseases", Biochem. J., 124(5):58P(1971).
Gregoriadis, et al., "Improving the therapeutic efficacy of peptides and proteins: a role for polysialic acids", Int. J. Pharm., 300:125-30 (2005).
Gregoridis, et al., "Liposomes in Gaucher type I disease: use in enzyme therapy and the creation of an animal model", Prog. Clin. Biol. Res., 95:681-701 (1982).
Hayes, et al., "Three-MHz Ultrasound Heats Deeper Into the Tissues Than Originally Theorized", Journal of Athletic Training, 39(3):230-234 (2004).
Helal, et al., "Effects of perineural administration of dexmedetomidine in combination with bupivacaine in a femoral-sciatic nerve block", Saudi Journal of Anaesthesia, 10(1):18-24(2016).
Henderson, et al., "Near-infrared photonic energy penetration: can infrared phototherapy effectively reach the human brain", Neuropsychiatr. Dis. Treat., 11:2191-2208 (2015).
Huang, et al., "Sinularin from indigenous soft coral attenuates nociceptive responses and spinal neuroinflammation in carrageenan-induced inflammatory rat model", Marine drugs, 10(9):1899-919 (2012).
Jacobi, et al., "Total synthesis of (.+<.)-saxitoxin", J. Am. Chem. Soc., 106 (19):5594-5598 (1984).
Jain, et al., "Calculated absorption and scattering properties of gold nanoparticles of different size, shape, and composition: applications in biological imaging and biomedicine", J. Phys. Chem. B, 110, 7238 (2006).
Kahn et al., "Amitriptyline for prolonged cutaneous analgesia in the rat", Anesthesiology, 96(1), 109-16 (2002).
Kao, "Tetrodotoxin, saxitoxin and their significance in the study of excitation phenomena", Pharm. Rev., 18(2):997-1049 (1966).
Kayser, et al., "Differential effects of various doses of morphine and naloxone on two nociceptive test thresholds in arthritic and normal rats", Pain, 41(3):353-63 (1990).
Kayser, et al., "The analgesic effects of morphine, but not those of the enkephalinase inhibitor thiorphan, are enhanced in arthritic rats", Brain Res, 267(1):131-8 (1983).

(56) References Cited

OTHER PUBLICATIONS

Kheirolomoom, et al., "Acoustically-active microbubbles conjugated to liposomes: characterization of a proposed drug delivery vehicle", J Control Release, 118(3):275-84 (2007).
Kim, et al., "Ultrasound Triggered Smart Drug Release from a Poly(dimethylsiloxane)-Mesoporous Silica Composite", Adv. Mater., 18:3083-3088 (2006).
Kishi, et al., "A stereospecific total synthesis of d,l-saxitoxin", J. Am. Chem. Soc., 99(8):2818 (1977).
Kissin, et al., "Effect of prolonged nerve block on inflammatory hyperalgesia in rats: prevention of late hyperalgesia", Anesthesiology, 88(1):224-32 (1998).
Kohane, et al., "Are-examination of Tetradotoxin for Prolonged Duration Local Anesthesiology", Anesthesiology, 89:119-131 (1998).
Kohane, et al., "Biocompatibility of lipid-protein-sugar particles containing bupivacaine in the epineurium", J. Biomed. Mater. Res., 59:450-459 (2002).
Kohane, et al., "Effects of adrenergic agonists and antagonists on tetrodotoxin-induced nerve block", Regional Anesthesia and Pain Medicine, 26(3):239-245 (2001).
Kohane, et al., "Prolonged duration local anesthesia from tetrodotoxin-enhanced local anesthetic microspheres", Pain, 379 104(1-2):415-421 (2003).
Kohane, et al., "Sciatic nerve blockade in infant, adolescent, and adult rats: a comparison of ropivacaine with bupivacaine", Anesthesiology, 89(5):1199-1208 (1998).
Kost, et al., "Ultrasound-enhanced polymer degradation and release of incorporated substances", Proc. Natl. Acad. Sci, 86(20):7663 (1989).
Kosugi, et al., "High concentrations of dexmedetomidine inhibit compound action potentials in frog sciatic nerves without alpha(2) adrenoceptor activation.", Br. J. Pharmacol., 160:1662-1676 (2010).
Lagos, "Microalgal blooms: a global issue with negative impact in Chile", N. Biol. Res., 31:375-386 (1998).
Lagos, et al., "The first evidence of paralytic shellfish toxins in the fresh water cyanobacterium *Cylindrospermopsis raciborskii*, isolated from Brazil",Toxicon, 37:1359-1373 (1999).
Lavand'Homme et al., "Perioperative administration of the alpha2-adrenoceptor agonist clonidine at the site of nerve injury reduces the development of mechanical hypersensitivity and modulates local cytokine expression", Pain, 105:247-254 (2003).
Lawson, et al., "Formation of Stable Nanocapsules from Polymerizable Phospholipids", Langmuir 19:6401-6407 (2003).
Lawson, et al., "Polymerization of Vesicles Composed of N-(4-Vinylbenzoyl)phosphatidylethanolamine", Langmuir, 19(8):3557-3560 (2003b).
Lentacker, et al., "Drug loaded microbubble design for ultrasound triggered delivery", Soft Matter, 5:2161 (2009).
Lichtenberg, "Liposomes: Preparation, Characterization, and Preservation", Methods Biochem. Anal., 33:337-362 (1988).
Lin, et al., "Ultrasound sensitive eLiposomes containing doxorubicin for drug targeting therapy", Nanomedicine, 10:67-76 (2014).
Link, et al., "Size and Temperature Dependence of the Plasmon Absorption of Colloidal Gold Nanoparticles", Int. Rev. Phys. Chem., 19:409 (2000).
Liu, et al., "Photoisomerisable cholesterol derivatives as photo-trigger of liposomes: Effect of lipid polarity, temperature, incorporation ratio, and cholesterol", Biochim. Biophys. Acta, 1720(1-2):28-34 (2005).
Love, et al., "Self-Assembled Monolayers of Thiolates on Metals as a Form of Nanotechnoloy", Chem. Rev., 105(4):1103-1170 (2005).
Liu, et al., "A matching algorithm in PMWL based on ClueTree", New Generation Computing, Springer International Publishing: New York; pp. 95-122 (2014).
Magde, et al., "Fluorescence quantum yields and their relation to lifetimes of rhodamine 6G and fluorescein in nine solvents: improved absolute standards for quantum yields", Photochem. Photobiol., 75(4):327-334 (2002).

Mallick, et al., "Liposomes: versatile and biocompatible nanovesicles for efficient biomolecules delivery", J. Nanosci. Nanotechnol., 14(1):755-65 (2014).
Marhofer, et al., "Fifteen years of ultrasound guidance in regional anaesthesia: Part 2-recent developments in block techniques", British Journal of Anaesthesia, 104:673-683 (2010).
Maruyama, et al., "Enhanced delivery of doxorubicin to tumor by long-circulating thermosensitive liposomes and local hyperthermia", Biochim. Biophys. Acta., 1149(2):209-16 (1993).
Masters, et al., "Prolonged regional nerve blockade by controlled release of local anesthetic from a biodegradable polymer matrix", Anesthesiology, 79:340-346 (1993).
McAlvin, et al., "Corneal Anesthesia With Site 1 Sodium Channel Blockers and Dexmedetomidine", Invest. Ophthalmol. Vis. Sci., 56(6):3820-3826 (2015).
McAlvin, et al., "Multivesicular liposomal bupivacaine at the sciatic nerve", Biomaterials, 35:4557-4564 (2014).
Nassar, et al., "Nociceptor-specific gene deletion reveals a major role for Nav1.7 (PN1) in acute and inflammatory pain", Proc Natl Acad Sci USA, 101:12706-12711 (2004).
Needham, et al., "Anew temperature-sensitive liposome for use with mild hyperthermia: characterization and testing in a human tumor xenograft model", Cancer Res, 60(5):1197-201 (2000).
Niidome, et al., "PEG-modified gold nanorods with a stealth character for in vivo applications", J Control Release, 114(3):343-347 (2006).
Niidome, et al., "Poly(ethylene glycol)-modified gold nanorods as a photothermal nanodevice for hyperthermia", J Biomater Sci Polym Ed., 20:1203-1215 (2009).
Nikoobakht, et al., "Preperation and Growth Mechanism of Gold Nanorods (NRs) Using seed-Mediatd Growth Method", M.A. Chem. Mater., 15:1957-1962 (2003).
Nishikawa, et al., "An efficient total synthesis of optically active tetrodotoxin", Angew. Chem. Int. Ed., 43(36):4782-4785 (2004).
Ogura, et al., "Low-frequency sonophoresis: current status and future prospects", Adv. Drug Delivery Rev., 60(10):1218-1223 (2008).
Ohya, et al., "Photo-sensitive lipid membrane perturbation by a single chain lipid having terminal spiropyran group", Supramol. Sci., 5(1-2):21-29 (1998).
Ohyabu, et al., "First asymmetric total synthesis of tetrodotoxin", J. Am. Chem. Soc., 125(29):8798-8805 (2003).
Owen, et al., "A phase I clinical evaluation of liposome-entrapped doxorubicin (Lip-Dox) in patients with primary and metastatic hepatic malignancy", Anticancer Drugs, 3:101-107 (1992).
Padera, et al., "Local myotoxicity from sustained release of bupivacaine from microparticles", Anesthesiology, 108(5):921-928 (2008).
Padera, et al., "Tetrodotoxin for prolonged local anesthesia with minimal myotoxicity", Muscle Nerve, 34(6):747-753 (2006).
Pereira, et al., "Paralytic shellfish toxins in the freshwater cyanobacterium *Aphanizomenon flos-aquae*, isolated from Montargil reservoir, Portugal", Toxicon, 38:1689-1702 (2000).
Pryor, et al., "Oxy-radicals and related species: their formation, lifetimes, and reactions", Annu. Rev. Physiol., 48:657-667 (1986).
Regen, et al., "Polymerized phosphatidyl choline vesicles. Stabilized and controllable time-release carriers", Biochem. Biophys. Res. Commun. 101:131-136 (1981).
Reimer, et al., "Povidone-Iodine Liposomes—An Overview", Dermatol., 195:93(1997).
Rodriguez-Navarro, "Potentiation of local anesthetic activity of neosaxitoxin with bupivacaine or epinephrine: development of a long-acting pain blocker", Neurotox. Res., 16:408-15 (2009).
Rodriguez-Navarro, et al., "Comparison of neosaxitoxin versus bupivacaine via port infiltration for postoperative analgesia following laparoscopic cholecystectomy: a randomized, double-blind trial", Reg. Anesth. Pain Med., 36(2):103-109 (2011).
Rodriguez-Navarro, et al., "Neosaxitoxin as a local anesthetic: preliminary observations from a first human trial.", Anesthesiology, 106:339-45 (2007).
Roots, et al., "Estimation of life times and diffusion distances of radicals involved in x-ray-induced DNA strand breaks of killing of mammalian cells", Radiat. Res., 64:306-320 (1975).

(56) References Cited

OTHER PUBLICATIONS

Rwei, et al., "Photoresponsive nanoparticles for drug delivery", Nano Today, 10:451-467 (2015a).
Rwei, et al., "Repeatable and adjustable on-demand sciatic nerve block with phototriggerable liposomes", Proc. Natl. Acad. Sci. USA, 112:15719-15724 (2015b).
Sapra, et al., "Ligand-targeted liposomes for cancer treatment", Curr. Drug Deliv., 2(4):369-381 (2005).
Schroeder, et al., "Ultrasound, liposomes, and drug delivery: principles for using ultrasound to control the release of drugs from liposomes", Chem. Phys. Lipids., 162(1-2):1-16 (2009).
Schwarz, et al., "The rate of action of tetrodotoxin on myelinated nerve fibres of Xenopus laevis and Rana esculenta", J. Physiol., 233(1):167-194 (1973).
Senior, "Fate and behavior of liposomes in vivo: a review of controlling factors", Crit. Rev. Ther. Drug Carrier Sys., 3, 123-193 (1987).
Shankarappa, et al., "Prolonged nerve blockade delays the onset of neuropathic pain", Proc. Natl. Acad. Sci., 109(43):17555-60 (2012).
Shi, "Graphene-based magnetic plasmonic nanocomposite for dual bioimaging and photothermal therapy", Biomaterials, 34:4786-4793 (2013).
Shi, et al., "Reactive Oxygen Species-Manipulated Drug Release from a Smart Envelope-Type Mesoporous Titanium Nanovehicle for Tumor Sonodynamic-Chemotherapy", ACS Appl. Mater. Interfaces, 7:28554-28565 (2015).
Shichor, et al., "Toxicogenomic analysis of a sustained release local anesthetic delivery system", Biomaterials, 33(13):3586-93 (2012).
Simons, et al., "Effect of chemical permeation enhancers on nerve blockade", Mol Pharm, 6(1):265-273 (2009).
Simpson, et al., "Near-infrared optical properties of ex vivo human skin and subcutaneous tissues measured using the Monte Carlo inversion techniqu", Phys. Med. Biol., 43:2465-2478 (1998).
Sirsi, et al., "Microbubble Compositions, Properties and Biomedical Applications", Bubble Sci. Eng. Technol., 1(1-2):3-17 (2009).
Skovsen, et al., "Lifetime and diffusion of singlet oxygen in a cell", J. Phys. Chem. B., 109:8570-8573 (2005).
Spence, "Activated photothermal heating using croconaine dyes", Chem. Sci., 4:4240-4244 (2013).
Suslick, et al., Annu. Rev. Mater. Sc., 105:2921 (1999).
Terlau, et al., "Mapping the site of block by tetrodotoxin and saxitoxin of sodium channel II", FEBS Lett., 293(1-2):93-6 (1991).
Thalhammer et al., "Neurologic evaluation of the rat during sciatic nerve block with lidocaine", Anesthesiology, 82(4):1013-1025 (1995).
Timko, et al., "Near-infrared-actuated devices for remotely controlled drug delivery", Proc. Natl. Acad. Sci., 111(4):1349-54 (2014b).
Timko, et al., "Prospects for near-infrared technology in remotely triggered drug delivery", Drug Delivery, 11(11):1681-5 (2014a).
Timko, et al., "Remotely triggerable drug delivery systems", Adv. Mater., 22(44):4925-43 (2010).
Troutman, et al., "Light-Induced Content Release from Plasmon Resonant Liposomes", Adv. Mater., 21(22):2334-2338 (2009).
Tufek, et al., "The protective effect of dexmedetomidine on bupivacaine-induced sciatic nerve inflammation is mediated by mast cells", Clin Invest Med, 36:E95-102 (2013).
Vankujik, "Effects of ultraviolet light on the eye: role of protective glasses", Environ. Health Perspect. 96:177-184 (1991).
Volodkin, et al., "Near-IR remote release from assemblies of liposomes and nanoparticles", Angew. Chem., Int. Ed., 48(10):1807-9 (2009).
Wang, et al., "Binding affinity and stereoselectivity of local anesthetics in single batrachotoxin-activated Na+ channels", J. Gen. Physiol., 96(5):1105-27 (1990).
Weissleder, "A clearer vision for in vivo imaging", Nat. Biotechnol., 19(4):316 (2001).
Wijaya, et al., "Ligand customization and DNA functionalization of gold nanorods via round-trip phase transfer ligand exchange", Langmuir, 24(18):9966-9999 (2008).
Wood, et al., "A review of low-intensity ultrasound for cancer therapy", Ultrasound Med. Biol., 41:905-928 (2015).
Wu, et al., "Driving delivery vehicles with ultrasound", Adv. Drug Delivery Rev., 60(10):1097-1102 (2008a).
Wu, et al., "Remotely triggered liposome release by near-infrared light absorption via hollow gold nanoshells", J. Am. Chem. Soc., 130 (26):8175-8177 (2008b).
Xia, et al., "Shape-controlled synthesis of metal nanocrystals: simple chemistry meets complex physics", Angew. Chem. Int. Ed., 48(1):60 (2009).
Yabuki, et al., "Locally injected dexmedetomidine induces vasoconstriction via peripheral $\alpha$-2A adrenoceptor subtype in guinea pigs", Reg. Anesth. Pain Med. , 39:133-136 (2014).
Yektas, et al., "The effects of 2 µg and 4 µg doses of dexmedetomidine in combination with intrathecal hyperbaric bupivacaine on spinal anesthesia and its postoperative analgesic characteristics", Pain Res Manag, 19(2):75-81 (2014).
Yoshitomi, et al., "Dexmedetomidine enhances the local anesthetic action of lidocaine via an alpha-2A adrenoceptor", Anesth. Analg., 107(1):96-101 (2008).
You, et al., "Near-infrared light triggers release of Paclitaxel from biodegradable microspheres: photothermal effect and enhanced antitumor activity", Small, 6(9):1022-1031 (2010).
Zhan, et al., "Phototriggered Local Anesthesia", Nano Lett, 16:177-181 (2016).
Zimmermann, et al., "Sensory neuron sodium channel Nav1.8 is essential for pain at low temperatures", Nature, 447:855-858 (2007).
International Search Report for PCT/US2016/056139, dated Jan. 4, 2017.
Ranade, "Drug delivery systems-2. Site specific drug delivery utilizing monoclonal antibodies", J. Clin. Pharmacol., 29:873-884 (1989).

\* cited by examiner

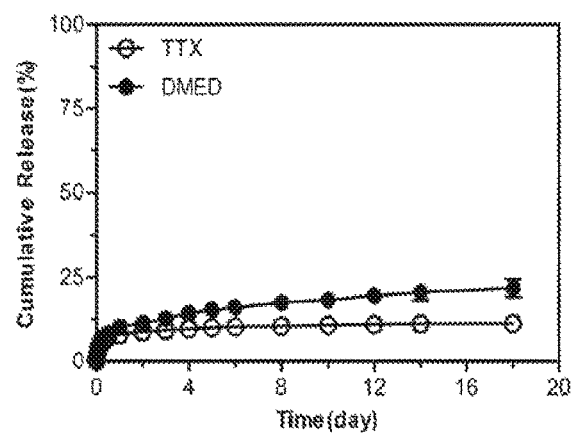
FIG. 5
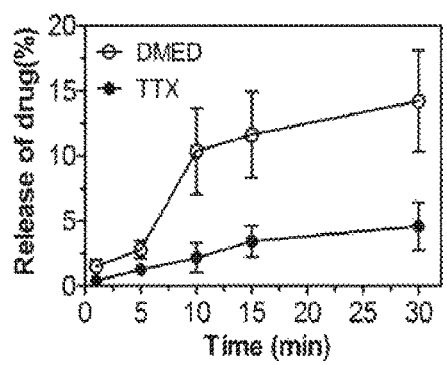 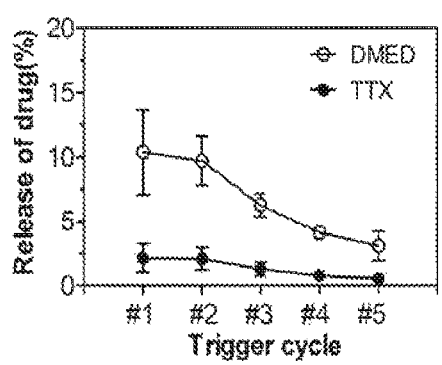
FIG. 6A FIG. 6B

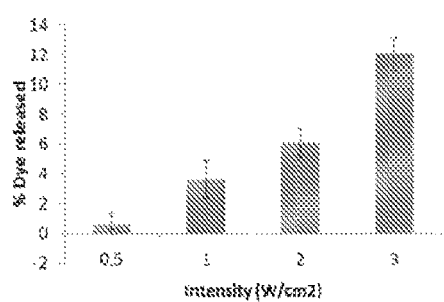
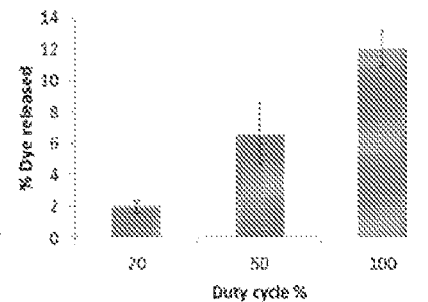
FIG. 23E        FIG. 23F
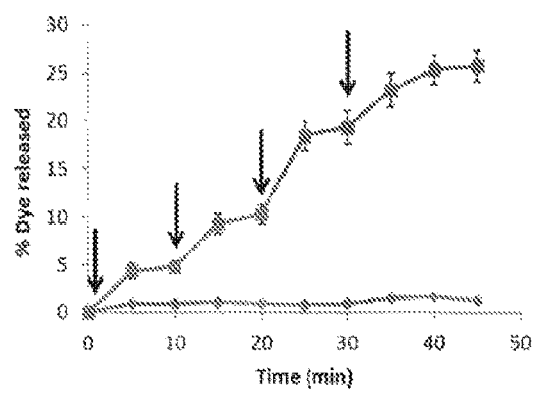
FIG. 24
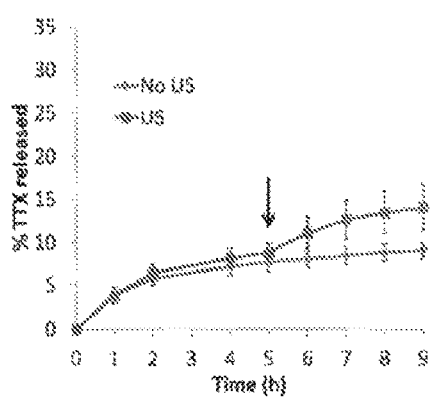
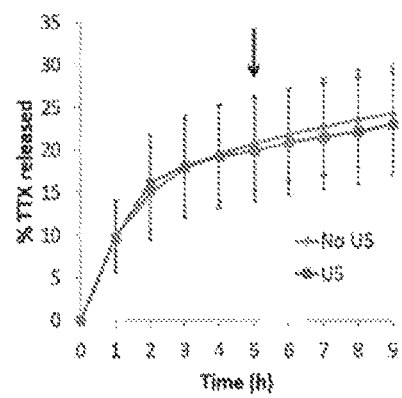
FIG. 25A        FIG. 25B

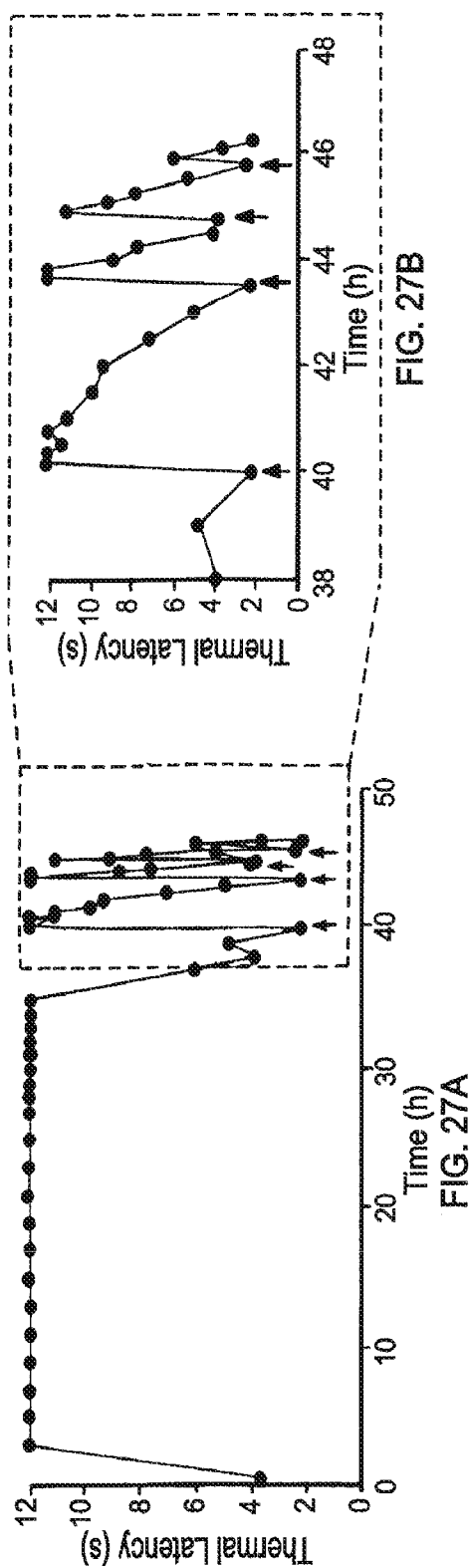

COMPOSITIONS AND METHODS FOR ON-DEMAND HIGH-EFFICIENCY TRIGGERABLE ANESTHESIA

CROSS-REFERENCE TO RELATED APPLICATIONS

This application is a National Phase application under 35 U.S.C. 371 of PCT/US2016/056139, filed Oct. 7, 2016, which claims priority to and benefit of U.S. Provisional Application No. 62/239,164, filed Oct. 8, 2015, and U.S. Provisional Application No. 62/329,721, filed Apr. 29, 2016, both of which are hereby incorporated herein by reference in their entireties.

STATEMENT REGARDING FEDERALLY SPONSORED RESEARCH

This invention was made with Government Support under grant numbers GM073626 and GM116920 awarded by the National Institutes of Health. The Government has certain rights in the invention.

FIELD OF THE INVENTION

The invention relates generally to methods and compositions for on-demand nerve blockade with local anesthetics, particularly molecular delivery systems for repeatable on-demand high-efficiency drug delivery triggered by irradiation or acoustic waves.

BACKGROUND OF THE INVENTION

The quality of life of patients suffering from postoperative or even chronic pain is often diminished by the need for repeated administration of systemic analgesic medications (e.g., opioids), which give rise to potentially serious complications (Benyamin, et al., *Expert Rev. Neurother.*, 11 (2 Suppl), S105-20 (2008)) and clouding of the sensorium. Typically, repeated administration of systemic analgesic medications requires that patients be tethered to an external device, which can prolong hospitalization and even require that recipients be maintained as inpatients. Further, existing pain management options limit the ability of patients suffering from postoperative pain or chronic pain to adjust the timing, intensity and duration of anesthetic effect.

Previous studies have reported injectable sustained drug release systems that provide prolonged duration local anesthesia lasting days to weeks from one or more injections (Epstein-Barash, et al., *Proc. Natl. Acad. Sci.* 106 (17), 7125-30 (2009); Shankarappa, et al., *Proc. Natl. Acad. Sci.*, 109 (43), 17555-60 (2012); Padera, et al., *Anesthesiology*, 108 (5), 921-8 (2008); Kohane, et al., *Pain*, 379 104 (1-2), 415-21 (2003); Colombo, et al., *Mater. Res., Part A*, 75 (2), 458-64 (2005); Chen, et al., *J. Biomed. Mater. Res.*, 70 (3), 459-66 (2004); Curley, et al., *Anesthesiology*, 386 84 (6), 1401-10 (1996); Cohen, et al., *J. Controlled Release*, 160 (2), 346-52 (2012); You, et al., *Small*, 6 (9), 1022-31 (2010)). However, these formulations have the limitation that once initiated, nerve blockade proceeds relatively monotonically until the drug content is depleted.

Peripheral nerves are surrounded by the perineurium, which is composed of a basal membrane with a layer of perineurial cells and tight junctions limiting paracellular permeability. Delivery of analgesic drugs is often impeded by the perineurium. For example, tetrodotoxin (TTX) is an attractive candidate in peripheral nerve anesthesia because of its reduced potential for inducing cardiac and nervous system toxicity. It has a high affinity for voltage dependent sodium channels of the peripheral nerve, but a poor affinity for the cardiac sodium channel isoform. It also does not cross the blood brain barrier. Voltage-gated sodium channels play important roles in nociceptive nerve conduction (Nassar M A, et al., *Proc Natl Acad Sci USA*, 101:12706-12711 (2004); Zimmermann K, et al., *Nature*, 447:855-858 (2007)), but candidate anesthetics (e.g., specific antagonists of sodium channels) are often not effective in vivo because of lack of permeability of the perineurial barrier. Hence, high concentrations of anesthetics and multiple dosages are often required to achieve clinically effective and prolonged anesthesia. Although permeation enhancers have been used to increase the permeability of lipid barriers and, they can be associated with myotoxicity.

There exists a need for systems for the delivery of local anesthetic that can provide repeated or prolonged analgesia on-demand, following a single administration.

It is therefore an object of this invention to provide compositions and methods for repeatable and adjustable on-demand anesthesia with minimal toxicity and improved efficiency and prolonged nerve blockade duration.

It is a further object of the invention to provide a controlled delivery system for which the drug release can be modulated by a patient and/or a medical practitioner in response to changes in the need for anesthesia, level of patient activity, etc.

It is a further object of the invention to provide specific formulations of two or more different classes of drugs and a trigger release system which are both safe and efficacious in humans, that elicit repeatable, adjustable, consistent and prolonged peripheral nerve blockade for up to five or more days following a single application.

SUMMARY OF THE INVENTION

Compositions and methods for administration of local anesthetics that are delivered by a single injection and enable repeated on-demand, high-permeation analgesia over extended periods have been developed.

Pharmaceutical compositions are provided including liposome, particle, or microbubble formulations including an effective amount of one or more site 1 sodium channel blockers, optionally one or more alpha-2-adrenergic agonists, where one or more triggerable elements are present. The triggerable elements allow release of the encapsulated anesthetic drugs or enhancement of the permeation of anesthetic drugs when an appropriate triggering agent or stimulus is applied. Exemplary triggering agents or stimuli include external stimuli such as near-infrared irradiation, UV- and visible light, light-emitting diode (LED), sonic energy (e.g., ultrasound), and magnetic field. The triggerable elements include materials associated with or encapsulated within the liposomes or particles that can cause release of liposomal content in response to the triggering agent(s) or stimuli, and microbubbles capable of creating shock waves when exposed to ultrasound to transiently disrupting nearby biological structures. Exemplary triggerable elements include gold nanorods, 1,4,8,11,15,18,22,25-octabutoxyphthalocyaninato-palladium(II), PdPc(OBu)$_8$, photosensitizers such as protoporphyrin IX, and gas-filled microbubbles shelled with a lipid or a protein.

Exemplary anesthetics or other agents to be delivered in triggerable liposomes, particles, or microbubble formulations generally include sodium channel blockers including site 1 sodium channel blockers (S1SCBs) (e.g., tetrodotoxin ("TTX"), neosaxitoxin, and saxitoxin) and extracellular sodium channel blockers (e.g., bupivacaine), alpha-2-adrenergic agonist (e.g., dexmedetomidine), and additives such as glucocorticoid (e.g., dexamethasone (DMED)). In some forms, these agents are co-loaded in the same liposome, particle, or microbubbles. In other forms, these agents are separately loaded in different liposomes, particles, or microbubbles, and mixtures of different liposomes, particles, or microbubbles are applied as the formulation for on-demand triggered release with repeatability and/or sustained nerve block for local anesthesia.

For example, co-injecting liposomes encapsulating DMED with liposomes encapsulating TTX prolongs the duration of pain relief, increases the number of triggerable nerve block events from 1, 2, or 3 events to 5, 6, 7, 8, 9, or more events with just one single injection of formulation, and greatly reduces the irradiance needed to induce nerve block by about 95%, 90%, 85%, 80%, 75%, 70%, 65%, 60%, 55%, or 50%. Therefore, light sources with various intensities and duration of irradiances can be employed in triggering nerve block, including laser and light-emitting diodes (LEDs). Another example shows that adding dexamethasone further prolongs the effect of co-encapsulated local anesthetics. The general approach of adding a second compound that enhances the efficacy of the first generally improves the performance of other triggered drug delivery systems. The more efficacious nerve block obtained with local anesthetics allows for anesthesia triggered at greater depths of tissue, more repeatable triggered events at lower irradiance or shorter irradiation, and minimizes potential thermal injury.

Another example shows that co-administering liposomes encapsulating bupivacaine, liposomes encapsulating dexamethasone, or liposomes encapsulating DMED, greatly enhances the duration of local anesthesia, compared to administering liposomes only encapsulating bupivacaine and co-administering only two populations, i.e., liposomes encapsulating bupivacaine and liposomes encapsulating DMED. The improvement on nerve block duration induced by co-administering these three populations can be about 150%, 200%, 250%, 300%, or more of the duration achieved by control groups administering one or two populations.

Methods for administration of local anesthetics that are delivered by a single administration and produce repeated on-demand, or highly penetrated, analgesia over extended periods are provided. Generally, the methods include the steps of administering to a subject liposome, particle, or microbubble formulations including one or more sodium channel blockers including site 1 sodium channel blockers, optionally one or more alpha-2-adrenergic agonists or other active agents, and one or more triggerable elements (which may be encapsulated or dispersed within, or form part of, the liposomes or particles, or dispersed with active agents or with active agents in the liposomes or particles); applying a triggering agent or stimulus, to the subject to allow release, improved quality and consistency, prolongation of nerve blockade, or all, of sufficient amount of active agents from the liposomes for pain relief; optionally removing the triggering source to prevent further release once the level of pain relief is achieved.

The methods can be repeated or adjusted for trigger frequency and intensity at the discretion of the patient or medical practitioner to allow further triggered drug release, various levels of anesthetic penetration through biological tissues, or both. In some embodiment, the compositions are effective for one to four separate triggering events and can provide local pain relief to the subject for up to five or more days following a single application. In other embodiments with the application of ultrasound, microbubbles facilitate acoustic cavitation, thereby enhancing the flux of anesthetics (e.g., hydrophilic molecules such as TTX) across biological barriers of the peripheral nerve, and prolonging the duration of nerve blockade from minutes to hours (1, 2, 3, or more hours) without resorting to sustained release formulations.

Generally, triggering agents such as light, ultrasound, magnetic fields and combinations, will be administered at a suitable frequency and intensity for a suitable period of time to deliver the desired dosage from the liposome, particle, or microbubble formulations without causing tissue injury or increasing muscular inflammation or local neurotoxicity. In a preferred embodiment, the triggering agent is applied at a relatively low intensity to minimize tissue injury.

BRIEF DESCRIPTION OF THE DRAWINGS

FIG. 1 is a histogram showing percentage of cell viability for C2C12 and PC12 cells, respectively, after exposure to TTX/DMED-loaded liposomes conjugated with gold nanorods (Lip-GNR-TD) for 1, 2, 3 and 4 days, respectively. TTX=Tetrodotoxin; DMED=Dexmedetomidine. Data are means with standard deviations (n=4).

FIG. 2 is a line graph showing the cumulative release of total encapsulated rhodamine 6G (R6G) over time (hours) from liposomes with gold nanorods (Lip-GNR-R6G) or liposomes without nanorods (Lip-R6G), respectively, at 37° C. or 43° C. Data are means with standard deviations (n=4).

FIGS. 3A-3B are graphs showing temperatures of solutions containing empty liposomes conjugated with gold nanorods (Lip-GNR-0) and their size after irradiation. FIG. 3A shows temperatures of a solution of Lip-GNR-0 over time (minutes) with continuous irradiation at the intensity of 17, 25, 42 and 75 $mW/cm^2$, respectively. FIG. 3B shows temperatures (○) of a solution of Lip-GNR-0 over time of minutes with five cycles of irradiation with 75 $mW/cm^2$ NIR laser; and bar-graphs showing size of Lip-GNR-0 at the end of each off-state. Data are means with standard deviations (n=4).

FIGS. 4A-4B are graphs showing percentage of R6G release from (Lip-GNR-R6G) after 10 min irradiation of an 808 nm continuous wave NIR laser at an intensity of 0, 8, 17, 25, 42, 75 and 141 $mW/cm^2$, respectively (FIG. 4A); and after 10 min irradiation of an 808 nm continuous wave NIR laser at intensity of 17 $mW/cm^2$ with 1, 2, 3, 4 and 5 trigger cycles (FIG. 4B).

FIG. 5 is a graph showing the % cumulative release of total encapsulated TTX and DMED from Lip-GNR-TD in vitro at 37° C. over time in days for up to 18 days. Data are means with standard deviations (n=4).

FIGS. 6A-6B are graphs showing percentage of TTX and DMED release (FIG. 6A) accumulative over time (minutes) from Lip-GNR-TD in vitro under continuous irradiation with an 808 nm continuous wave NIR laser at intensity of 25 $mW/cm^2$. (FIG. 6B) Percentage of TTX and DMED release non-accumulative over 5 cycles of 10 min irradiation separated by 30 min. Data are means with standard deviations (n=4).

FIGS. 7A-7D are graphs showing phototriggered local anesthesia in the rat footpad. Following injection (arrow labeled "Inj") of 100 μL of a mixture of Lip-GNR-TD and Lip-GNR-R6G and subsequent irradiation (arrows, 808 nm continuous wave NIR laser at 75, 141, and 272 $mW/cm^2$, for 10 min, over 4 trigger cycles), the effect of local anesthesia is represented as a percentage of maximum possible effect (MPE; see Methods) (FIG. 7A); the highest MPE (FIG. 7B);

the duration in hours of local anesthesia (FIG. 7C); the area under the curve (AUC) of the % MPE-time curves for panel (FIG. 7D). Data are medians (n=4-6 per group; for the initial local anesthesia, n=14 for the 3 groups). Data are medians with 25th and 75th percentiles in FIGS. 7B-7D. *p<0.05, p<0.01, and p<0.001 (top asterisks, 75 versus 272 mW/cm$^2$; bottom asterisks, 141 versus 272 mW/cm$^2$).

FIG. 8 are graphs showing the effect of local anesthesia in the rat footpad as a percentage of Maximum possible effect MPE over time of hours following injection of Lip-TD and Lip-GNR-0. The black arrow indicates a laser irradiation. Data are medians with 25$^{th}$ and 75$^{th}$ percentiles (n=6).

(FIG. 9B) of a solution of Lip-GNR-R6G over time of hours after incubation at 4, 37 and 43° C.

Figure 12:
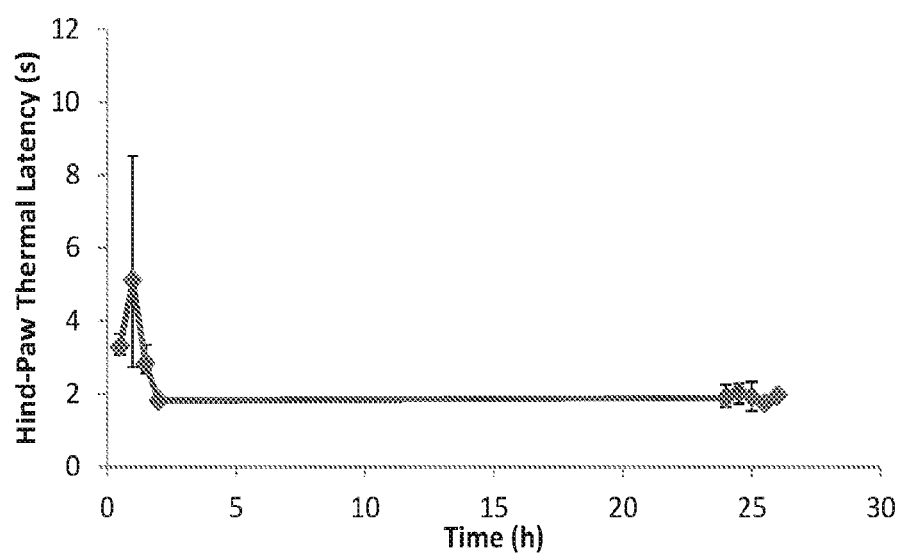

FIG. 12 is a graph showing rat hindpaw thermal latency over time in hours following injection of bupivacaine encapsulated in PdPC(OBu)$_8$ liposomes. The black arrow indicates the irradiation (730 nm, 330 mW/cm$^2$, 15 min) at 24 hr. Data are medians with 25$^{th}$ and 75$^{th}$ percentiles (n=4).

Figure 13:
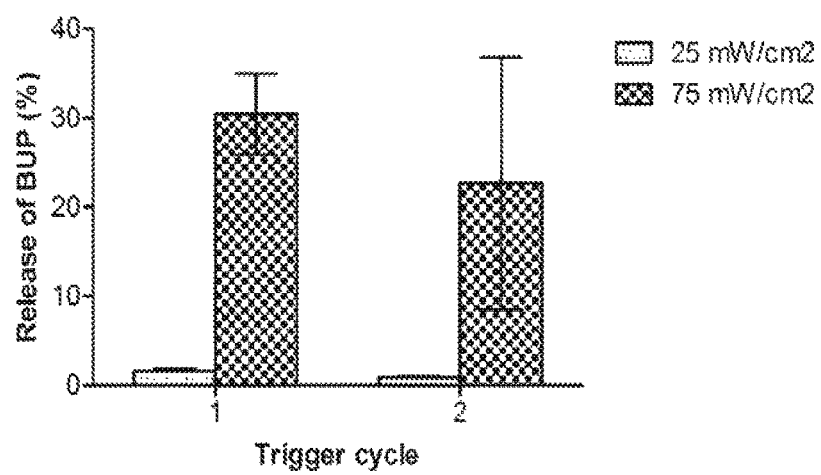

FIG. 13 is a histogram showing the percentage of bupivacaine release from Lip-GNR liposomes loaded with bupivacaine at 37° C. with irradiation (808 nm, 10 min) at intensity of 25 and 75 mW/cm$^2$. Data are means with standard deviations (n=4).

Figure 14:
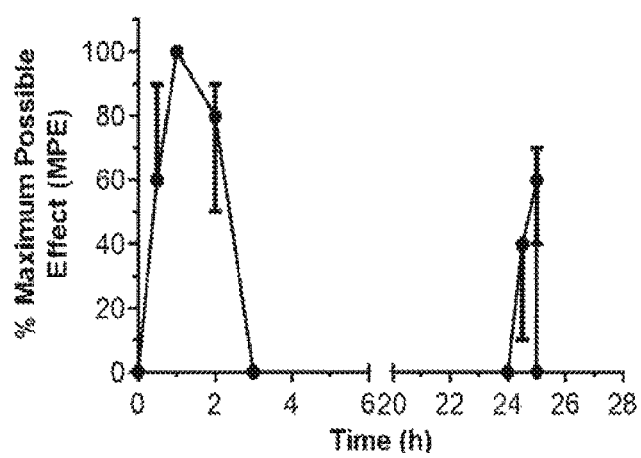

FIG. 14 is a graph showing duration (in hours) of local anesthesia, as a percentage of MPE, following injection of bupivacaine-loaded Lip-GNR to the rat footpad. Irradiation was performed at 24 h (808 nm, 141 mW/cm$^2$, 10 min).

Figure 15:
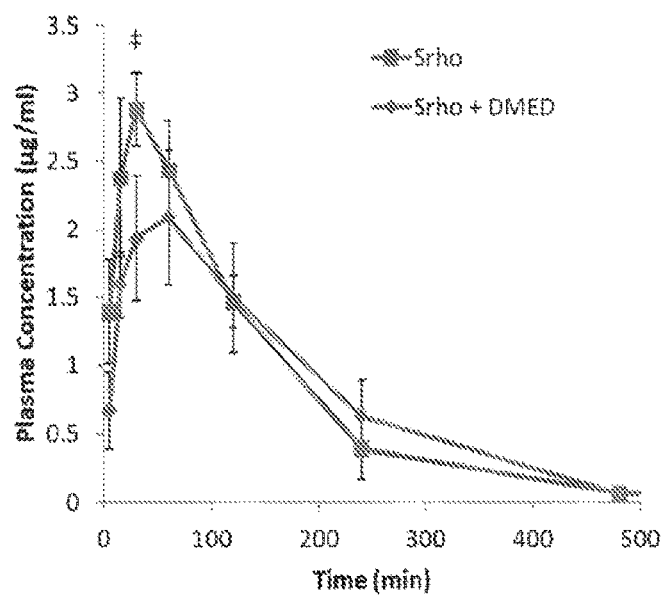
Figure 16:
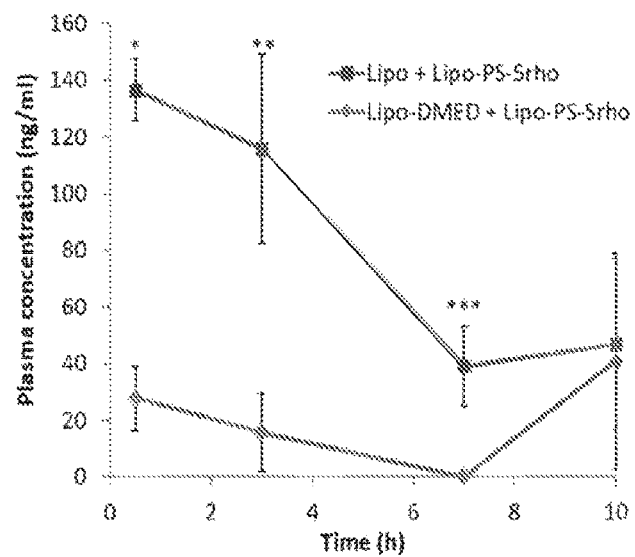

FIG. 15 is a line graph showing the plasma concentration of the fluorescent dye sulforhodamine B (Srho) (μg/ml) over time (min) following peri-sciatic injection of free srho in PBS solution with or without free DMED. (means±SD, n=4. ‡P=0.01;) FIG. 16 is a line graph showing the plasma concentration (μg/ml) of lipo-Srho with Lipo-DMED or with blank liposomes (Lipo). (means±SD, n=4. *P=8.7×10$^{-6}$; P=0.0014, *P=0.0014.)

Figure 17A:
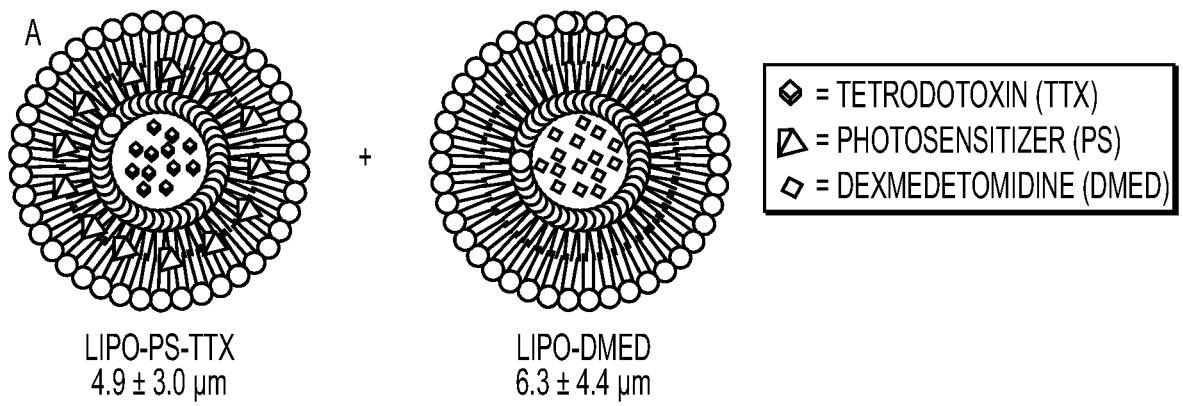
Figure 17B:
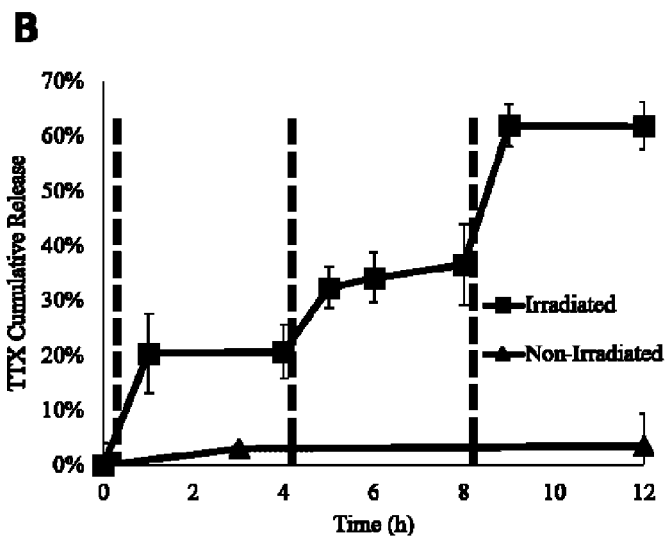
Figure 17C:
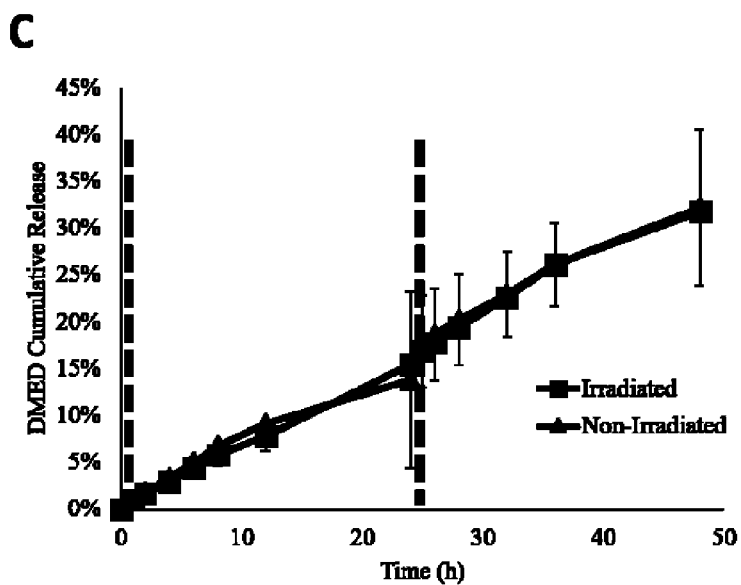

FIG. 17A is a schematic of the liposomes Lipo-PS-TTX and Lipo-DMED and their corresponding particle size. FIG. 17B is a line graph showing cumulative TTX release (%) from Lipo-PS-TTX+Lipo-DMED with or without irradiation over time (hour, h). FIG. 17C is a line graph showing cumulative DMED release (%) from Lipo-PS-TTX+Lipo-DMED with or without irradiation over time (h). The dotted grey lines in FIGS. 17B and 17C indicate irradiation events at 730 nm, 100 mW/cm$^2$, for 10 min. (Data are means±SD, n=4.)

Figure 18:
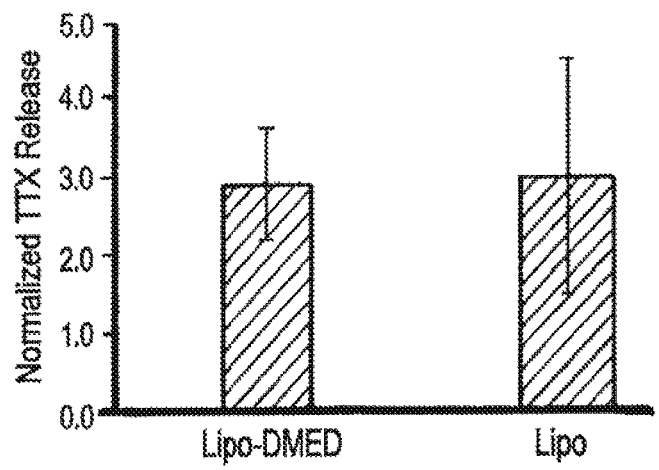

FIG. 18 is a bar graph showing in vitro normalized TTX release of Lipo-PS-TTX with Lipo-DMED or with Lipo. (Normalized TTX release was calculated using the release from the non-irradiated liposomes as the base value. Data are means±SD, n=4.)

Figure 19A:
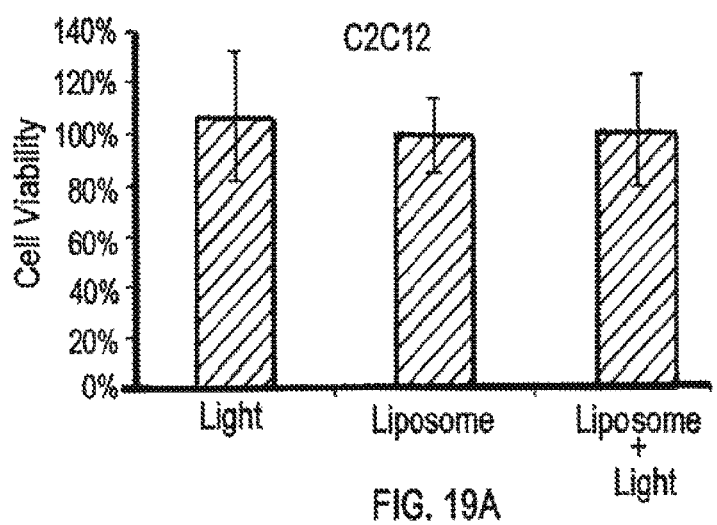
Figure 19B:
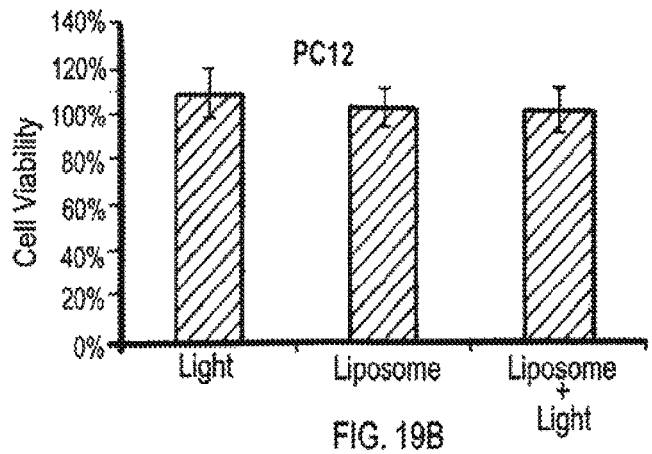

FIGS. 19A and 19B are bar graphs showing the cell viability (%) of C2C12 cells (FIG. 19A) and PC12 cells (FIG. 19B) upon exposure to light (irradiation at 730 nm, 100 mW/cm$^2$, 10 min), to diffusible components from liposome (Lipo-PS-TTX+Lipo-DMED 1:1 (vol) mixture), or to liposome+light (Lipo-PS-TTX+Lipo-DMED 1:1 (vol) mixture irradiated with 730 nm, 100 mW/cm$^2$, 10 min. (Data are means±SD, n=4.)

Figures 20A, 20B, 20C:
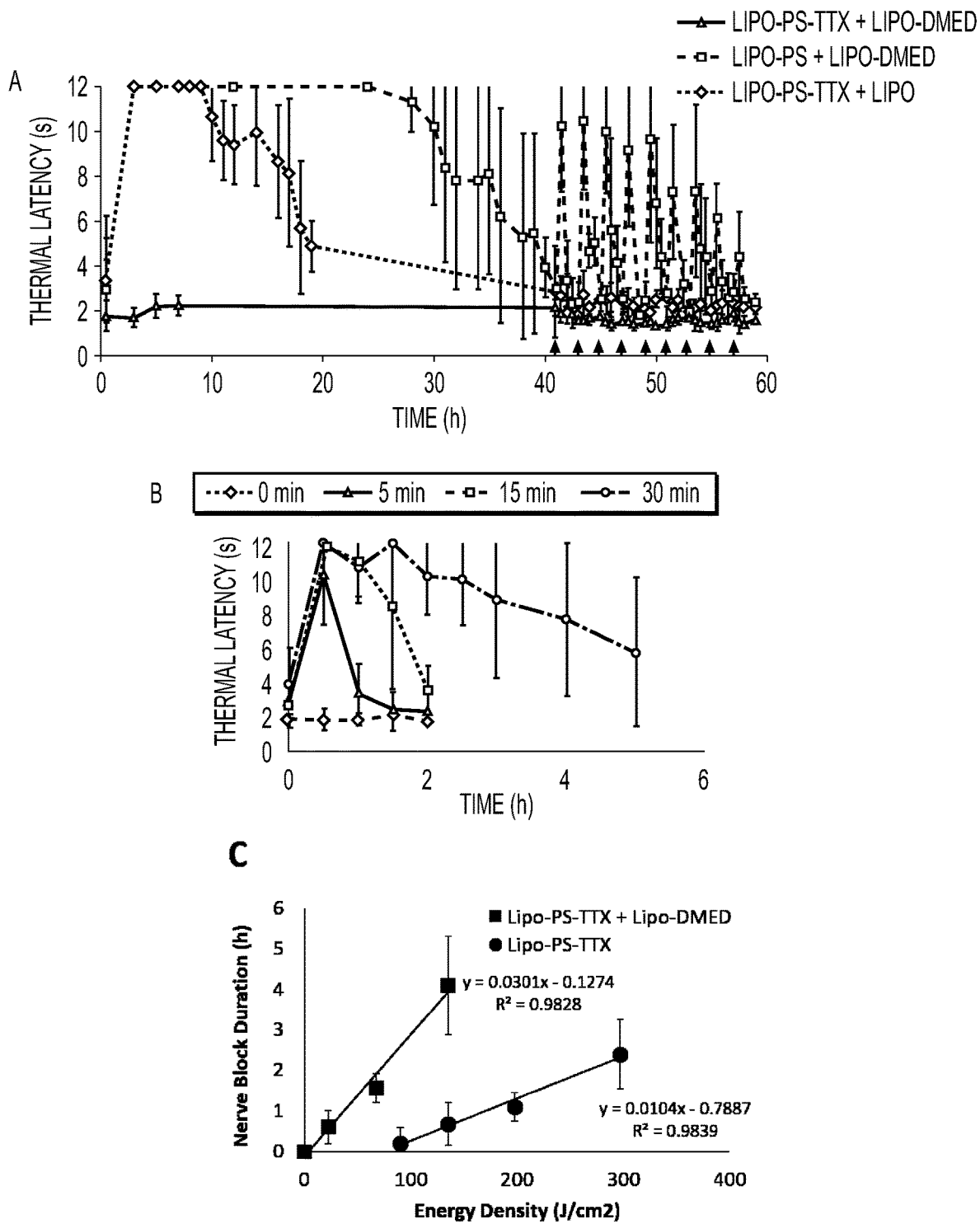

FIG. 20A is a line graph showing the thermal latency (s) over time (h) of animals administered with different liposome combinations using low power near infrared (NIR) light. Black arrows indicate irradiation events at 730 nm for 5 min at 75 mW/cm$^2$. FIG. 20B is a line graph showing thermal latency (s) over time (h) of animals administered with Lipo-PS-TTX+Lipo-DMED and 41 hours later subject to irradiation (730 nm, 75 mW/cm$^2$) for different durations, i.e., 0 min, 5 min, 15 min, and 30 min. FIG. 20C is a line graph showing the nerve block duration (h) over the irradiation (730 nm) energy density (J/cm$^2$), induced by Lipo-PS-TTX with or without co-injection of Lipo-DMED. (Data are means±SD, n=4.)

Figure 21A:
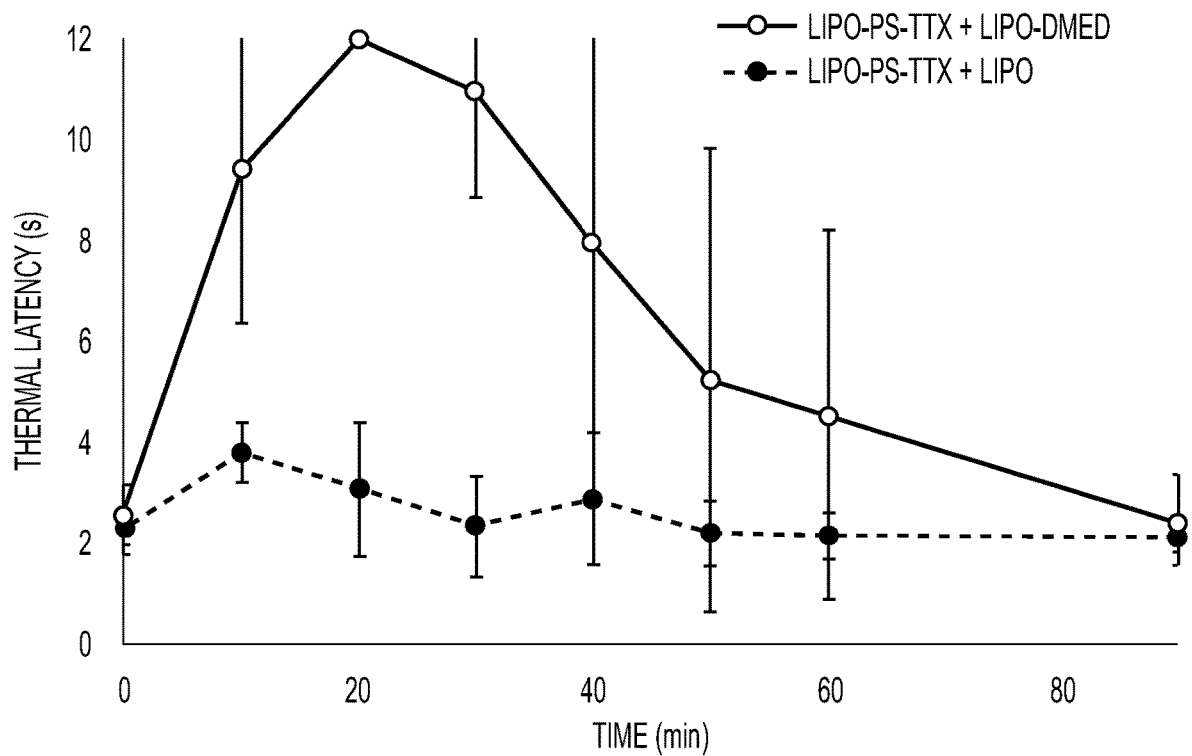
Figure 21B:
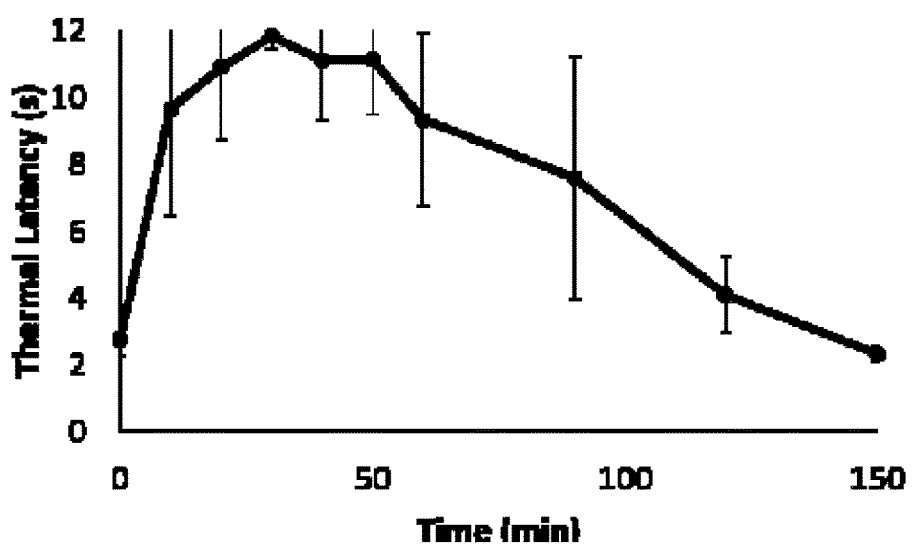

FIG. 21A is a line graph showing the thermal latency (s) over time (min) of animals administered with different liposome combinations and 41 hours later subject to irradiated with a 725 nm-755 nm LED at 50 mW/cm$^2$ for 15 min. FIG. 21B is a line graph showing the thermal latency (s) over time (min) of animals administered with different liposome combinations and 41 hours later subject to irradiated with a 730 nm laser at 50 mW/cm$^2$ for 15 min. (Data are means±SD, n=4.)

Figure 22:
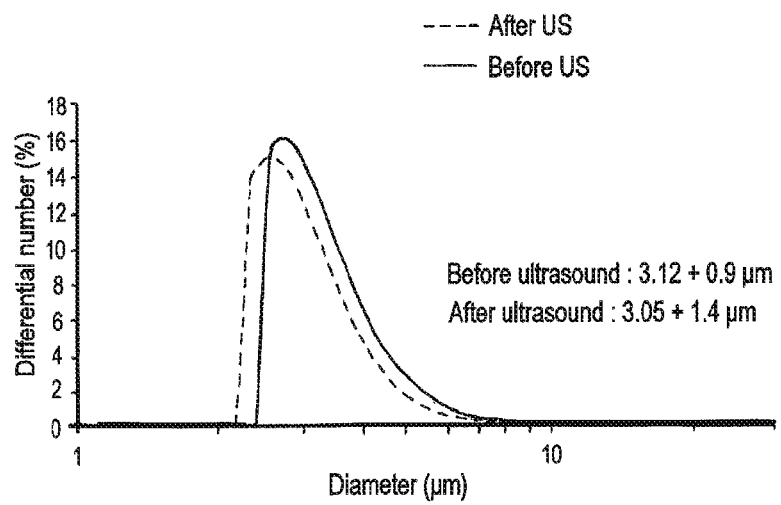

FIG. 22 is a line graph showing the differential number (%) over diameter (μm) of Lipo-PPIX before and after ultrasound exposure (3 W/cm$^2$, 1 MHz, 10 min) determined by dynamic light scattering.

Figures 23A, 23B, 23C, 23D:
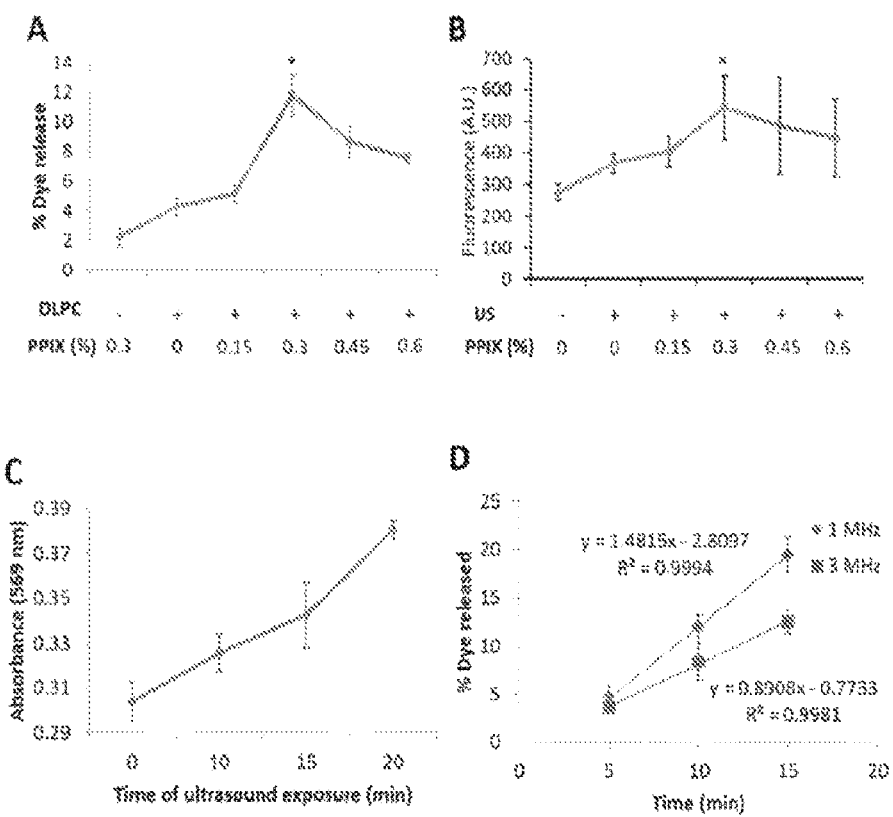

FIG. 23A is a line graph showing the dye release (%) from liposomes loaded with different amount (% mg PPIX/mg lipid) in the presence or absence of DLPC after ultrasound exposure (3 W/cm$^2$, continuous application, 1 MHz, 10 min). FIG. 23B is a line graph showing ROS generation (measured by fluorescence, A.U.) by liposomes loaded with different amounts of PPIX (% mg PPIX/mg lipid) after 10-min ultrasound (US) exposure at 1 MHz, 3 W/cm$^2$. FIG. 23C is a line graph showing lipid peroxidation (measured by absorbance) over time of continuous ultrasound exposure (min) at 3 W/cm$^2$, 1 MHz in liposomes with PPIX loading at 0.3% mg PPIX/mg lipid. *p<0.05. Data are means±SD, N=4. FIG. 23D is a line graph showing in vitro dye release (%) over time (min) of continuous ultrasound duration for 1 MHz or 3 MHz at 3 W/cm$^2$. FIG. 23E is a bar graph showing in vitro dye release (%) over intensity (W/cm$^2$) of ultrasound continuously applied for 10 min at 1 MHz. FIG. 23F is a bar graph showing in vitro dye release (%) over duty cycles (%) of ultrasound (1 MHz, 10 min, 3 W/cm$^2$).

FIG. 24 is a line graph showing ultrasound-triggered dye release (%) over time, where ultrasound was applied for 5 min at each time point indicated by arrows at 1 MHz, 3 W/cm$^2$.

FIGS. 25A and 25B are line graphs showing TTX released (%) at 37° C. over time (h) from Lipo-PPIX-TTX (FIG. 25A) and from Lipo-TTX (FIG. 25B), respectively, with or without ultrasound (US). Arrows represent the application of ultrasound (1 MHz, 3 W/cm$^2$, continuous, 10 min) at the 5 h time point. Data are means±SD, N=4.

Figures 26A, 26B, 26C, 26D:
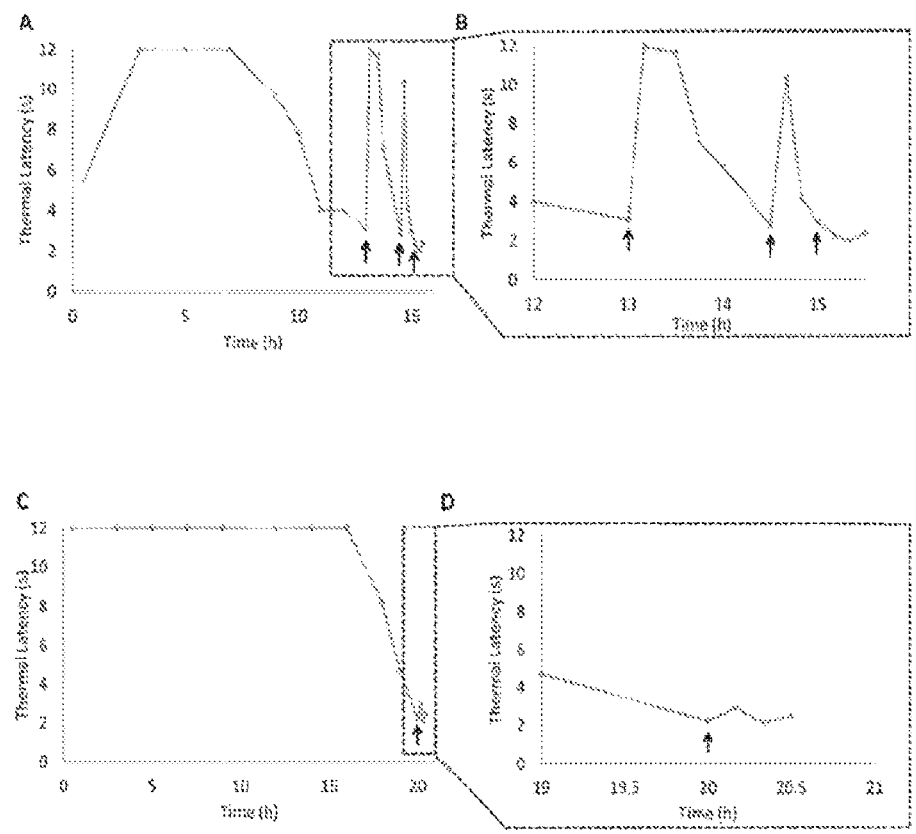

FIG. 26A is a line graph showing thermal latency (s) of one representative animal of four over time (h) after injection of 200 μL Lipo-PPIX-TTX formulation and subsequent insonation. FIG. 26B is a line graph of time=12 h to 15 h of FIG. 26A. FIG. 26C is a line graph showing thermal latency (s) of one representative animal of four over time (h) after injection of 200 μL Lipo-TTX formulation and subsequent insonation. FIG. 26D is a line graph of time=19 h to 21 h of FIG. 26C.

Figure 27C:
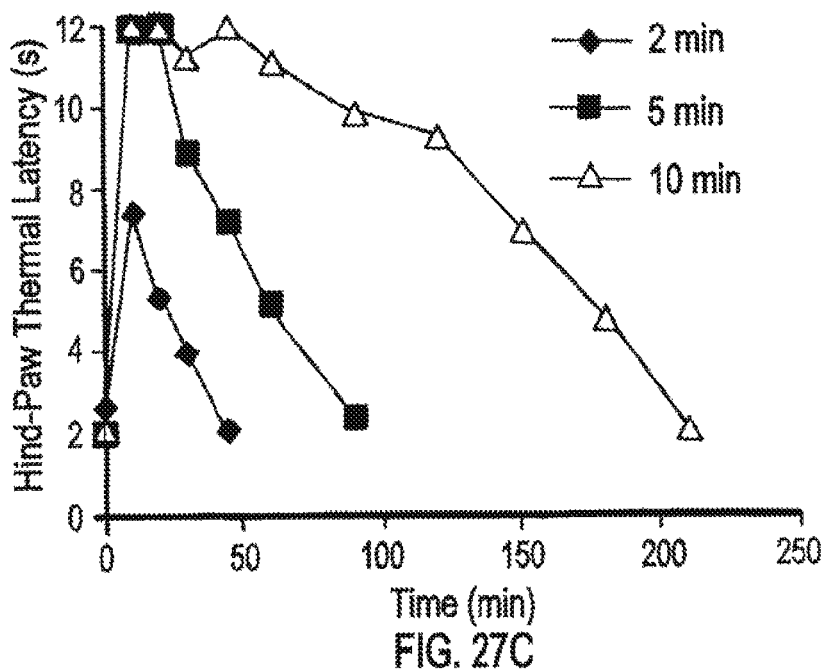
Figure 27D:
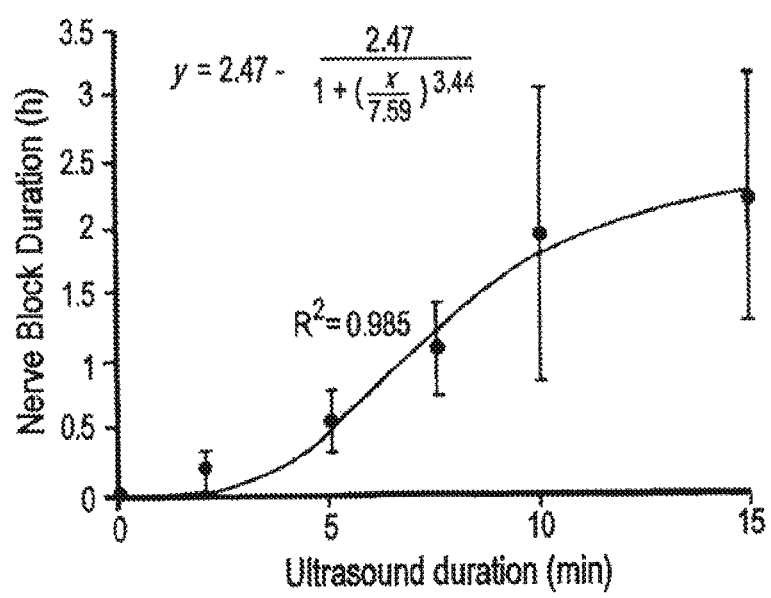

FIG. 27A is a line graph showing thermal latency (s) of one representative animal of four over time (h) after injection of Lipo-PPIX-TTX+Lipo-DMED and subsequent insonation. FIG. 27B is a line graph of time=38 h to 48 h of FIG. 27A, where 10-min insonations are indicated by black arrows, at 1 MHz, continuous application, 3 W/cm$^2$. FIG. 27C is a line graph showing hind-paw thermal latency (s) over time following ultrasound-triggered nerve block (after the initial nerve block wore off) using 10, 5 or 2-min insonation. FIG. 27D is a line graph showing the duration of nerve block (h) over the duration of insonation (min).

Figure 28A:
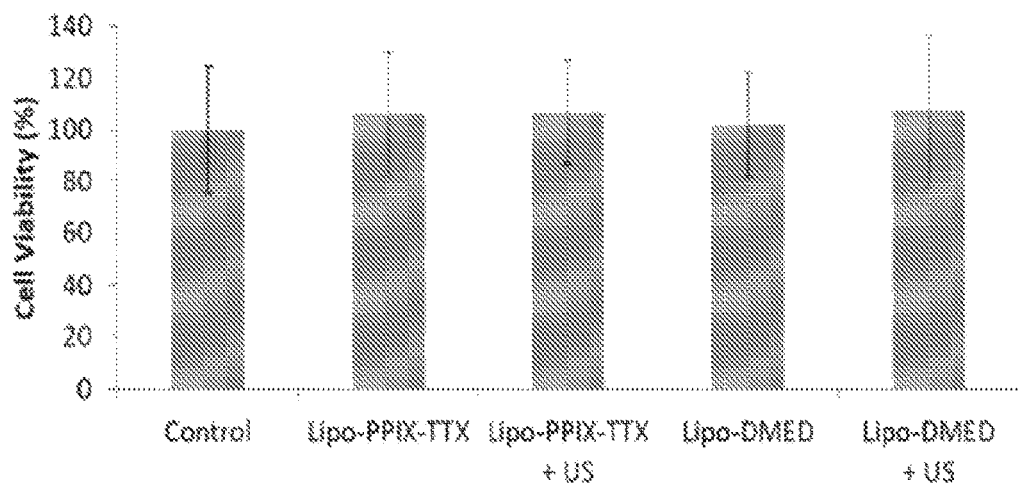
Figure 28B:
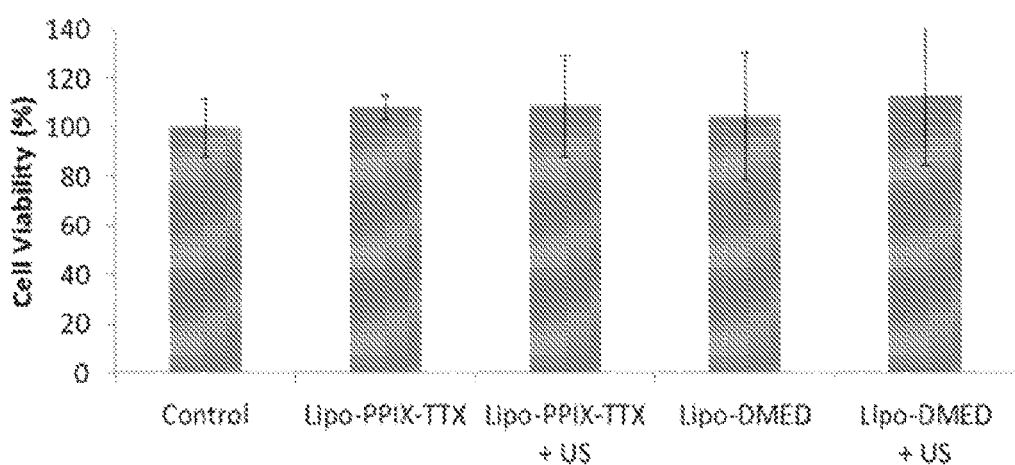

FIGS. 28A and 28B are bar graphs showing cell viability (%) of PC12 cells (FIG. 28A) and C2C12 cells (FIG. 28B), respectively, to the diffusible components from liposomes loaded with different compounds, with or without pretreatment by ultrasound (3 W/cm$^2$, 1 MHz, 10 min). Cells were exposed to liposomes via a 24-well Transwell® for 24 h prior. Cell viability was measured with the MTS assay. Untreated cells were indicated as "Control". Data are means±SD, N=4.

Figure 29:
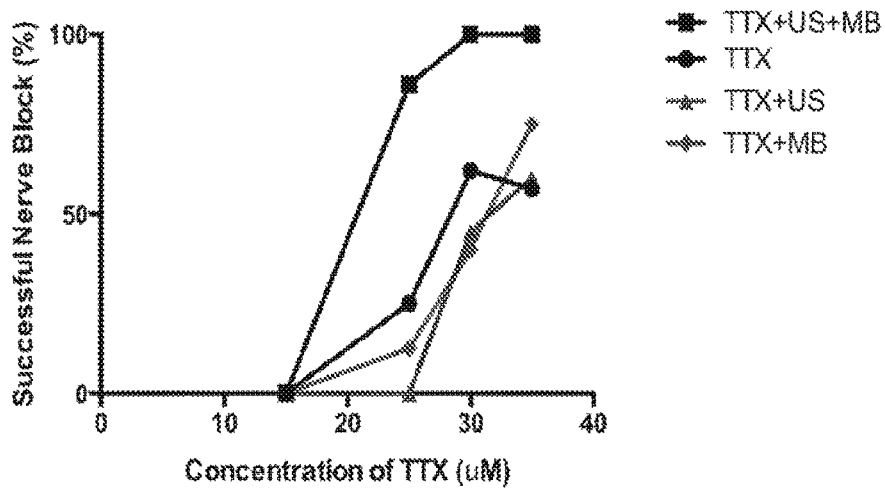

FIG. 29 is a line graph showing successful sciatic nerve block, as a percentage (%), in rats administered with different concentrations of TTX in different dosing processes. The processes included (1) co-injection of TTX and microbubbles followed by ultrasound treatment, denoted as TTX+US+MB, where TTX was injected at 25 µM (N=7), 30 µM (N=9), or 35 µM (N=7); (2) injection of TTX followed by ultrasound treatment, denoted as TTX+US, where TTX was injected at 25 µM (N=4), 30 µM (N=9), or 35 µM (N=8); (3) co-injection of TTX and microbubbles without ultrasound treatment, denoted as TTX+MB, where TTX was injected at 25 µM (N=8), 30 µM (N=8), or 35 µM (N=6); and (4) injection of TTX only, denoted as TTX, at 25 µM (N=4), 30 µM (N=8), or 35 µM (N=7). (**$p<0.05$, Mann Whitney U test was used because neurobehavioral data is not normally distributed).

Figure 30:
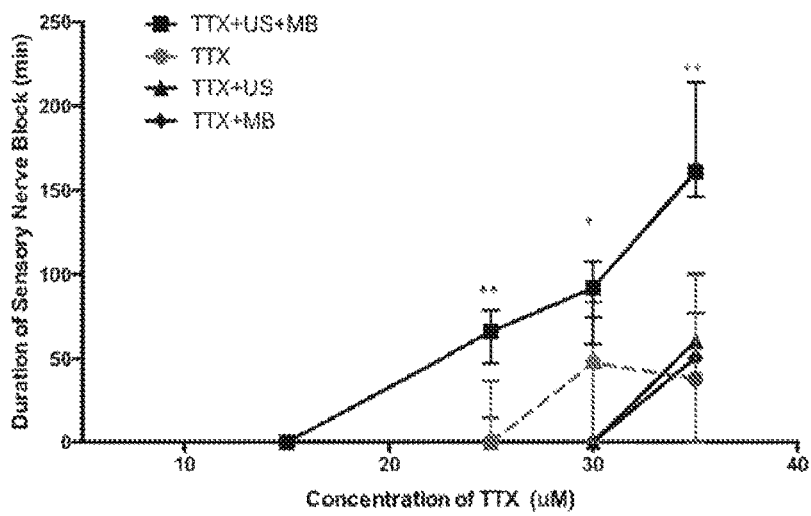

FIG. 30 is a line graph showing duration (in minutes) of sensory nerve block on rats administered with different concentrations of TTX in different dosing processes as described for FIG. 15, including TTX+US+MB, TTX, TTX+US, and TTX+MB. (Data is presented as medians with 25th to 75th interquartile range. **$p<0.05$, *$p=0.053$, Mann Whitney U Test was used because neurobehavioral data is not normally distributed)

Figure 31A:
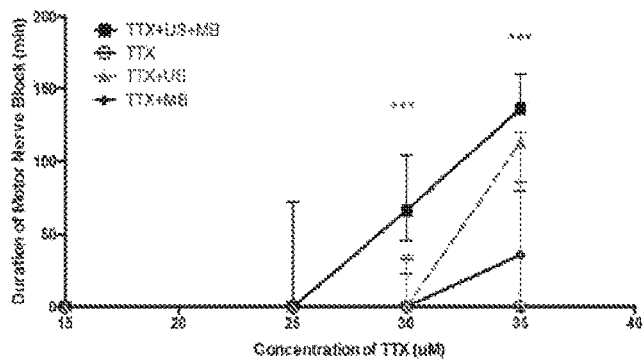
Figure 31B:
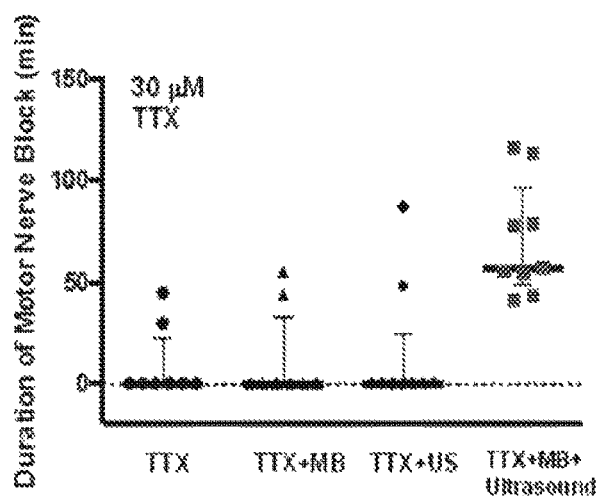

FIGS. 31A and 31B are a line graph (31A) and a dot plot (31B), showing duration (in minutes) of motor nerve block on rats administered with different concentrations of TTX in different dosing processes as described for FIG. 29, including TTX+US+MB, TTX, TTX+US, and TTX+MB. (Data is presented as medians with 25th to 75th interquartile range. ***$p<0.001$ comparing TTX+US+MB with TTX, Mann Whitney U Test was used because neurobehavioral data is not normally distributed.)

Figure 32A:
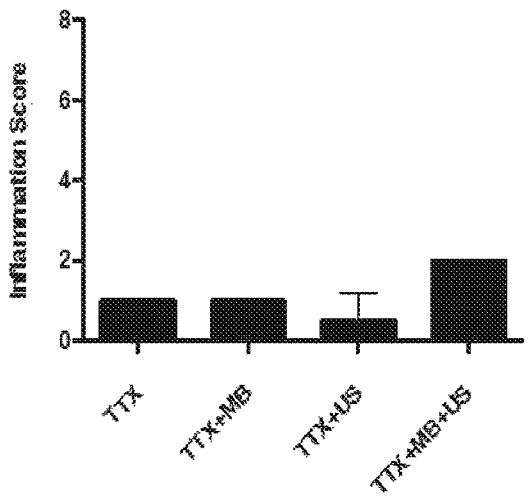
Figure 32B:
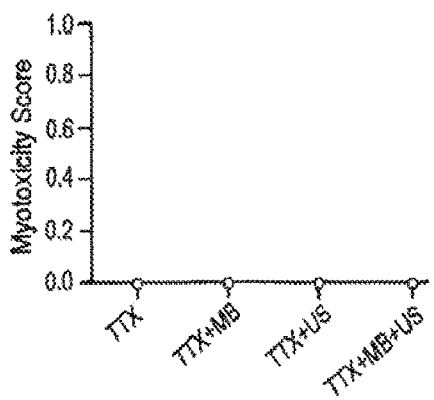

FIG. 32A and FIG. 32B are bar graphs showing scores of inflammation (32A) and myotoxicity (32B), of muscle specimens stained with hematoxylin and eosin from rats, 4 days after administration with TTX in different dosing processes as described for FIG. 29. (Mann Whitney U Test was used because the scoring data is ordinal.)

DETAILED DESCRIPTION OF THE INVENTION

I. Definitions

The term "Analgesia" refers to insensibility to pain without loss of consciousness.

The term "Anesthetic" refers to a loss of sensation (local; not causing loss of consciousness; systemic, with loss of consciousness) and usually of consciousness without loss of vital functions.

The term "Infiltration" refers to injection into one or more layers or areas of tissue.

The term "Injection" refers to injection into a single point in tissue or lumen.

The term "Nerve block" refers to local anesthesia produced by interruption of the flow of impulses along a nerve trunk.

The term "treating" preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The term "pharmaceutically acceptable salts" is art-recognized, and includes relatively non-toxic, inorganic and organic acid addition salts of compounds. Examples of pharmaceutically acceptable salts include those derived from mineral acids, such as hydrochloric acid and sulfuric acid, and those derived from organic acids, such as ethanesulfonic acid, benzenesulfonic acid, and p-toluenesulfonic acid. Examples of suitable inorganic bases for the formation of salts include the hydroxides, carbonates, and bicarbonates of ammonia, sodium, lithium, potassium, calcium, magnesium, aluminum, and zinc. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine;

The phrase "therapeutically effective amount" refers to an amount of the therapeutic agent that, when incorporated into and/or onto particles described herein, produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

The terms "incorporated" and "encapsulated" refers to incorporating, formulating, or otherwise including an active agent into and/or onto a composition that allows for release of such agent in the desired application. The terms contemplate any manner by which a therapeutic agent or other material is incorporated into a polymer matrix, including for example: attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to-the incorporation of a therapeutic agent or other material and at least one other therapeutic agent or other material in a subject composition. More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer that it is dispersed as small droplets, rather than being dissolved, in the polymer.

II. Compositions

Delivery systems providing controlled delivery (e.g., on-demand triggered release, or enhanced flux and penetration) of site I sodium channel blocking anesthetic, alone or in combination with other therapeutic, prophylactic and/or diagnostic agents, from triggerable liposomes or particles or with triggerable microbubbles. The compositions and methods can be used to control the release in a patient. Compositions for the on-demand delivery of anesthetic agents to a subject include one or more anesthetic agents that may be encapsulated in liposomes or particles, and a triggerable element that enables delivery of the one or more anesthetic agents in response to a triggering agent or event. The triggering agent or event can be any one or more of near-infrared irradiation (NIR), ultraviolet light (UV), ultrasound, visible light and a magnetic field. The triggerable elements are any material associated with the liposomes that release liposomal content in response to the triggering agent(s) or event(s), or spontaneously-formed or exogenously administered microbubbles capable of creating shock waves and transiently disrupting nearby biological tissue after exposure to sonic energy. In some embodiments, the triggerable elements are gold nanorods and 1,4,8,11,15, 18,22,25-octabutoxyphthalocyaninato-palladium(II), PdPc $(OBu)_8$. In other embodiments, the triggerable elements are gas-filled, e.g., air or perfluorocarbon, microbubbles.

The amount of drug released and the level of drug permeation in response to each triggering agent or event is controlled by the frequency or wavelength, intensity and duration of the triggering agent/stimulus that is administered. Once the triggering agent/stimulus is removed or turned off, the release of encapsulated drugs in the embodiments of the liposomal formulation stops. The release of encapsulated agents is resumed in response to another application of triggering agent/stimulus.

In some embodiments the compositions are delivered in amounts effective to allow repeatable and adjustable block of the local anesthetic, with no systemic toxicity.

In some embodiments the compositions are delivered in amounts effective to allow for enhanced flux to target sites and improved quality and consistency of anesthesia, with no local toxicity.

In some embodiments the composition is administered in a formulation locally at the site where the nerve is to be blocked, preferably as a suspension.

A. Triggerable-Delivery Vehicles

Triggerable-delivery vehicles or co-vehicles include triggerable-release liposomes, particles, or ultrasound-burstable microbubbles.

Triggerable-release liposomes are liposomes with one or more lipids in the lipid bilayer encapsulating one or more active compound. In addition, triggerable release liposomes have triggerable elements that induce changes in the lipid bilayer to allow the release of the encapsulated content when a specific triggering stimulus is applied. Triggerable release liposomes that allow precise control of timing, duration and magnitude of drug release from liposomes in response to an external source are described. In some embodiments, the external stimulus is near-infrared (NIR) radiation.

1. Liposomes

Liposomes are disclosed for the delivery of the anesthetics including site I sodium channel blocker anesthetics, alone or in combination with other agents enhancing local anesthesia.

Liposomes are biodegradable, non-toxic, unilamellar or multilamellar vesicles formed from naturally occurring or synthetic phospholipids. Liposomes have an ability to entrap and retain a wide range of therapeutic agents, either in their aqueous (hydrophilic agents) or their lipid (hydrophobic) phases (Senior, *Crit. Rev. Ther. Drug Carrier Sys.*, 3, 123-193 (1987); Lichtenberg, *Methods Biochem. Anal.*, 33, 337-362 (1988); Gregoriadis, *Subcell. Biochem.*, 14, 363-378 (1989); Reimer, et al., *Dermatol.*, 195:93 (1997)). Liposomes have been used in clinical practice for treatment of metabolic disorders (Gregoridis, et al., *Prog. Clin. Biol. Res.*, 95, 681-701 (1982), infectious diseases (Richardson, *J. Clin. Pharmacol.*, 29, 873-884 (1983), systemic fungal infections (Grant, et al., *Biochem. Biophys. Acta*, 984, 11-20 (1989) and to reduce the adverse systemic effects of chemotherapeutic drugs (Owen, et al., *Anticancer Drugs*, 3, 101-107 (1992); Gabizon, et al., *Acta Oncol.*, 33, 779-786 (1994)). U.S. Pat. Nos. 7,063,860 and 8,110,217, both by Chancellor, et al., disclose liposomal delivery of capsaicin or botulinum toxin, respectively, to urothelial cells for treatment of bladder dysfunction. Twelve liposomal-therapeutic agent formulations have been approved by the U.S. Federal Drug Administration and an additional twenty-two were in clinical trials (Chang, et al., *Scientific Rep.*, 1, 195 (2012)).

Liposomes are spherical vesicles composed of concentric phospholipid bilayers separated by aqueous compartments. Liposomes can adhere to and form a molecular film on cellular surfaces. Structurally, liposomes are lipid vesicles composed of concentric phospholipid bilayers which enclose an aqueous interior (Gregoriadis, et al., *Int. J. Pharm.*, 300, 125-30 2005; Gregoriadis and Ryman, *Biochem. J.*, 124, 58P (1971)). Hydrophobic compounds associate with the lipid phase, while hydrophilic compounds associate with the aqueous phase.

Production of Liposomes

Suitable methods, materials and lipids for making liposomes are known in the art. Liposome delivery vehicles are commercially available from multiple sources. The liposome may be formed from a single lipid; however, in some embodiments, the liposome is formed from a combination of more than one lipid. The lipids can be neutral, anionic or cationic at physiologic pH.

Incorporation of one or more PEGylated lipid derivatives can result in a liposome which displays polyethylene glycol chains on its surface. The resulting liposomes may possess increased stability and circulation time in vivo as compared to liposomes lacking PEG chains on their surfaces. Liposomes are formed from one or more lipids, which can be neutral, anionic, or cationic at physiologic pH. Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including, but not limited to, 1,2-diacyl-glycero-3-phosphocholines; phosphatidylserine (PS), phosphatidylglycerol, phosphatidylinositol (PI); glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids.

Suitable cationic lipids in the liposomes include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2,3-dioloyloxy)propyl]-N,N-dimethyl amine (DODAP), 1,2-diacyloxy-3-dimethylammonium propanes, N-[1-(2,3-dioleyloxy)propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA), β-alanyl cholesterol, cetyl trimethyl ammonium bromide (CTAB), $diC_{14}$-amidine, N-ferf-butyl-N'-tetradecyl-3-tetradecylamino-propionamidine, N-(alpha-trimethylammonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N, N, N', N'-tetramethyl-, N'-bis(2-hydroxyethyl)-2,3-dioleoyloxy-1,4-butanediammonium iodide. In one embodiment, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)imidazolinium chloride (DOTIM), and 1-[2-(hexadecanoyloxy)ethyl]-2-pentadecyl-3-(2-hydroxyethyl)imidazolinium chloride (DPTIM). In one embodiment, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimethyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

The lipids may be formed from a combination of more than one lipid, for example, a charged lipid may be combined with a lipid that is non-ionic or uncharged at physiological pH. Non-ionic lipids include, but are not limited to, cholesterol and DOPE (1,2-dioleolylglyceryl phosphatidylethanolamine), with cholesterol being most preferred.

In some embodiments, the lipids include 1,2-Dipalmitoyl-sn-glycero-3-phosphocholine (DPPC), 1,2 dipalmitoyl-sn-glycero-3-phospho-(1'-rac-glycerol (DPPG), cholesterol and thiolated PEG-DSPE (HS-PEG-DSPE) with a molar ratio of 6:2:3:0.2.

The liposomes typically have an aqueous core. The aqueous core can contain water or a mixture of water and alcohol. Suitable alcohols include, but are not limited to, methanol, ethanol, propanol, (such as isopropanol), butanol (such as n-butanol, isobutanol, sec-butanol, tert-butanol, pentanol (such as amyl alcohol, isobutyl carbinol), hexanol (such as 1-hexanol, 2-hexanol, 3-hexanol), heptanol (such as 1-heptanol, 2-heptanol, 3-heptanol and 4-heptanol) or octanol (such as 1-octanol) or a combination thereof.

The liposomes can have either one or several aqueous compartments delineated by either one (unilamellar) or several (multilamellar) phospholipid bilayers (Sapra, et al., *Curr. Drug Deliv.*, 2, 369-81 (2005)). Preferably, the liposomes are multilamellar. Multilamellar liposomes have more lipid bilayers for hydrophobic therapeutic agents to associate with.

The compositions can be provided in any pharmaceutically acceptable carrier for injection, such as water, saline, dextrose solutions, carboxymethylcellulose, mannitol, and buffered solutions.

Phase Transition Temperature

Liposomes are useful for remotely triggered drug delivery because they are injectable, often thermosensitive, and tissue response is generally benign (Lu, et al., *Springer International Publishing*: New York; pp 95-122 (2014); Mallick, et al., *J. Nanosci. Nanotechnol.*, 14 (1), 755-65 (2014)).

Phase transition temperature ($T_m$) of liposomes refers to the temperature at which lipid assemblies transition from a solid (crystalline) phase to a fluid (liquid crystalline) phase. Heating the liposomal lipid bilayer over its phase transition temperature increases its permeability and triggers the release of drugs (Maruyama, et al., *Biochim. Biophys. Acta, Biomembr.*, 1149 (2), 209-16 (1993)).

The lipid constituents of liposomes influence the biophysical characteristics of the liposomes. In some embodiments, liposomes are formulated from one or more lipids to influence the phase transition temperature of the liposomes. Preferably, liposomes are formulated to have a phase transition temperature that is within a physiologically relevant range, for example, approximately body temperature. Therefore, in some embodiments, the liposomes are formulated to have a phase transition temperature that is between 33-43° C.

In some embodiments, liposomes include 1,2-Dipalmitoyl-sn-glycero-3-phosphocholine (DPPC) and 1,2 dipalmitoyl-sn-glycero-3-phospho-(1'-rac-glycerol) (DPPG) as the lipid components because their transition temperatures (41° C.) are above but close to mammalian body temperature. In other embodiments, the transition temp can be higher than body temp as long as it does not cause injury to the body Thiolated lipids can be incorporated into the liposomal bilayer to assist in anchoring gold nanoparticles via the thiol-gold interaction.

In some embodiments, thiolated PEG-DSPE (HS-PEG-DSPE, ~2 mol % of the total lipids) is used to in the lipid bilayer as an anchor to bind photo-triggering gold nanorods through gold-thiol interactions. Thus this lipid mixture is in the solid phase when injected into the body and only when the gold couples with an external NIR light from a pulsed or continuous wave source heat is produced, which will induce a phase transition of the lipid bilayer (Troutman, et al., *Adv. Mater.*, 21 (22), 2334-2338 (2009); Volodkin, et al., *Angew. Chem., Int. Ed.*, 48 (10), 1807-9 (2009)) or be translated into pressure fluctuations that disrupt the lipid.

Formula II

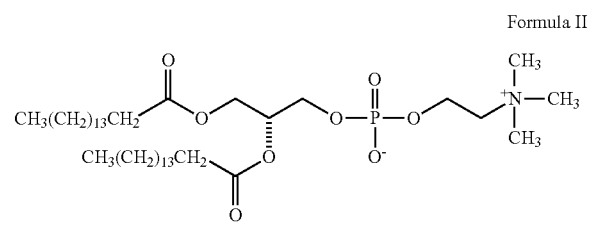

1,2-Dipalmitoyl-sn-glycero-3-phosphocholine (DPPC)

Formula III

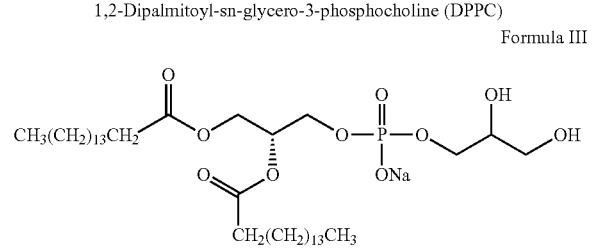

1,2 dipalmitoyl-sn-glycero-3-phospho-(1'-rac-glycerol) (DPPG)

Formula IV

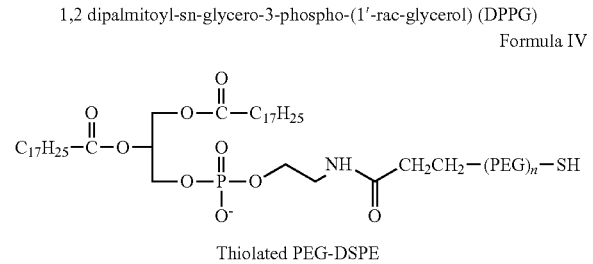

Thiolated PEG-DSPE

2. Polymeric Particles

By varying the polymer composition of the particle and morphology, one can effectively tune in a variety of controlled release characteristics. There have been a variety of materials used to engineer solid nanoparticles with and without surface functionality (as reviewed by Brigger et. al *Adv Drug Deliv Rev* 54, 631-651 (2002)). Perhaps the most widely used are the aliphatic polyesters, specifically the hydrophobic poly (lactic acid) (PLA), more hydrophilic poly (glycolic acid) PGA and their copolymers, poly (lactide-co-glycolide) (PLGA). The degradation rate of these polymers, and often the corresponding drug release rate, can vary from days (PGA) to months (PLA) and is easily manipulated by varying the ratio of PLA to PGA. Second, the physiologic compatibility of PLGA and its hompolymers PGA and PLA have been established for safe use in humans; these materials have a history of over 30 years in various human clinical applications including drug delivery systems. Finally, PLGA nanoparticles can be formulated in a variety of ways that improve drug pharmacokinetics and biodistribution to target tissue by either passive or active targeting.

Polymers

Non-biodegradable or biodegradable polymers may be used to form the microparticles. In the preferred embodiment, the microparticles are formed of a biodegradable polymer. Non-biodegradable polymers may be used for oral administration. In general, synthetic polymers are preferred, although natural polymers may be used and have equivalent or even better properties, especially some of the natural biopolymers which degrade by hydrolysis, such as some of the polyhydroxyalkanoates. Representative synthetic polymers are: poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivatized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulfate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups and other modifications routinely made by those skilled in the art.

Examples of preferred biodegradable polymers include polymers of hydroxy acids such as lactic acid and glycolic acid, and copolymers with PEG, polyanhydrides, poly(ortho)esters, polyurethanes, poly(butyric acid), poly(valeric acid), poly(lactide-co-caprolactone), blends and copolymers thereof.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the microparticles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG. In a preferred embodiment, PLGA is used as the biodegradable polymer.

Examples of preferred non-biodegradable polymers include ethylene vinyl acetate, poly(meth)acrylic acid, polyamides, copolymers and mixtures thereof.

Formation of Microparticles.

a. Solvent Evaporation/Emulsions.

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid microparticles. The resulting microparticles are washed with water and dried overnight in a lyophilizer. Microparticles with different sizes (0.5-1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

b. Hot Melt Microencapsulation.

In this method, the polymer is first melted and then mixed with the solid particles. The mixture is suspended in a non-miscible solvent (like silicon oil), and, with continuous stirring, heated to 5□C above the melting point of the polymer. Once the emulsion is stabilized, it is cooled until the polymer particles solidify. The resulting microparticles are washed by decantation with petroleum ether to give a free-flowing powder. Microparticles with sizes between 0.5 to 1000 microns are obtained with this method. The external surfaces of spheres prepared with this technique are usually smooth and dense. This procedure is used to prepare microparticles made of polyesters and polyanhydrides. However, this method is limited to polymers with molecular weights between 1,000-50,000.

c. Solvent Removal.

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microparticles from polymers with high melting points and different molecular weights. Microparticles that range between 1-300 microns can be obtained by this procedure. The external morphology of spheres produced with this technique is highly dependent on the type of polymer used.

d. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=−24□C, outlet temperature= 13-15 □C, aspirator setting=15, pump setting=10 mL/minute, spray flow=600 Nl/hr, and nozzle diameter=0.5 mm. Microparticles ranging between 1-10 microns are obtained with a morphology which depends on the type of polymer used.

e. Hydrogel Microparticles.

Microparticles made of gel-type polymers, such as alginate, are produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath for twenty to thirty minutes in order to allow sufficient time for gelation to occur.

Microparticle particle size is controlled by using various size extruders or varying either the nitrogen gas or polymer solution flow rates. Chitosan microparticles can be prepared by dissolving the polymer in acidic solution and crosslinking it with tripolyphosphate. Carboxymethyl cellulose (CMC) microparticles can be prepared by dissolving the polymer in acid solution and precipitating the microparticle with lead ions. In the case of negatively charged polymers (e.g., alginate, CMC), positively charged ligands (e.g., polylysine, polyethyleneimine) of different molecular weights can be ionically attached.

3. Microbubbles

In some embodiments, microbubbles are dispersed in solution with active agents or dispersed in suspension with liposomes or particles encapsulating active agents. During ultrasonic exposure, microbubbles vary in size in response to oscillation of acoustic waves and eventually burst to create shock waves to transiently open the tight junctions in nearby biological tissue. Meanwhile, active agents in the solution or released from liposomes or particles diffuse rapidly across the transiently opened junctions and permeate in tissues otherwise difficult to penetrate.

In some embodiments, microbubbles are coated or filled with medication (e.g., anesthetics), where ultrasonic shock waves activate the coating and cause mini explosions to release the medicine.

In some embodiments, the microbubbles have a gas core stabilized by a shell comprised of proteins, lipids or polymers. They are filled with an insoluble perfluorocarbon gas, such as perfluoromethane, perfluoroethane, perfluoropropane, perfluorobutane, or perfluoropentane. In one embodiment, the microbubbles are about 1 to about 15 microns in diameter.

The microbubbles may have a protein shell formed with albumin, lysozyme, and other amphipathic proteins which are highly surface active. Albumin-coated microbubbles can be formed by sonication of a heated solution (e.g., 5% (w/v)) of human serum albumin in the presence of air. During sonication, microbubbles of air are formed which become encapsulated within a nanometer-thick shell of aggregated albumin. Heating is necessary to denature the albumin prior to sonication and facilitate encapsulation, and the albumin shell is held together through disulfide bonds between cystein residues formed during cavitation.

Microbubbles may have a surfactant shell formed with mixtures of synthetic surfactants, such as SPAN-40® and TWEEN-40®. The SPAN®/TWEEN® mixture solution is sonicated in the presence of air to form stable microbubbles.

In preferred embodiments, the microbubbles have a lipid shell. Commercially available lipid-coated microbubble formulations may be used herein, including DEFINITY® (Lantheus Medical Imaging) and SONOVUE®® (Bracco Diagnostics). Phospholipids spontaneously self-assemble into a highly oriented monolayer at the air-water interface, such that their hydrophobic acyl chains face the gas and their hydrophilic headgroups face the water. The lipid molecules are held together by 'weak' physical forces, without chain entanglement, which makes the shell compliant to area expansion and compression during ultrasound insonification. Exemplary lipid molecules suitable for forming microbubbles are described above in the production of liposomes.

In other embodiments, microbubbles have a polymeric shell formed from cross-linked or entangled polymeric species, or polyelectrolyte multilayer shells. Exemplary polymeric-shelled microbubbles are described by Sirsi S and Borden M in *Bubble Sci Eng Technol,* 1(1-2):3-17 (2009).

4. Triggering Stimuli and Triggerable Elements

The triggerable elements can be sensitive to triggering stimuli such as light, heat or ultrasound. Exemplary heat triggerable elements include gold particles, which are sensitive to near-infrared (NIR) light; exemplary light triggerable systems include 1,4,8,11,15,18,22,25-octabutoxyphthalocyaninato-palladium(II), PdPc(OBu)$_8$; and exemplary sonosensitive triggerable elements include protoporphyrin IX.

i. UV, Visible and Near-Infrared (NIR) Light Triggering

Near-infrared (NIR) radiation has proven to be a promising tool for both in vivo imaging and photothermal cancer treatment. A key advantage to using light in the NIR window, approximately 650 nm-900 nm, is its minimal absorbance by skin and tissue. This window is bounded at the low end by the absorbance of hemoglobin and at the high end by the absorbance of water (Weissleder, *Nat. Biotechnol.,* 19, 316 (2001); Simpson, et al., *Phys. Med. Biol.,* 43, 2465 (1998)). Between these limits, light can penetrate tissue on the order of hundreds of micrometers to centimeters, enabling, for example, whole-body optical imaging. Nanoparticles have been developed that exhibit high absorption in the NIR range and have been used for photothermal drug release either alone or as components within polymer composites.

To enable the use of NIR-triggered systems in vivo, it is important to design materials and triggering systems that can be used safely, without injuring tissue. Such materials include, but are not limited to, gold nanoparticles such as gold nanorods, gold nanoshells and nanocages. In a particular embodiment, the triggerable elements are gold rods which are anchored to the liposomes.

In addition to NIR, UV- and visible-wavelength light have also been used to trigger drug delivery (Bawa, et al., *Biomed. Mater.,* 4 (2009)). Compared to longer wavelengths, light in the UV and visible regions suffers a number of drawbacks. It is strongly absorbed by skin and tissue and therefore cannot be used for deep-tissue triggering. Moreover, it will damage tissue at much lower powers than NIR. Nevertheless, tissues such as skin, the ear, or the back of the eye are excellent candidates for treatment, so long as the irradiation power is safe. Numerous chemical changes, such as bond cleavage and isomerization, can only be achieved with light in the UV or visible range.

In some embodiments, methods of triggerable release of drugs encapsulated within the liposomes typically involve a single administration of the composition liposomes to a subject, such as a human patient, followed by repeated and adjustable release by a safe external trigger such as NIR irradiation. Generally, the extent and timing of the exposure to NIR irradiation depends on the desired level and duration of pain relief. It is expected that the treatment cycles would be repeated as necessary.

To enable the use of NIR-triggered systems in vivo, it is important to design materials and triggering systems that can be used safely, without injuring tissue. The American National Standards Institute (ANSI) publishes maximum permissible exposures (MPEs) based on ocular irradiation. In the case of a light source that is not collimated (e.g., light emitted by a fiber optic cable, which spreads in a conical fashion), the MPE for 700 nm light from a continuous wave source is 200 mW/cm$^2$·steradian (sr) for long exposures or as high as 10 W/cm$^2$·sr for exposures no longer than a second in duration. For collimated light, acceptable levels are much lower: 0.2 mW/cm$^2$ for long exposures or 2 mW/cm$^2$ for exposures no longer than 1 s in duration. For longer wavelengths, higher power fluxes are permissible (American National Standards Institute, *American National Standard for the safe use of lasers,* ANSI Z136.1-1993. Laser Institute Orlando, Fla. (1993)). NIR-triggered materials have been triggered with continuous-wave power fluxes on the order of 0.1 to 10 W/cm$^2$. With ultrafast laser pulses, the MPE depends on pulse duration and pulse interval, as well as the wavelength of the light a. Plasmonic Resonance Noble metal nanoparticles can be irradiated at certain wavelengths so that their free metal electrons collectively oscillate in-phase with the electric field of the incident light, a phenomenon known as surface plasmon resonance (SPR). Hence, such particles are often termed plasmonic nanoparticles. Plasmonic nanoparticles can efficiently convert photon energy into heat by SPR (photothermal effect), allowing the disruption of non-covalent interactions. They can also convert photon energy to hot electrons such that weak covalent bonds (ex: Au—S bond) can be cleaved. Plasmonic nanoparticles, usually gold but sometimes silver, can produce heat and other plasmonic effects (such as hot electrons for covalent bond breaking) upon irradiation. Due to these effects, irradiation of these particles can induce drug release. The exact wavelength of irradiation is dependent on the shape and size of the nanoparticle, including gold nanoshells, gold nanorods, gold nanocages, gold nanostars, etc.

Gold Particles

Metallic nanostructures, and gold nanostructures in particular, are useful components in triggerable liposomes or particles because of their unique interactions with light. Under optical irradiation, free (conduction band) electrons in metals are driven to collectively oscillate in phase. This phenomenon, known as surface plasmon resonance (SPR), is pronounced in nanostructures because of their high surface-to-volume ratio. The exact shape and maximum of the extinction spectrum is highly dependent on particle size and shape, with larger particles generally exhibiting more red-shifted spectra, as determined experimentally and predicted by a form of Mie theory, with modifications by Gans (Link, et al., *Int. Rev. Phys. Chem.,* 19, 409 (2000); El-Sayed, *Acc. Chem. Res.,* 34, 257 (2001). In their excited state, electrons subsequently decay through either radiative (fluorescence), nonradiative (lattice rearrangement), or photothermal (local heating) pathways, where the specific pathway is dependent on the geometry of the nanoparticles and nature of the excitation pulse (Jain, et al., *J. Phys. Chem. B,* 110, 7238 (2006)). Lattice rearrangement and local heating, however, have been implemented in various modalities for triggered drug delivery. Gold nanoparticles have been synthesized in numerous morphologies, producing spheres, rods, cubes, shells, disks, and prisms, among other structures (Xia, et al., *Angew. Chem. Int. Ed.,* 48, 60 (2009)). Gold particles exhibit well-established surface chemistry, enabling facile functionalization with biologically relevant ligands (Wijaya, et al., *Langmuir*, 24, 9966 (2008); Love, et al., *Chem. Rev.*, 105, 1103 (2005);).

In some embodiments, the gold nanostructures are anchored to the liposomal surface via interaction with thiol group of thiolated PEG-DSPE (HS-PEG-DSPE, ~2 mol % of the total lipids) (Nanocs, PG2-DSTH) or thiolated polymers forming particles.

Gold Nanorods

Gold nanorods have been synthesized by electrochemical deposition in polycarbonate or alumina sacrificial templates, gold reduction in organic solvents, or by anisotropic elongation of gold seed particles in the presence of the cationic detergent, cetyltrimethylammonium bromide (CTAB), which acts as a stabilizer of gold nanorods. The last method is most widely employed since it can be used to produce large quantities of product with high monodispersity (Timko, et al., *Adv. Mater.*, 22(44):4925-43 (2010)). Nanorods and nanowires typically exhibit diameters on the order of 10-30 nm and lengths ranging from tens of nanometers (rods) to several micrometers (wires).

In some embodiments, gold nanorods with aspect ratios ranging from 1.5 to 10 for which the surface plasmon absorption maxima are between 600 and 1300 nm are synthesized by the seed-mediated growth method (Nikoobakht, et al., *Chem. Mater.*, 15, 1957-1962 (2003)).

Hexadecyltrimethylammoniumbromide (98%) (CTAB) and benzyldimethylammoniumchloride hydrate (98%) (BDAC), sodium borohydride (99%) ($NaBH_4$) and L-ascorbic acid can be purchased from Sigma (St, Louis, Mo.). For seed solution, the following steps are carried out: CTAB solution (5 mL, 0.20 M) is mixed with 5.0 mL of 0.00050 M $HAuCl_4$. To the stirred solution, 0.60 mL of ice-cold 0.010 M $NaBH_4$ is added, which results in the formation of a brownish yellow solution. Vigorous stirring of the seed solution is continued for 2 min. After the solution was stirred, it is kept at 25° C.

For nanorods with aspect ratios ranging from 1.5 to 4.5 (or plasmon bands less than 850 nm), CTAB (5 mL, 0.20 M) is added to (0.050, 0.10, 0.15, 0.20, 0.25 mL) of 0.0040 M $AgNO_3$ solution at 25° C. To this solution, 5.0 mL of 0.0010 M $HAuCl_4$ is added, and after gentle mixing of the solution 70 μL of 0.0788 M ascorbic acid is added. Ascorbic acid as a mild reducing agent changes the growth solution from dark yellow to colorless. It is worth noting that the five growth solutions above are identical except for their silver ion content. The final step is the addition of 12 μL of the seed solution to the growth solution at 27-30° C. The color of the solution gradually changes within 10-20 min. For longer NRs, the color change takes place more slowly. The temperature of the growth medium is kept constant at 27-30° C. in all the experiments. This pathway produces pure NR solutions with aspect ratios up to 4.7.

To grow longer NRs with aspect ratios ranging from 4.6 to 10 (or plasmon bands longer than 850 nm), a binary surfactant mixture composed of BDAC and CTAB is used. Two strategies can be used to grow longer NRs.

In the first approach the surfactant mixture can be prepared by adding 5 mL of 0.15 M BDAC to 0.010, 0.030, 0.050, 0.080, 0.10, 0.12, and 0.20 g of CTAB for making surfactant mixtures with ratios of 27 to 1.3. After dissolving the mixtures by sonication (20 min at 40° C.), each solution is added to 200 μL of 0.0040 M $AgNO_3$. In these solutions the silver content is kept constant while the fraction of the co-surfactant (CTAB) is changed. To this solution, 5.0 mL of 0.0010 M $HAuCl_4$ is added, and after gentle mixing of the solution 70 μL of 0.0778 M ascorbic acid is added. The growth process completes 1 h after addition of a 12-μL seed. At this stage NRs with aspect ratios of 5-5.5 are formed. By aging the NR solution for 7 days, the aspect ratio increases to 9-10. It has been found that the BDAC/CTAB ratios between 2 and 5.5 produce fewer spherical particles relative to the larger surfactant ratios. The color of the solution can change from red to light brown due to high or low concentration of NSs, respectively.

In the second approach, the growth solution with a BDAC/CTAB molar ratio of 2.7 is made as described above (called A). This ratio is selected because it favors the formation of fewer NSs relative to other ratios. The growth process is initiated after adding 12 μL of seed solution.

The growth solution (called B) is prepared by adding 5.0 mL of a mixture of 0.15 M BDAC and 0.10 g of CTAB to 200 μL of 0.0040 M $AgNO_3$. This solution is then added to 5.0 mL of 0.00050 M $HAuCl_4$ solution. To this solution, 36 μL of 0.0778 M ascorbic acid was added, which resulted in a colorless solution. The growth solution (B) is added to solution A at a rate of 1.0 mL per 20 min. Each addition of the growth solution red-shifts the plasmon band by about 20-30 nm. This process can be continued until the desired NR length is obtained.

Modifications of Gold Nanoparticles

To apply gold nanorods as medical nanodevices, biocompatible gold nanorods have been prepared by coating with phosphatidylcholine (Takahashi, et al., Langmuir., 22:2-5 (2006)) or by modifying gold nanorods with polyethylene glycol (PEG) (Niidome, et al., *J Control Release*, 114(3): 343-347 (2006)). PEG-modified gold nanorods show high dispersion stability, high circulation stability in the blood after intravenous injection into mice, and accumulation in tumors mediated by the enhanced permeability and retention (EPR) effect (Niidome, et al., *J Biomater Sci Polym Ed.*, 20:1203-1215 (2009); Akiyama, et al., *J Control Release.*, 139:81-84 (2009)). The PEG-modified gold nanorods have been applied to NIR imaging and photodynamic/photothermal therapy of tumors.

In some embodiments, PEGylation of GNRs is achieved by incubating with methoxy-PEG-thiol for 24 hours at room temperature and dialysis against deionized water for three days (Niidome, et al., *J Control Release*, 114(3):343-347 (2006)).

In the gold-conjugated liposomes mentioned below, the concentration of gold can be analyzed by inductively coupled plasma mass spectrometry (ICP-MS, Sciex Elan 6100, Perkin Elmer, Norwalk, Conn.). The GNR content in purified Lip-GNRs as measured by ICP-MS can range from 0.001-1 wt %. In some embodiments, the GNR content in purified Lip-GNRs as measured by ICP-MS is 0.02 wt %.

b. Heat Induced by Strong Absorption

Materials such as carbon nanotubes, photosensitizers, or organic dyes Graphene (Shi, Biomaterials 2013, 34, pp. 4786-4793), organic dyes (Spence, Chem. Sci., 2013, 4, 4240-4244) can absorb strongly at a certain wavelength of light to produce heat and induce liposomal structure change.

c. Photosensitization

Upon irradiation of photosensitizers, reactive oxygen species is produced and can trigger further chemical reactions for drug release (Van, et al., *Environ. Health Perspect.* 96, 177-184 (1991)).

Exemplary photosensitizing elements are 1,4,8,11,15,18, 22,25-octabutoxyphthalocyaninato-palladium(II), $PdPc(OBu)_8$, and the platinum analogue $PtPc(OBu)_8$.

In a particular embodiment, the phototriggering agent is $PdPc(OBu)_8$. Irradiation of $PdPc(OBu)_8$ in the NIR range e.g. 730 nm can lead to peroxidation of liposomal lipids, thus increases the permeability of the lipid bilayer and allows the release of encapsulated content.

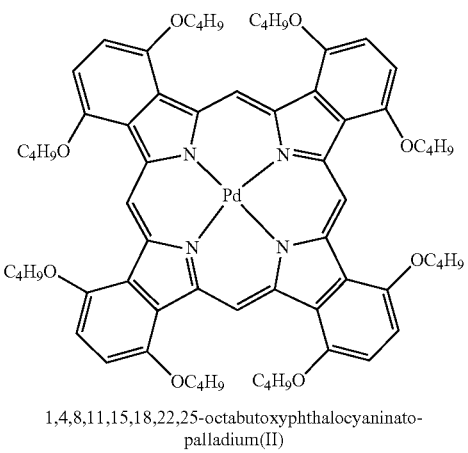

Formula I 1,4,8,11,15,18,22,25-octabutoxyphthalocyaninato-palladium(II)

d. Photocleavage

Photocleavage occurs when a covalent bond is broken upon light irradiation. Photocleavage has been widely employed in light-induced drug delivery. For example drug molecules can be directly bound to a carrier by photocleavable linkers (the photolabile moiety is part of the linker). Upon UV irradiation, the linkers are cleaved and the drug molecules are released. Alternatively, photolabile groups can be incorporated into the drug carrier itself. Upon UV exposure, the groups are cleaved, which partially or completely disrupts the integrity of the drug carrier, causing the therapeutic content to be released. O-nitrobenzyl and coumarin derivatives, can be non-reversibly cleaved upon irradiation, are commonly used in photocleavage-based drug delivery e. Photoisomerization Drugs can be released from carriers by the reversible isomerization of molecules upon irradiation with near-UV and visible light. Such photoisomerization reactions may involve azobenzenes, which contain two phenyl groups joined by an N=N bond. These molecules respond to UV light in the range of 300-400 nm with a transition from trans to cis, whereas heat or exposure to light with a wavelength above 400 nm reverses this process. Such chemistry has been used to create a molecular valve.

Liposomes have been made with lipids containing azobenzenes groups, which can cause photo-induced, reversible conformational changes in their structure. For example, liposomes containing cholesterol derivatives with azobenzene moieties could be induced to release drugs by UV light, whereas visible light completely stopped release (Liu, et al., *Biochim. Biophys. Acta,* 1720, 28 (2005)).

Another example of photoisomerizable groups is spiropyran. Spiropyran has been used to bind to the hydrophobic terminus of a single chain lipid, which can be incorporated into DPPC-based liposomes at up to 10% loading. Photoisomerization of spiropyran (hydrophobic) to merocyanine (hydrophilic) by a ring-opening reaction destabilized the bilayer membrane, increasing liposome permeability (Ohya, et al., *Supramol. Sci.* 5, 21-29 (1998)).

f. Photocrosslinking

Photocrosslinking (light induced polymerization) has been used as means to stabilize therapeutic nanocarriers such as liposomes (Lawson, et al., *Langmuir* 19, 3557-3560 (2003); Regen, et al., *Biochem. Biophys. Res. Commun.* 101, 131-136 (1981)) and nanocapsules (Lawson, et al., *Langmuir* 19, 6401-6407 (2003)). Photocrosslinking can be used to destabilize the structure and induce defects Puri and coworkers have reported on light-triggerable liposomes prepared from a photo-polymerizable phospholipid DC8, 9PC (1,2-bis(tricosa-10,12-diynoyl)-sn-glycero-3-phosphocholine) and DPPC (1,2-dipalmitoyl-sn-glycero-3-phosphocholine). Upon UV exposure (254 nm), the photocrosslinking of DC8, 9PC led to the formation of defects in the liposome bilayer resulting in lateral membrane expansion/destabilization and therefore release of the therapeutic content (Puri, Pharmaceutics 6, 1-25 (2014)).

Reversible crosslinking of photoactive moieties such as coumarin and thymine has been used to control the stability of the nanocarrier and consequently their content release. The photodimerization of coumarin or thymine, a UV induced $2\pi+2\pi$ photocyclization, results in the covalent dimerization of adjacent molecules (Trenor, et al., *Chem. Rev.* 104 3059-3078 (2004); Saito, et al., *Chem. Commun.* 2503-2505 (2007)).

g. Photo-Induced Rearrangement

Excited molecules may also undergo rearrangement reactions such as the Wolff rearrangement. The Wolff rearrangement of an α-diazocarbonyl yields a ketene as an intermediate product, which can react with weak acidic nucleophiles such as water, an alcohol or an amine to generate carboxylic acid derivatives or undergo [2+2] cyclo-addition to form four-membered ring (Kirmse, *Eur. J. Org. Chem.* 2193-2256 (2002)). Wolff rearrangement can be induced by heat, transition metals, or UV light. For example, 2-Diazo-1,2-naphthoquinones (DNQ) (hydrophobic) undergoes UV-induced Wolff rearrangement to produce 3-indenecarboxylic acid (hydrophilic) resulting in a marked change in water solubility.

Frechet and coworkers have incorporated DNQ in the hydrophobic end of a PEG-lipid amphiphile. Micelles made out of this material were able to form and encapsulate a fluorophore probe (Nile Red). Upon UV irradiation (350 nm), DNQ was converted to 3-indenecarboxylate, changing the amphiphilic property of the core-forming segment, destroying the micelles and releasing the encapsulated fluorophore (Goodwin, et al., *J. Am. Chem. Soc.* 127, 9952-9953 (2005)).

ii. Ultrasound

In some embodiments the triggerable elements are elements that cause liposomal or particle release or a burst of microbubbles to create shock waves to transiently open the tight junctions in nearby biological tissue in response to ultrasound.

Ultrasound is a longitudinal pressure wave with frequency above 20 kHz (Lentacker, et al., *Soft Matter,* 5, 2161 (2009)). It has been used in a wide range of medical applications including tissue ablation, kidney stone shattering, imaging, liposuction, and transdermal drug delivery (Schroeder, et al., *Chem. Phys. Lipids.,* 162 (2009)). Its use in drug delivery has evolved from releasing drugs entrapped in a degradable polymer matrix (Kost, et al., *Proc. Natl. Acad. Sci,* 86, 7663 (1989)) to including many drug delivery modalities, including transdermal drug delivery (sonophoresis) (Ogura, et al., *Adv. Drug Delivery Rev.,* 60, 1218 (2008)), and releasing from numerous drug carriers, such as liposomes, polyelectrolyte microcontainers, multilayered capsules, micelles, microbubbles, or polymers, by either thermal or nonthermal mechanisms (Ferrara, *Adv. Drug Delivery Rev.,* 60, 1097 (2008)).

Ultrasound is defined as sound at a frequency of between 20 kHz and 10 MHz, with intensities of between greater than 0 and 3 W/cm². Ultrasound is preferably administered at frequencies of less than or equal to about 2.5 MHz to induce cavitation to enhance transport. Ultrasound can be divided into two main categories: low frequency ultrasound (LFUS), which ranges between 20 and 100 kHz, and high frequency ultrasound (HFUS), which exceeds 1 MHz. LFUS has been used to induce sonophoresis and affects drug carriers such as liposomes, inducing drug release. HFUS has been used to trigger oscillations in micro-bubbles and exhibits the added benefit that it may be focused. Ultrasound can be applied continuously or in pulses. Low intensity ultrasound (0.1-100 mW/cm² or 0.0001-0.1 W/cm²) is often used for diagnostic imaging and is also likely below spontaneous cavitation threshold. (Dubinsky T J, et al., *Am J Roentgenology*, 190(1): 191-199 (2008)).

Preferably the ultrasound energy is administered at a frequency of about 0.5- to about 5 MHz, and sufficient to cause rupture of the microbubbles within the patient's target site of delivery of active agents. The amount of ultrasonic energy applied is adjusted so that it is sufficient to degrade, burst, disrupt or break apart the microbubbles without causing undesired irreversible damage (e.g., heat damage) to the biological tissue or damage to the activity of active agents encapsulated, associated, or co-delivered with the microbubbles.

Many ultrasound devices are available commercially which can be used in the method described herein. For example, the ultrasonic devices used by dentists to clean teeth have a frequency of between about 25 and 40 KHz. Commercially available portable ultrasound tooth-brushes make use of a small sonicator contained within the toothbrush (Sonex International Corporation). This sonicator is portable and operates on rechargeable batteries. The devices may optionally include a reservoir for an ultrasound gel, which will typically have a sound coefficient like water, or a reservoir for collecting analyte.

The physical effect of ultrasound on liposomes, particles, and microbubbles includes ultrasound-induced heat and mechanical displacement.

Ultrasound causes heating when a fraction of propagating energy is absorbed by the tissue or drug carrier, triggering release from temperature-sensitive vehicles. In some circumstances mechanical displacements can result in the nucleation, growth, and collapse of gas bubbles, a process referred to as cavitation, which disrupts liposomal membrane to induce drug release or burst of microbubbles (Wu, et al., *Adv. Drug Delivery Rev.*, 60, 1097 (2008)). See also Epstein-Barash, et al: A microcomposite hydrogel for repeated on-demand ultrasound-triggered drug delivery. Biomaterials 2010; 31: 5208-17.

a. Sonosensitizers

In some embodiments the triggerable elements are sonosensitizers. Sonosensitizers which produce reactive oxygen species upon ultrasound, can also be used to induce chemical reactions for disrupting the liposomal membrane. Sonosensitizers can be encapsulated or loaded in liposomes, particles, or microbubbles. Exemplary sonosensitizers include protoporphyrin IX (PPIX) or a porphyrin derivative. Sonosensitizers generally generate reactive oxygen species (ROS) including singlet oxygen and free radicals by sonication, and therefore agents such as doxorubicin can also be used as a sonosensitizer.

Other sonosensitizers include those that self-assemble to form aggregates when exposed to ultrasound.

b. Ultrasound Cleavable Bonds

In some embodiments the triggerable elements include Ultrasound Cleavable Bonds. See, for example, Xuan, Langmuir, 2012, 28, 16463-16468 Ultrasound cleavable bonds can also be introduced to liposomes for chemical disruption to induce drug release.

c. Mechanophores

In some embodiments the triggerable elements include mechanophores. A mechanophore is any chemical entity that possesses mechanically labile bonds; that is, a functional group that changes under the influence of exogenous mechanical forces (Brantley, et al., *Polymer International*, 62 (1), 2-12 (2013)). Mechanochemical responses can range from isomerizations (e.g. configurational or constitutional) to precise bond scission events. Ultrasound, which is capable of generating substantial tensile stresses within solvated polymer chains, has proven to be a particularly efficient energy source for activating mechanophores (Caruso, et al. *Chem. Rev.*, 109:555 (2009); Black, et al., *J. Mater. Chem.*, 21:1655 (2011); Suslick, et al., *Annu. Rev. Mater. Sc.*, 105:2921 (1999)).

iii. Magnetic Triggering

In some embodiments, the triggerable elements are elements that cause liposomal or particular release in response to Magnetic triggering. Exemplary triggerable elements that cause liposomal release in response to Magnetic triggering are superparamagnetic nanoparticles.

Superparamagnetic nanoparticles are incorporated into the interior of liposomes or particles so that the release of the encapsulated content can be controlled under magnetic field guidance. Local heating effects from oscillating magnetic field on magnetically active nanoparticles can be used to actuate permeability of liposomes (Timko, et al., *Adv. Mater.* 22 (44), 4925-43 (2010)).

5. Agents to be Delivered

The liposomes or particles are used to provide anesthesia by releasing a site I sodium channel blocker, by enhancing the adjustability and repeatability of the release of site I sodium channel blockers in lowering required energy, prolonging nerve block duration, and/or increasing the efficiency of released S1SCBs, or by enhancing the efficacy of conventional anesthetics. Other therapeutic, prophylactic or diagnostic agents may also be delivered. However, as demonstrated by the examples, only the site I sodium channel blockers are effective in providing anesthesia using the triggerable release liposomes or particles.

The liposomes or particles can encapsulate different drugs that target the same site to elicit the same or different response in the subject. Typically, the type and number of active agents encapsulated within the liposomes or particles do not alter the release kinetics.

i. Site 1 Sodium Channel Blockers

Site 1 Sodium Channel blockers (S1SCB) are a family of molecules long recognized for their potent and specific blockade of voltage gated sodium channels.

Site 1 sodium channel blockers bind to what is known as site 1 of the fast voltage-gated sodium channel. Site 1 is located at the extracellular pore opening of the ion channel. The binding of any molecules to this site will temporarily disable the function of the ion channel. S1SCBs include phycotoxins (saxitoxin (STX), decarbamoyl saxitoxin, neosaxitoxin, and the gonyautoxins), tetrodotoxin (TTX) and several of the conotoxins.

a. Tetrodotoxin

Tetrodotoxin (TTX) is a highly potent neurotoxin that blocks the fast Na+ current in human myocytes (the contractile cells of the muscles), thereby inhibiting their contraction. Chemically, it is an amino perhydroquinaoline (see *Pharmacological Reviews*, 18 (2) 997-1049 (1966)).

Tetrodotoxin alone is too toxic to be used as an anesthetic. Combinations of tetrodotoxin with bupivacaine produced long duration sciatic nerve blockade in rats without increased systemic toxicity compared to tetrodotoxin alone (Kohane, et al., *Anesthesiology*, 1998:119-131). Although the potent inhibition of voltage-gated Na+ channels is too hazardous for TTX to be used as a drug alone, blocking such channels in a controlled fashion may be desirable in the treatment of conditions such as Parkinson's disease and chronic pain in terminally ill cancer patients.

Formula V

Chemical structure of Tetrodotoxin(C11H17N3O8)

Tetrodotoxin has been isolated from animals, such as the blue-ringed octopuses, and is produced by bacteria. The most common bacteria associated with TTX production are *Vibrio* Sp. bacteria, with *Vibrio alginolyticus* being the most common species. Tetrodotoxins can be obtained from the ovaries and eggs of several species of puffer fish and certain species of California newts.

Numerous schemes for the total chemical synthesis of Tetrodotoxin has also been reported, including by Diels-Alder Reactions or Syntheses of TTX from Carbohydrates and Congeners (Ohyabu, et al., J Am Chem Soc. July 23; 125(29): pp 8798-805 (2003)); Nishikawa, et al., Angew. Chem. Int. Ed., 43, 4782. DOI: 10.1002/anie.200460293 (2004); reviewed in Chau and Ciufolini, Mar Drugs, 9(10): 2046-2074 (2011)). Synthesis features rapid construction of the cyclohexene by Diels-Alder cycloaddition using an enantiomerically-pure dienopile, the early introduction of the aminated quaternary center, and the use of that center to direct the relative configuration of further functionalization around the ring.

b. Phycotoxins

Phycotoxins act as a specific blocker of the voltage-dependent sodium channels present in excitable cells (Kao, C. Y., *Pharm. Rev.*, 18(2): 997-1049 (1966)). Due to the inhibition of sodium channels, the transmission of a nervous impulse is blocked and the release of neurotransmitters is prevented at the level of the neuromotor junction, which prevents muscular contraction.

The chemical structure of these phycotoxins has a general structure of Formula VI:

Formula VI

General chemical structure of the phycotoxins

The particular chemical structure of the structure is defined by the substituents R1 to R5 according to the Table 1:

TABLE 1

Chemical Structures of Phycotoxins relative to the Formula VI

| Compound | R1 | R2 | R3 | R4 | R5 |
|---|---|---|---|---|---|
| Saxitoxin | H | H | H | COONH$_2$ | OH |
| Neosaxitoxin | OH | H | H | COONH$_2$ | OH |
| Gonyaulatoxin 1 | OH | H | OSO$^{-3}$ | COONH$_2$ | OH |
| Gonyaulatoxin 2 | H | H | OSO$^{-3}$ | COONH$_2$ | OH |
| Gonyaulatoxin 3 | OH | OSO$^{-3}$ | H | COONH$_2$ | OH |
| Gonyaulatoxin 4 | H | OSO$^{-3}$ | H | COONH$_2$ | OH |
| Gonyaulatoxin 5 | H | H | H | COONHSO$^{-3}$ | OH |

(A). Saxitoxin

Saxitoxin (STX) was first extracted from the Alaska butterclam, *Saxidomus gigantcus*, where it is present in algae of the genus Gonyaulax. The reported chemical formula is C$_{10}$ H$_{15}$ N$_7$ O$_3$.2HCl. It is freely soluble in water and methanol and it is believed the toxin has a perhydropurine nucleus in which are incorporated two guanidinium moieties.

Neosaxitoxin and Decarbamoyl Saxitoxin

Neosaxitoxin and decarbamoyl saxitoxin are potentially more potent and may have advantages over saxitoxin in formulation. Neosaxitoxin (NeoSTX) is under clinical development as a prolonged duration local anesthetic (Rodriguez-Navarro, et al., Anesthesiology, 2007; 106:339-45; Rodriguez-Navarro, et al., Neurotox. Res., 2009; 16:408-15; Rodriguez-Navarro, et al., Reg. Anesth. Pain Med., 2011; 36:103-9). A Phase 1 study of subcutaneous infiltration in human volunteers showed that NeoSTX caused effective cutaneous hypoesthesia (Rodriguez-Navarro, et al., Anesthesiology, 2007; 106:339-45) and a second Phase 1 study showed that combination with bupivacaine resulted in more prolonged analgesia compared to NeoSTX or bupivacaine alone (Rodriguez-Navarro, et al., Neurotox. Res., 2009; 16:408-15). Specific formulations are currently under development and further clinical testing. See U.S. Pat. Nos. 8,975,281 and 8,975,268.

Saxitoxin (STX) and its derivatives can be produced in bioreactors from algae. The phycotoxins neosaxitoxin, saxitoxin and gonyaulatoxins are active compounds produced by harmful algae blooms of the genera *Alexandrium* sp., *Piridinium* sp., and *Gimnodinium* sp., (Lagos, *N. Biol. Res.*, 31: 375-386 1998)). In the last 15 years, it has been demonstrated that these phycotoxins can also be produced by fresh water cyanobacteria such as photosynthetic blue-green algae, besides being produced by marine dinoflagellates.

Only four genera of cyanobacteria able to produce paralyzing phycotoxins have been identified, and each produces a different mixture of phycotoxins both in amounts and in types of phycotoxins produced, i.e. they produce different profiles of paralyzing phycotoxins (Lagos, et al., 1999, *TOXICON,* 37: 1359-1373 (1999). Pereira, et al., *TOXICON,* 38: 1689-1702 (2000).

STX can also be produced by chemical synthesis according to at least three distinct methods (Kishi, et al., *J. Am. Chem. Soc.,* 98, 2818 (1977)); Jacobi, et al., *J. Am. Chem. Soc.,* 106 (19), pp 5594-5598 (1984) Fleming, et al., *J. Am. Chem. Soc.,* 3926 (2006)).

ii. Alpha-2-Adrenergic Agonists

Alpha-2-adrenergic agonists ($\alpha_2$-adrenergic agonists) are known to those skilled in the art. See, for example, The Pharmacological Basis of Therapeutics, 8th Edition, Gill, A. G., T. W. Rall, A. S. Nies, P. Taylor, editors (Pergamon Press, Co., Inc., NY 1990).

In some embodiments, agents with alpha-2 adrenoceptor agonist activity are represented by Formula VII:

Formula VII

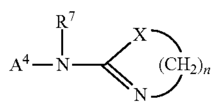

In certain embodiments, $A^4$ may be selected from aryl, and heteroaryl, which may be substituted by one or more radicals selected from alkyl, branched alkyl, cycloalkyl, hydroxyl, alkoxy, cycloalkylalkyl, alkoxyalkyl, aryl, alkanoyl, alkoxycarbonyl, carboxyl, amino, cyano, halogen, thioalkyl, dialkylamino, arylamino, alkylsulfinyl, alkylsulfonyl, arylsulfinyl or arylsulfonyl; wherein X is selected from thio, imino, or methylene; wherein $R^7$ is selected from hydrogen, lower alkyl, or oxygen-containing heterocycle; and n is either 2 or 3; or a pharmaceutically acceptable salt thereof.

A preferred class of compounds of Formula VII consists of those compounds wherein $A^4$ is phenyl; wherein $A^4$ is substituted phenyl, on which positions 2 and 6 of the phenyl ring may be independently substituted by a radical selected from hydrogen, chloro, methyl, ethyl, or cycloalkyl, and positions 3, 4, and 5 may be independently substituted by a radical selected from hydrogen, methyl, trifluoromethyl, fluoro, or cyano; wherein $A^4$ is 3-thienyl, on which positions 2 and 4 are independently substituted by a radical selected from hydrogen, chloro, methyl, ethyl, or cycloalkyl; wherein $A^4$ is 1-naphthyl, 5,6,7,8-tetrahydronaphthyl-1-yl, pyrrolyl, oxazolyl, isoxazolyl, indol-3-yl, indazol-3-yl, quinolinyl, quinazolinyl, quinoxazolinyl, benzoxazolyl, and benzothiophen-3-yl; wherein $A^4$ is pyrimidin-4-yl, on which positions 3 and 5 are independently substituted by hydrogen, chloro, methyl, ethyl, cycloalkyl, or methoxy; wherein $R^7$ is either hydrogen or tetrahydropyran-2-yl; wherein X is thio or imino; and wherein n is 2.

An especially preferred class of compounds of Formula VII consists of compounds wherein $A^4$ is selected from phenyl, 2,6-dichlorophenyl, 2,6-dimethylphenyl, 2,6-diethylphenyl, 3,4-dihydroxyphenyl, 3-fluoro-6-methylphenyl, 2-chloro-5-trifluoromethylphenyl, 2-chloro-4-methylphenyl, 3-chloro-4-methylthien-3-yl, 5,6,7,8-tetrahydronaphth-1-yl, and 4-chloro-5-methoxy-2-methylpyrimidin-4-yl; wherein $R^7$ is hydrogen or tetrahydropyran-2-yl; wherein X is thio or imino; and wherein n is 2.

A specifically preferred class of compounds of Formula VII consists ofxylazine, flutonidine, moxonidine, tramazoline, tolonidine, piclonidine, tiamenidine, clonidine and dexmedetomidine.

a. Dexmedetomidine

In a particular embodiments, the Alpha-2-adrenergic agonist is Dexmedetomidine (DMED), also known as (S)-4-[1-(2,3-Dimethylphenyl)ethyl]-3H-imidazole, marketed as PRECEDEX™.

Formula VIII

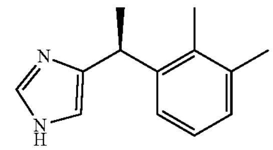

Dexmedetomidine (C13H16N2)

Dexmedetomidine is often used as an intravenous sedative medication in intensive care units. It has a half-life of approximately 2 hours. Side effects of Dexmedetomidine are associated with peripheral $\alpha$2-receptor stimulation, resulting in hypotension (low blood pressure) and bradycardia.

DMED is also believed to block hyperpolarization-activated nonselective cation channels (HCN channels).

In some embodiments, the $\alpha_2$-adrenergic agonists is DMED.

b. Clonidine

Another alpha-2-adrenergic agonist is Clonidine (CLD), also known as N-(2,6-dichlorophenyl)-4,5-dihydro-1H-imidazol-2-amine, and marketed as CATAPRES™. The principle side effects associated with clonidine are sedation, dry mouth, and hypotension (low blood pressure).

Formula IX

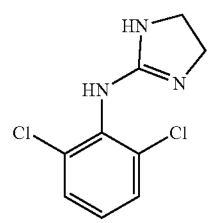

Clonidine (C9H9Cl2N3)

c. Derivatives and Analogs of $\alpha_2$-Adrenergic Agonists

Although described above with reference specific to compounds, one can also utilize enantiomers, stereoisomers, metabolites, derivatives and salts of the active compounds. Methods for synthesis of these compounds are known to those skilled in the art. Examples of pharmaceutically acceptable salts include, but are not limited to, mineral or organic acid salts of basic residues such as amines, and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Conventional non-toxic salts include those derived from inorganic acids such as hydrochloric, hydrobromic, sulfuric, sulfamic, phosphoric and nitric acid; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic and isethionic acids. The pharmaceutically acceptable salts can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed. (Mack Publishing Company, Easton, Pa., 1985, p. 1418).

A prodrug is a covalently bonded substance which releases the active parent drug in vivo. Prodrugs are prepared by modifying functional groups present in the compound in such a way that the modifications are cleaved, either in routine manipulation or in vivo, to yield the parent compound. Prodrugs include compounds wherein the hydroxy or amino group is bonded to any group that, when the prodrug is administered to a mammalian subject, cleaves to form a free hydroxyl or free amino, respectively. Examples of prodrugs include, but are not limited to, acetate, formate and benzoate derivatives of alcohol and amine functional groups.

A metabolite of the above-mentioned compounds results from biochemical processes by which living cells interact with the active parent drug or other formulas or compounds of the present invention in vivo. Metabolites include products or intermediates from any metabolic pathway.

iii. Conventional Local Anesthetics

As used herein, the term "conventional local anesthetic" means a drug which provides local numbness or pain relief and includes following classes of local anesthetics: the aminoacylanilide compounds such as lidocaine, prilocaine, bupivacaine, mepivacaine and related local anesthetic compounds having various substituents on the ring system or amine nitrogen; the aminoalkyl benzoate compounds, such as procaine, chloroprocaine, propoxycaine, hexylcaine, tetracaine, cyclomethycaine, benoxinate, butacaine, proparacaine, and related local anesthetic compounds; cocaine and related local anesthetic compounds; amino carbonate compounds such as diperodon and related local anesthetic compounds; N-phenylamidine compounds such as phenacaine and related anesthetic compounds; N-aminoalkyl amid compounds such as dibucaine and related local anesthetic compounds; aminoketone compounds such as falicaine, dyclonine and related local anesthetic compounds; and amino ether compounds such as pramoxine, dimethisoquien, and related local anesthetic compounds. The preferred local anesthetics are amino-amides and amino esters, with the most preferred being bupivacaine, the levoenantiomer of bupivacaine being preferred where vasoconstrictor activity of the local anesthetic is desirable, tetracaine, and ropivacaine, which is slightly more sensory selective.

These drugs average six to ten hours of pain relief when given in different sites and for different types of surgery. For many types of surgery, it would be preferable to have durations of pain relief that last two or three days. The preferred local anesthetics for use in combination with NeoSTX are bupivacaine, ropivacaine, tetracaine and levobupivacaine. Bupivacaine is a particularly long acting and potent local anesthetic. Its other advantages include sufficient sensory anesthesia without only partial motor blockade, and wide availability.

iv. Vasoconstrictors

Vasoconstrictors which are useful are those acting locally to restrict blood flow, and thereby retain the injected drugs in the region in which they are administered. This has the effect of substantially decreasing systemic toxicity. Preferred vasoconstrictors are those acting on alpha adrenergic receptors, such as epinephrine and phenylepinephrine. Other drugs and dyes vasoconstrict as a side-effect, such as bupivacaine and levobupivacaine.

B. Excipients and Devices

The compositions for local anesthetics that elicit repeatable and adjustable on-demand nerve blockade can be administered and taken up a subject with a delivery vehicle. In a preferred embodiment, the anesthetic is delivered by injection locally. Typical carriers are saline, phosphate buffered saline, and other injectable carriers.

Formulations of triggerable release liposomes encapsulating one or more site 1 sodium channel blockers, optionally in combination with alpha-2-adrenergic agonists are disclosed. Pharmaceutical compositions can be formulated for different mechanisms of administration, according to the inhibitor and the intended use.

Pharmaceutical compositions formulated for administration by parenteral (intramuscular, intraperitoneal, intravenous (IV) or subcutaneous injection), and topical routes of administration are disclosed.

1. Topical Administration

The active agent and optional delivery vehicle can be applied topically. Topical administration can include application directly to exposed tissue, vasculature or to tissues or prostheses, for example, during surgery, or by direct administration to the skin or tissue.

Transdermal formulations may also be prepared. These will typically be ointments, lotions, sprays, or patches, all of which can be prepared using standard technology. Transdermal formulations can include penetration enhancers. Standard pharmaceutical excipients for topical or transdermal administration are available from any formulator.

2. Mucosal Administration

Formulations for administration to the mucosa, such as the mouth, eyes, nasal, oral (sublingual, buccal), vaginal, or rectal mucosa, will typically be spray dried drug particles, which may be incorporated into a tablet, gel, capsule, suspension or emulsion. Standard pharmaceutical excipients are available from any formulator.

3. Parenteral Administration

In some embodiments, the formulation are formulated in an aqueous solution, for parenteral injection. The formulation may be in the form of a suspension or emulsion. In general, pharmaceutical compositions are provided including effective amounts of an active agent, targeting moiety, and a delivery vehicle and optionally include pharmaceutically acceptable diluents, preservatives, solubilizers, emulsifiers, adjuvants and/or carriers. Such compositions include the diluents sterile water, buffered saline of various buffer content (e.g., Tris-HCl, acetate, phosphate), pH and ionic strength and optionally additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

4. Preservatives

The formulations may also contain preservatives, pH adjusting agents, antioxidants, and isotonicity agents.

In the preferred embodiment the anesthetic is formulated in saline, or an acidic buffered solution, optionally containing a preservative. Local or sustained release carriers may be utilized, but are not preferred.

5. Chemical Permeation Enhancers

The formulation and method herein for controlled, high-efficiency, prolonged anesthesia may optionally include the application of CPEs.

Chemical permeation enhancers (CPEs) can improve access of local anesthetics to the nerve, thereby improving nerve block performance. There are at least three sub-groups of CPEs, anionic, cationic, and nonionic surfactants. CPEs are associated with some in vitro myotoxicity, but they improve the frequency and duration of nerve block with selective anesthesics (Emmanuel J S, et al., *Mol Pharm*, 6(1):265-273 (2009)). Exemplary CPEs include agents described in U.S. Pat. No. 8,658,699.

C. Dosage Units

In preferred embodiments, the site 1 sodium channel blockers is administered in combination with an alpha-2-adrenergic agonist encapsulated in photo-triggerable liposomes and/or other excipients are provided in vials in an aqueous solution. Depending on the type of formulation, as outlined previously and below, the vial sizes may range from 1-40 mls, and 1-3 vials may be used for a single patient in different situations. In another embodiment, the site 1 sodium channel blockers in combination with alpha-2-adrenergic agonists, encapsulated in photo-triggerable liposomes and/or other excipients are provided in one or more vials, optionally lyophilized, then rehydrated and combined prior to use. For this second embodiment, preferred vial sizes could range from 5-40 mls.

III. Methods of Use

Methods of repeated on-demand or single injection with prolonged anesthesia over extended periods with minimal toxicity are provided. Methods involve one or more administrations of the formulation to a subject such as human patients, followed by one or more exposures to a safe external trigger such as NIR irradiation and ultrasound depending on the desired level and duration of pain relief. It is expected that the treatment cycles would be repeated as necessary.

The compositions for prolonged local anesthesia can be administered by any means known in the art, including via injection to a discrete site through the skin of a human or animal; via implantation to a discrete site by embedding the dose into the skin, tissue, muscles, tendons, joints, or other body parts of a human or animal; by infiltration into a discrete wound, tissue surface or surgical site where the surgical wound is open.

In some embodiments, the method steps include (a) administering to a subject an effective amount of liposomes or particles encapsulating one or more site 1 sodium channel blockers, optionally one or more alpha-2-adrenergic agonists, and one or more triggerable elements; (b) applying a triggering agent such as light, ultrasound and magnetic field, to the subject to allow release of sufficient amount of active agents from the liposomes for pain relief; (c) optionally removing the triggering source to prevent further release once the level of pain relief is achieved; (d) repeating steps (b)-(c) to allow further triggered drug release at patient/medical practitioner's discretion. The methods can be effective for at least four separate triggering events and can last for up to five or more days following a single application.

In other embodiments, the method steps include administering to a subject an effective amount of one or more sodium channel blockers including site 1 sodium channel blockers, optionally one or more alpha-2-adrenergic agonists, and microbubbles; and applying a triggering stimulus such as ultrasound to the subject to induce rapid permeation of drugs, where ultrasound and microbubbles create shock waves and disrupt tight junctions.

Contacting one or more nerves with an effective amount of a site 1 sodium channel blockers in combination with one or more $\alpha_2$-adrenergic agonists decreases or inhibits sensory activity in the nerves compared to a control. In some embodiments, the methods prolong the blockade of hyperpolarization-activated nonselective cation channels (HCN channels) with minimal or reduced toxicity.

In some embodiments the additional active agents stimulate a response from the adrenergic receptors. In a preferred embodiment the additional active agent is Dexmedetomidine. Methods including contacting one or more nerves with an effective amount of a site 1 sodium channel blockers in combination with alpha-2-adrenergic agonists to decrease or inhibit sensory activity in the nerves compared to a control are provided. The methods can block hyperpolarization-activated nonselective cation channels (Ih channels) and simultaneously stimulate a response from the adrenergic receptors to prolong the anesthetic effect of site 1 sodium channel blockers relative to site 1 sodium channel blockers administered alone. Typically, the methods do not give rise to vasoconstriction.

The term "combination" or "combined" is used to refer to either concomitant, simultaneous, or sequential administration of the two or more agents. Therefore, the combinations can be administered either concomitantly (e.g., as an admixture), separately but simultaneously (e.g., via separate applications into the same subject), or sequentially (e.g., one of the compounds or agents is given first followed by the second). Therefore, the combination therapy can include co-administration of the site 1 sodium channel blockers with alpha-2-adrenergic agonists separately in two different formulations, or together in the same formulation (i.e., a single pharmaceutical composition including both active agents). If the two agents are administered in separate formulations, co-administration can include the simultaneous and/or sequential administration of the two agents. An appropriate time course for sequential administration can be chosen by the physician, according to such factors such as the nature of a patient's illness, and the patient's condition. In certain embodiments, sequential administration includes the co-administration of the two agents within a period of hours, days, or weeks of one another. In some embodiments the site 1 sodium channel blocker is administered first, followed by the in combination with alpha-2-adrenergic agonist. In other embodiments the alpha-2-adrenergic agonist is administered first, followed by the site 1 sodium channel blocker.

1. Dosages

One or more site 1 sodium channel blockers, optionally in combination with alpha 2 adrenergic agonists, encapsulated in triggerable liposomes or particles can be administered at a discrete painful site in an amount effective to produce a selective, highly-localized blockade of hyperpolarization-activated nonselective cation channels and/or simultaneously stimulate a response from the adrenergic receptors in a discrete, localized area responsible for the initiation of pain for the purpose of reducing or eliminating pain arising from a discrete locus. The methods minimize potential adverse consequences of Ih channel blockade outside of the locus of pain.

Pharmaceutical compositions for attenuating pain at a site in a human or animal in need thereof can include from 1 μg to 5000 μg of a site 1 sodium channel blocker and from 1 μg to 5000 μg of an alpha-2-adrenergic agonist. In certain preferred embodiments, the dose of each class of drug ranges from about 10 μg to about 3000 μg, from about 300 μg to about 1500 μg, or preferably from about 400 μg to about 1200 μg.

For repeatable on-demand anesthesia, animal and human studies are required to determine effective dosages and volumes for treatment of humans. For example, the rank order of potencies of site 1 sodium channel blockers from in vitro physiology experiments did not predict the rank order of potency of those compounds in vivo (Kohane, et al., Reg. Anesth. Pain Med., 2000; 25: 52-9).

Different clinical situations place different demands on local anesthetic safety and efficacy. Systemic safety determines the upper limit on the total dose (mg or mg/kg) of bupivacaine, STX, NeoSTX, DMED, CLD or other active agents. There are small differences in total permissible dose based on the time course of uptake, vascularity, etc., but overall each local anesthetic has a maximum permissible total dose.

In any localized region of the body, a sufficient local tissue concentration of local anesthetics is required to block afferent transmission. The lowest local concentration of one or more drugs in a given location sufficient to provide pain relief is called the "minimum effective concentration" or MEC.

Thus, clinical situations that require infiltration into large tissue volumes require larger total volumes of local anesthetic at or above MEC than clinical situations that involve smaller tissue volumes. If the MEC is similar in different locations, then larger tissue volumes require a larger total dose than small tissue volumes.

The dose of local anesthetic will depend on the anesthetic being administered as well as the site where the local anesthetic is administered. Typically, dosage units are prepared for use in a volume ranging from about 0.1 ml to about 120 ml. In certain embodiments one or more site 1 sodium channel blockers are present in a concentration range between 0.01% (weight/volume) and 5% (w/v), and one or more alpha-2-adrenergic agonists are present in a concentration range between 0.01% (w/v) and 5% (w/v). Typically, the total systemic dose is no more than 200 mg/kg body weight in adults.

In one embodiment, the additional active agent is dexmedetomidine. The dexmedetomidine can be in a concentration ranging between 0.01 mM and 100 mM, preferably between 0.1 mM and 0.3 mM, most preferably 0.21 mM.

2. Painful Conditions to be Treated

Anesthetic compositions of site 1 sodium channel blockers and optional other agents such as alpha-2-adrenergic agonists may be used to treat many conditions including, but not limited to, the treatment of acute or chronic pain, nociceptive and neuropathic pain, pre- and post-operative pain, cancer pain, pain associated with neurotransmitter dysregulation syndromes and orthopedic disorders, sports-related injuries, acute traumatic pain, nociceptive pain, and neurotransmitter-dysregulation syndromes.

The compositions can be used to prevent or reduce pain associated with a surgical procedure. In some embodiments, dosage units include an amount of one or more site 1 sodium channel blockers and one or more alpha-2-adrenergic agonists effective for the treatment or prevention of pain associated with multiple layers of a large surgical wound for a full-length open laparotomy, thoraco-abdominal incision, or flank incision; for Cesarean delivery, open hysterectomy, esophago-gastrectomy, nephrectomy, or large abdominal cancer surgeries such as colectomies; for wound infiltration for total hip replacement (hip arthroplasty) or total knee replacement (knee arthroplasty); for peripheral nerve blocks or plexus blocks (perineural injection); for infiltration (injection along the layers of a wound); for shoulder, hand or arm surgery, infiltration or ilio-inguinal/ilio-hypogastric blocks for inguinal hernia repair, penile block for hypospadias repair, femoral block for total knee replacement or anterior cruciate ligament repair, intercostal nerve blocks for open chest surgery, or femoral and sciatic nerve blocks for leg amputation or foot and ankle surgery; to provide lumbar sympathetic blockade for complex regional pain syndrome/reflex sympathetic dystrophy or vascular insufficiency of the leg or for celiac plexus blockade for pancreatitis or cancer of the pancreas; for nerve blocks (femoral and sciatic, lumbar plexus and sciatic) for the hip or knee joint for joint replacement surgery; or to provide sciatic nerve blockade of prolonged duration where rapid motor recovery is not necessary, as for a lower leg amputation.

In some embodiments, dosage units can be prepared in an amount effective to prevent, reduce or inhibit sensory and/or motor function in one or more peripheral nerves.

In other embodiments, dosage units contain an amount of one or more site 1 sodium channel blockers with alpha-2-adrenergic agonists to prolong the duration of anesthesia in or around the sciatic nerve.

In some embodiments the compositions can be used in the treatment or prevention of pain for an extended period of time. The methods can include administering to the subject a formulation including one or more site 1 sodium channel blockers in a liposome or particle for controlled or delayed release. Methods including administering liposomes or particles containing one or more site 1 sodium channel blockers and optionally one or more alpha-2-adrenergic agonists to the subject at or near to the painful structure are in an amount effective to reduce or inhibit sensory and/or motor function for a period of one day, one week, two weeks, three weeks, four weeks, one month, two months, six months or more than six months.

In certain embodiments, the methods disclosed herein can be used for the treatment or attenuation of chronic pain, for example chronic pain associated with diseases or disorders. In patients suffering from chronic pain the dose of site 1 sodium channel blockers can be administered to the immediate site of the disease or disorder or to the area surrounding the painful structure.

EXAMPLES

Example 1: Liposomes Conjugated with Gold Nanorods (Lip-GNRs) are Stable at Physiological Temperature with Minimal Cytotoxicity In Vitro Methods
Materials.
Tetrodotoxin (TTX) was obtained from Abcam plc (Cambridge, Mass.); Dexmedetomidine hydrochloride (DMED) was acquired from R&D systems, Inc. (Minneapolis, Minn.). DPPC and DPPG were acquired from Corden-Pharma International (Plankstadt, Germany). Cholesterol and rhodamine 6G were purchased from Sigma (St. Louis, Mo.). Thiolated poly(ethyl glycol) 1,2-Distearoyl-sn-Glycero-3-Phosphoethanolamine (HS-PEG-DSPE, Mw 2000 Da) was from NanoCS Inc. (New York, N.Y.). Tetrodotoxin ELISA kits were purchased from Reagen LLC (Moorestown, N.J.). Gold nanorods were synthesized as reported by Nikoobakht, et al., *M.A. Chem. Mater.,* 15:1957-1962 (2003). PEGylation of GNRs was conducted by incubating with methoxy-PEG-thiol (Mw 2000 Da, Laysan Bio, Arab, Ala.) for 24 hours at room temperature and dialysis against deionized water for three days (Niidome, et al., *J Control Release,* 114(3):343-347 (2006)).

Preparation of Lip-GNRs.

A lipid cake was produced as previously described (Shankarappa, et al., *Proc. Natl. Acad. Sci.* 109(43):17555-60 (2012)). DPPC, DPPG, cholesterol and HS-PEG-DSPE (molar ratio 6:2:3:0.2) were dissolved in a chloroform: methanol (v/v, 9:1) mixture and formed a lipid bilayer under reduced pressure. The bilayer was hydrated with tert-butanol and vacuum-dried to form a fluffy liposome cake. Then the cake was hydrated with 0.25 M ammonium sulfate solution containing GNR (0.04 wt %). The Lip-GNR-0 were homogenized at 10,000 rpm with a ⅜" MiniMicro workhead on a L4RT-A Silverson Laboratory Mixer (East Longmeadow, Mass.) for 10 minutes, then treated with 10 freeze-thaw cycles and dialysis (MWCO 50 KDa, Float-A-Lyzer® G2, Spectrum Laboratories, Inc., Rancho Dominguez, Calif.) against PBS (6 changes of buffer over three days). The Lip-GNR-0 solution was centrifuged at 1000×g for 10 minutes to remove any free GNR. The purified Lip-GNR-0 were characterized by particle analyzer (Delsa Nano C, Beckman Counter) and imaged with cryo-EM (JEOL 2100). The concentration of gold was analyzed by inductively coupled plasma mass spectrometry (ICP-MS, Sciex Elan 6100, Perkin Elmer, Norwalk, Conn.). To prepare Lip-GNRs loaded with drugs or dye, the same procedure was followed with addition of TTX (0.5 mg/mL) and DMED (0.3 mg/mL), or R6G (2.8 mg/mL) in the 0.25 M ammonium sulfate hydration buffer. To form liposomes without GNRs, the same procedure was followed except with 0.25 M ammonium sulfate without GNRs. Drugs and dye in all formulations were quantitated after disruption of the liposome with octyl-β-D-glucopyranoside (100 mM, volume ratio of 2:1 to formulations). The concentration of R6G was determined by a plate reader (BioTek, Winooski, Vt.) with excitation and emission wavelengths of 535 nm and 580 nm. To study the self-quenching effect of R6G in liposome, 0.4 mL of Lip-GNR-R6G were incubated at 4, 37 and 43° C. At each predetermined time point, 10 μL of Lip-GNR-R6G was withdrawn and the fluorescence intensity was determined after 200 folds dilution with PBS. Fluorescent intensity was measured at RT and normalized to that before incubation. DMED and TTX were quantitated by HPLC (at 215 nm, Agilent 1260 series system) and ELISA, respectively. The concentration of lipid was determined by the Bartlett assay as reported by Epstein-Barash, et al., *Proc. Natl. Acad. Sci.,* 106(17):7125-30 (2009); Bartlett, et al., *J Biol Chem,* 234 (3):466-8 (1959).

To study the effect of temperature on R6G release, 0.4 mL of Lip-R6G or Lip-GNR-R6G was placed in a dialysis device (SLIDE-A-LYZER® MINI, MWCO 20 KDa, Thermo Fisher Scientific Inc., Grand Island, N.Y.) against 13.5 mL PBS. At each predetermined time point, the buffer was changed with fresh PBS. The release of TTX and DMED from Lip-GNR-TD at 37° C. was studied and quantitated by ELISA and HPLC.

Cytotoxicity.

C2C12 mouse myoblasts (ATCC, CRL-1772) were cultured in DMEM supplemented with 20% FBS and 1% Penicillin Streptomycin. Cells were seeded into 96-well plate at 50,000 cells per mL in DMEM with 2% horse serum and 1% Penicillin/Streptomycin, and cultured for 10-14 days until the cells differentiated into myotubes. During that time, media were changed every 3-4 days. PC12 cells (ATCC, CRL-1721) originating from rat adrenal gland pheochromocytoma were plated in a 24-well plate at the density of 20,000 cells/well, with F-12K supplemented with 12.5% horse serum, 2.5% FBS, and 1% Penicillin/Streptomycin. 24 hours after seeding, the culture medium was changed to 1% horse serum, 1% Penicillin/Streptomycin and 50 ng/mL nerve growth factor (Life technologies, Grand Island, N.Y.). Media were changed at day 4 and the cells were cultured up to 7 days. The formed myotubes and differentiated PC12 cells were incubated with 100 μL Lip-GNR-TD placed in an insert with porous membrane (0.4 μm). Cell viability was assessed with an MTS assay kit (Promega Corporation, Madison, Wis.).

Results

In order to maximize the local anesthetic efficacy of each triggered drug release event, tetrodotoxin (TTX) and a second molecule, dexmedetomidine (DMED) were encapsulated. TTX is a naturally occurring toxin found in several organisms, whose mechanism of action is unimolecular blockade of site 1 on the extracellular surface of sodium channels on nerves (Catterall, *Annu. Rev. Pharmacol. Toxicol.,* 20, 15-43 (1980); Terlau, et al., *FEBS Lett.,* 293 (1-2), 93-6 (1991)). TTX is an extremely potent local anesthetic (Schwarz, et al., *J. Physiol.,* 233 (1), 167-94 (1973); Wang, et al., *J Gen. Physiol.,* 96 (5), 1105-27 (1990)). Unlike commercially available amino-amide and amino-ester local anesthetics, tissue toxicity from site 1 sodium channel blockers (S1SCBs) after injection at peripheral nerves can be minimal (Padera, et al., *Muscle Nerve,* 34 (6), 747-53 (2006)), even when delivered for prolonged periods (Epstein-Barash, et al., *Proc. Natl. Acad. Sci.,* 106 (17), 7125-30 (2009)). Co-administration of S1SCBs with adjuvant agents can enhance anesthetic effect. For example, the combination of TTX and the α2-agonist DMED can significantly prolong corneal local anesthesia over that from TTX alone (McAlvin, et al., *Invest. Ophthalmol. Visual Sci.,* 56 (6), 3820-6 (2015)).

To achieve repeated on-demand local anesthesia, gold nanorods (GNRs) that are able to convert NIR light into heat were chemically tethered to liposomes (Lip-GNRs) containing TTX and DMED. The GNRs would raise the temperature of the adjacent liposomal lipid bilayer above its transition.

1,2-Dipalmitoyl-sn-glycero-3-phosphocholine (DPPC) and 1,2 dipalmitoyl-sn-glycero-3-phospho-(1'-rac-glycerol) (DPPG) were selected as the liposome lipid components because their transition temperatures (41° C.) are above but close to body temperature (Needham, et al., *Cancer Res,* 60 (5):1197-201 (2000)). Thiolated PEG-DSPE (HS-PEG-DSPE, ~2 mol % of the total lipids) was anchored in the lipid bilayer to bind GNRs through gold-thiol interactions (Wu, et al., *J Am Chem Soc,* 130 (26):8175-7 (2008)). Liposomes without GNRs were made with no payload (Lip 0), or containing rhodamine 6G (Lip-R6G) or TTX/DMED (Lip-TD). Lip-GNRs were made with no payload (Lip-GNR 0), or containing rhodamine 6G (Lip-GNR-R6G) or TTX/DMED (Lip-GNR-TD) (see Methods). Drugs or a dye were loaded by addition to the hydration buffer, and their concentrations in the purified formulations were measured (Table 2). The GNR content in purified Lip-GNRs as measured by ICP-MS was 0.02 wt %. Dynamic light scattering measurement of the purified Lip-GNR-0 demonstrated a mean diameter of 3.3 µm. Cryo-electron microscopy image (cryo-EM) confirmed the association of GNRs with the liposomes.

Figure 1:
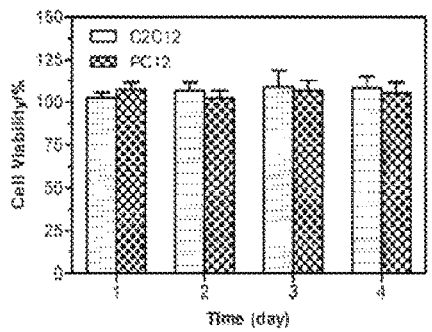

In vitro cytotoxicity assays showed that Lip-GNR-TD were not cytotoxic to $C_2C_{12}$ myotubes and PC12 cells over a four-day period (FIG. 1). $C_2C_{12}$ and PC12 cells are commonly used in toxicological assays of muscle and nerve, respectively.

Figure 2:
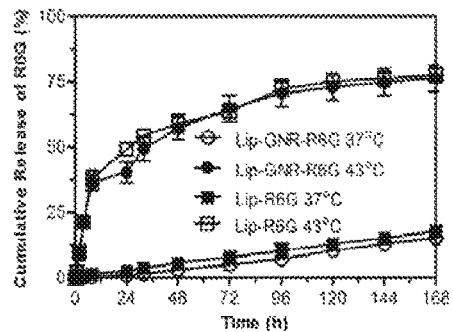

Initial studies of the thermosensitivity of Lip-GNRs were done with R6G. R6G was selected as a model dye since at low pH it is positively charged, like TTX. At 37° C., release of R6G from Lip-GNR-R6G was minimal (FIG. 2), similar to the release profile of R6G from Lip-R6G. Less than 20% of dye was released from Lip-GNR-R6G and Lip-R6G after 2 weeks. These data indicated that tethering to GNR did not alter liposome permeability. When incubated at 43° C., 37% of R6G was released from Lip-GNR-R6G within 8 h, and a cumulative 76.4% of R6G was released by 2 weeks. A similar release profile was observed for R6G release from Lip-R6G at 43° C. These release profiles verified that Lip-GNRs were sensitive to mild hyperthermia.

TABLE 2

Characterization of liposome formulations.
Data are means ± SD (n = 4)

| Formulation | Concentration (mg/mL) | | | |
| --- | --- | --- | --- | --- |
| | TTX | DMED | R6G | Lipid |
| Lip-GNR-R6G | — | — | 2.33 ± 0.19 | 64.6 ± 2.21 |
| Lip-GNR-TD | 0.21 ± 0.02 | 0.17 ± 0.02 | — | 63.3 ± 3.23 |
| Lip-R6G | — | — | 2.04 ± 0.23 | 64.2 ± 2.54 |
| Lip-TD | 0.22 ± 0.03 | 0.15 ± 0.04 | — | 65.3 ± 5.08 |

Example 2: Liposomes Conjugated with Gold Nanorods (Lip-GNRs) are Photosensitive In Vitro Methods
Photosensitivity of Lip-GNRs.

To assess the photosensitivity, Lip-GNR-0 (0.1 mL) were placed in a 96-well plate and irradiated with an 808 nm CW NIR laser for 1-30 minutes, with irradiances ranging from 8 to 75 mW/cm$^2$. The temperature was detected using an FLIR E50 infrared imaging camera (FLIR Systems, Wilsonville, Oreg.) at the beginning and end of each cycle of irradiation. To detect the stability of Lip-GNR-0 after multiple triggers, Lip-GNR-0 were repeatedly irradiated with the NIR laser at 75 mW/cm$^2$ for 15 minutes, followed by cooling at RT for 30 minutes. The size was characterized with particle analyzer at the end of each off-state.

Phototriggerable Release In Vitro.

The phototriggerable release of R6G was evaluated by measuring the fluorescence intensity. Lip-GNR-R6G (0.1 mL) was placed in a 96-well plate and irradiated with an 808 nm CW NIR laser for 10 minutes. The samples were diluted 200 folds with PBS and the fluorescence intensity was measured with a plate reader (BioTek, Winooski, Vt.). The release percentage of R6G was quantitated based on a standard curve that was normalized to 100% dye release obtained by bursting the liposomes with 100 mM octyl β-D-glucopyranoside (2:1 volume ratio to Lip-GNR-R6G).

To evaluate repeated triggerable release of R6G, 100 µL of Lip-GNR-R6G were irradiated at 17 mW/cm$^2$ for ten minutes, followed by cooling at RT for 30 minutes. 5 µL of sample was withdrawn for determination of R6G release. The remaining solution was centrifuged at 4000×g for 10 minutes and the supernatant was changed with PBS.

Results

Figure 3A:
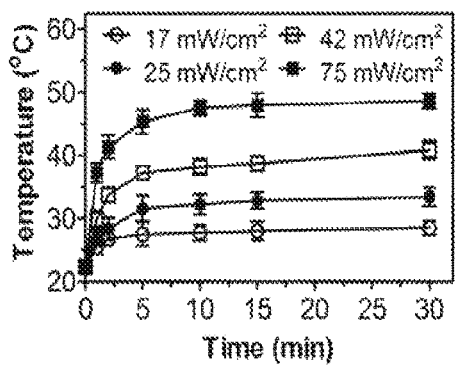
Figure 3B:
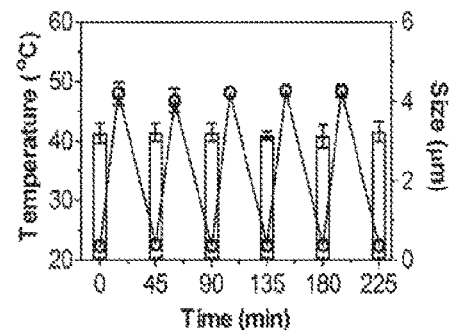

The photosensitivity of Lip-GNRs in PBS was assessed by irradiating Lip-GNR-0 (0.02 wt % of gold and 60-70 mg/mL of lipids) with an 808 nm continuous wave (CW) NIR laser for 1-30 min (FIG. 3A). The bulk temperature of the PBS was measured with an infrared imaging camera. Irradiation caused the temperature of the Lip-GNR-0 solution to increase rapidly during the first 2 min and plateau within 10 min. The plateau temperature increased from 28 to 49° C. as irradiance increased from 17 to 75 mW/cm$^2$. Irradiation at 75 mW/cm$^2$ for more than 2 min heated the solution of Lip-GNR-0 above the 41° C. lipid transition temperature. The stability of phototriggering of Lip-GNR-0 was assessed by repeated NIR laser irradiations at 75 mW/cm$^2$ for 15 min. The particle size and the photothermal response of Lip-GNR-0 did not change over five cycles of irradiation (FIG. 3B). The peak temperature (49° C.) after triggering was higher than the phase transition temperature (41° C.) of the lipids, suggesting that heating the lipid bilayer over the transition temperature did not destroy the liposomes.

Figure 4A:
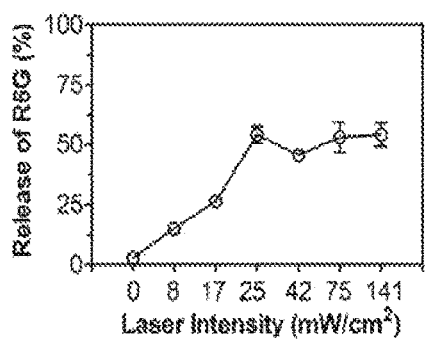
Figure 4B:
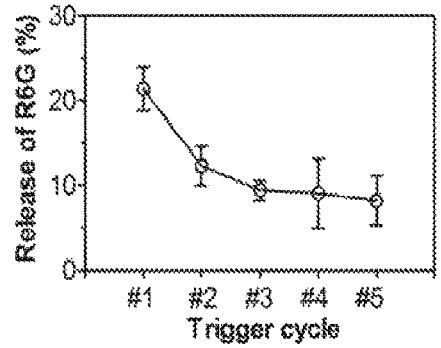

To assess the irradiance required for phototriggerable release, Lip-GNR-R6G were exposed to various irradiances for 10 min (FIG. 4A). The rate of R6G release correlated with irradiance over the range of 0-25 mW/cm$^2$, then plateaued. Repeated triggering with 10 min cycles at 17 mW/cm$^2$ caused R6G release after each irradiation (FIG. 4B), with the release from the first event being considerably larger than from subsequent ones. Seventeen mW/cm$^2$ only heated the solution of Lip-GNR-R6G to 28° C., which is lower than the phase transition temperature of DPPC/DPPG, suggesting that local heating of the liposomes was to a higher temperature than the bulk heating of the medium.

NIR irradiation is a promising tool for triggerable in vivo applications (Timko, et al., *Adv. Mater.* 22 (44), 4925-43 (2010); Timko, et al., *Proc. Natl. Acad. Sci.*, 111 (4), 1349-54 (2014); You, et al., *Small*, 6 (9), 1022-31 (2010); Timko, et al., *Drug Delivery*, 11 (11), 1681-5 (2014); Dai, et al., *J. Am. Chem. Soc.*, 135 (50), 18920-9 (2013); Agarwal, et al., *ACS Nano*, 5 (6), 4919-26 (2011)). However, NIR light may cause burns at high irradiances and/or prolonged irradiation times (Timko, et al., *Proc. Natl. Acad. Sci.*, 111 (4), 1349-54 (2014); Timko, et al., *Drug Delivery*, 11 (11), 1681-5 (2014)). This concern is particularly relevant in devices that can be triggered repeatedly. Liposome-gold nanomaterial system should be designed so that the irradiance required to fully activate it is minimized. Here, gold nanorods attached to the liposomal membrane were able to mediate local actuation of the release of the payload without heating the bulk medium. In this example, Lip-GNRs could be efficiently activated at 17 mW/cm$^2$, while 75 mW/cm$^2$ was required to heat the bulk medium over the 41° C. lipid phase transition temperature.

Example 3: Repeatable and Adjustable Photosensitive Release of Tetradoxoin and Dexmedetomidine from Lip-GNRs In Vitro Methods
Lip-GNR-TD were dialyzed against PBS at 37° C. for 24 hours to remove the burst release of TTX and DMED.

Phototriggerable release of TTX and DMED from Lip-GNR-TD was assessed by ELISA and HPLC, respectively. To test the effect of duration of irradiation on drug release, drug release was measured independently (separate sample) for each duration of irradiation. To evaluate multiple triggerable release, Lip-GNR-TD were irradiated with NIR laser for 10 minutes for five cycles separated by 30 minutes. Free drugs after each trigger were removed by centrifugation (4000×g, 10 minutes) and the Lip-GNR-TD were re-suspended in fresh PBS. cycles separated by 30 minutes. Free drugs after each trigger were removed by centrifugation (4000×g, 10 minutes) and the Lip-GNR-TD were re-suspended in fresh PBS.

Results

In the absence of irradiation of Lip-GNR-TD, both TTX and DMED exhibited a small burst release at the first day, followed by slow sustained release (FIG. 5). Studies of release from irradiated particles was done in particles where the burst release was first removed by dialysis at 37° C. for 24 h, to reflect the in vivo reality that injected particles were only irradiated once the burst release would have resolved (see in vivo study below). Release of TTX and DMED was measured from liposomes conjugated with gold nanorods (Lip-GNR-TD) under continuous irradiation with an 808 nm NIR laser at 25 mW/cm$^2$ (FIG. 6A). Since triggerable release of DMED started to plateau at 10 min, we used that as the duration of irradiation in subsequent studies. Release of both compounds decreased significantly with repeated irradiation (FIG. 6B)

Example 4: Lip-GNR-TD Enables Repeatable and Adjustable Phototriggered On-Demand Infiltration Anesthesia In Vivo Methods Phototriggered Local Anesthesia In Vivo.

Lip-GNR-TD were mixed with Lip-GNR-R6G with a volume ratio of 9:1. Animals were handled daily in a quiet room for up to 7 days before the treatments to familiarize them with the behavioral investigator, the experimental environment, and the specific experimental procedures. The mixture (100 µL) was injected into the footpad of the rat under isoflurane-oxygen anesthesia. Nociceptive behavioral test was conducted by recording the audible vocalization as previous reports with modification (Bartlett, et al., *Anesthesiology*, 96(1), 109-16 (2002); Kayser, et al., *Pain*, 41(3), 353-63 (1990); Kayser, et al., *Brain Res*, 267(1), 131-8 (1983); Fletcher, et al., *Anesthesiology*, 84(5), 1129-37 (1996)). The behavior investigator was not aware of which anesthetic treatment was assigned to any given rat (i.e., he was "blinded"). The degree of infiltration anesthesia was measured by poking the rat footpad with TOUCH TEST® sensory evaluators (North coast medical, Inc., Gilory, Calif.), a series of filaments which provide a defined force (although expressed in gram units) when applied to the body surface. We assessed the force that elicited a vocal or motor (foot withdrawal) response from the animal when we poked the footpad. The greater the force required to elicit a response, the more intense ("dense") the local anesthesia. Filaments with a target force of 26 g, 60 g, 100 g, 180 g and 300 g were used. Forces above 300 g were not used, in order to avoid damage to the footpad (Kissin, et al., *Anesthesiology*, 88(1), 224-32 (1998)).

In the absence of local anesthetic treatments, none of rats responded to the filament with 26 g target force. They began to respond to filaments with a target force of 60-100 g, and all responded to a filament with 180 g target force (Kayser, et al., *Brain Res*, 267(1), 131-8 (1983)). Consequently, 180 g was the force used in testing animals. Each rat was tested five times at each predetermined time point. The effectiveness of local anesthesia was expressed as the percentage (number of times out of 5×100) that a rat did not respond (vocalize and/or withdraw) in response to 180 grams force on the footpad. (No vocalization and/or foot withdrawal after five trials was defined as complete nociceptive block −100% of maximum possible effect [MPE]). The duration of nerve block was calculated as the time that nerve block was >50% MPE. The test was applied every 30 minutes for the first hour and then hourly thereafter until full recovery. Laser irradiation (808 nm CW NIR laser) at 75, 141 and 272 mW/cm$^2$ was conducted for 10 minutes on both feet from day 2 to 5 after injection. The area under the curve (AUC) of the % MPE-time plot was computed using the trapezoidal method (Huang, et al., *Marine drugs*, 10(9), 1899-919 (2012)). Fluorescence intensity of R6G in the injection spot was detected using an in vivo imaging system (IVIS spectrum, Caliper Life Sciences) with excitation and emission wavelengths of 535 nm and 580 nm before and after laser irradiation immediately. The local anesthetic effect of Lip-TD and Lip-GNR-0 and the effect of laser irradiation were studied. 100 µL of formulation was injected into the left footpad and the local anesthesia was assessed by the same procedure. All rats were irradiated at the injection site 24 hours after injection with an 808 nm CW NIR laser (141 mW/cm, 10 minutes).

Statistics.

Data which were normally distributed were described with means and standard deviations. Otherwise, data were presented as median±quartiles. The AUC of the % MPE-time curve for the plot of triggered local anesthesia at different laser irradiances was compared by two-way ANOVA (GraphPad InStat software, GraphPad).

Study Approval.

Male Sprague-Dawley rats (Charles River Laboratories, Wilmington, Mass.) weighing 150 to 200 grams were cared for in accordance with protocols approved by the Animal Care and Use Committee at Children's Hospital, and the Guide for the Care and Use of Laboratory Animals of the U.S. National Research Council (McAlvin, et al., *Biomaterials*, 35(15), 4557-64 (2014)). They were housed in groups, in a 7 am to 7 pm light-dark cycle.

Results

Figure 7A:
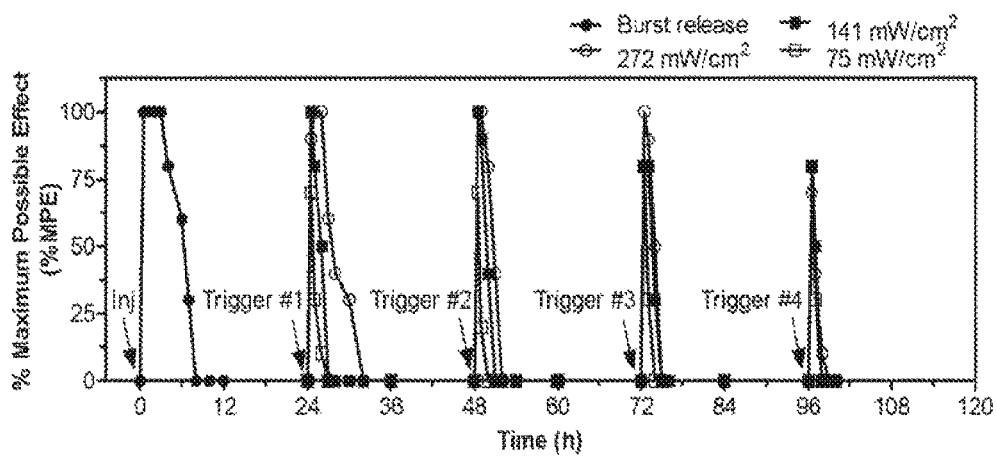
Figure 7B:
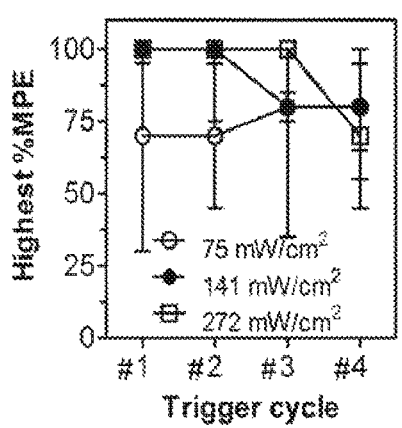
Figure 7C:
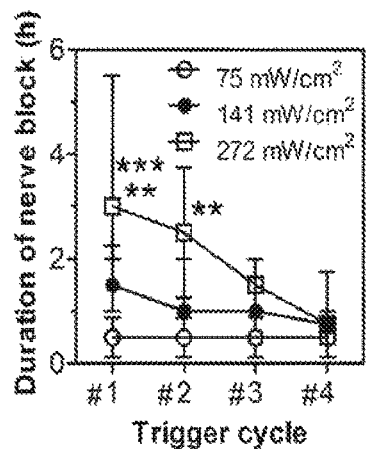
Figure 7D:
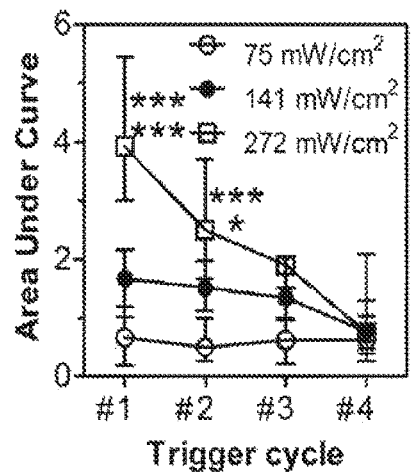

Ninety microliters of Lip-GNR-TD and 10 µL of Lip-GNR-R6G were coinjected subcutaneously into the plantar aspect of the rat left hindpaw under brief isoflurane general anesthesia; neurobehavioral testing was initiated after the animals had recovered. The local anesthetic effect of Lip-GNR-TD was assessed by noting the vocal or motor (foot withdrawal) response to mechanical stimulation to the rat footpad with Touch Test sensory evaluators, and the duration of local anesthesia was calculated (see Methods). The initial local anesthesia had a median duration of 5.0 h (4.0-7.2 h, interquartile range) (FIG. 7A and Table 3). Starting 24 h after injection, after complete resolution of local anesthesia, both footpads were irradiated once a day for 10 min (repeated daily over 4 days). Lip-GNR-TD could be activated in vitro at an irradiance of 25 mW/cm$^2$ (FIG. 7B). Given that light from 178 an 808 nm NIR laser could be greatly attenuated by rat skin ex vivo, (Timko, et al., *Proc. Natl. Acad. Sci.*, 111 (4), 1349-54 (2014)) we increased the laser irradiance used in the in vivo experiments to 75, 141, and 272 mW/cm$^2$. Each 10 min irradiation event (done under isoflurane anesthesia) triggered local anesthesia in the footpad that had been injected with Lip-GNR-TD (FIG. 7A and Table 3) and had no effect of analgesia in the contralateral foot (suggesting a lack of systemic toxicity). Modulation of laser intensity allowed adjustment of the duration and intensity (% MPE) of triggered local anesthesia, as well as the area under the curve (AUC) for those two parameters (FIG. 7A-FIG. 7D). The duration of local anesthesia decreased with progressive triggering events, presumably in reflection of the decreasing triggered flux of drugs with each cycle (FIG. 6B).

Figure 8:
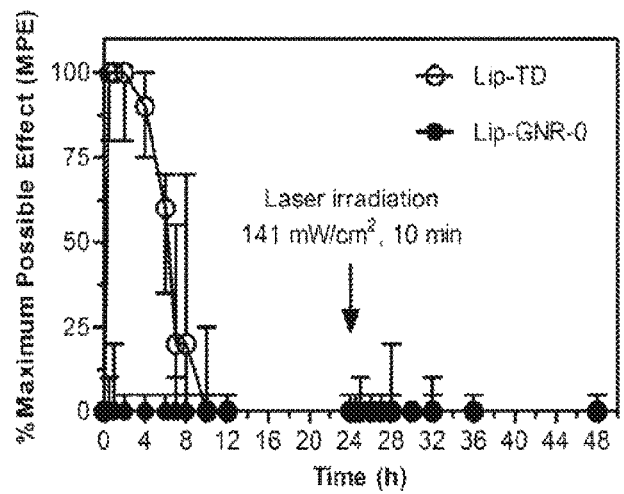
Figure 9A:
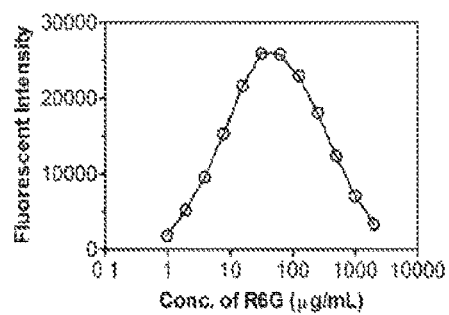
FIGS. 9A-9B are graphs showing the fluorescence intensity of R6G, (FIG. 9A) as a function of its concentration in solution.
Figure 9B:
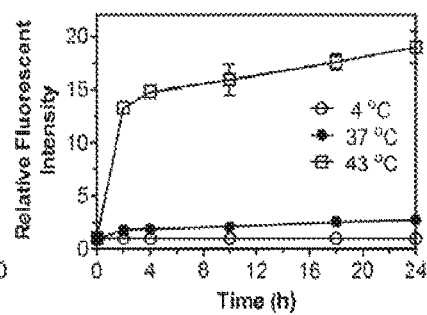
Figure 10:
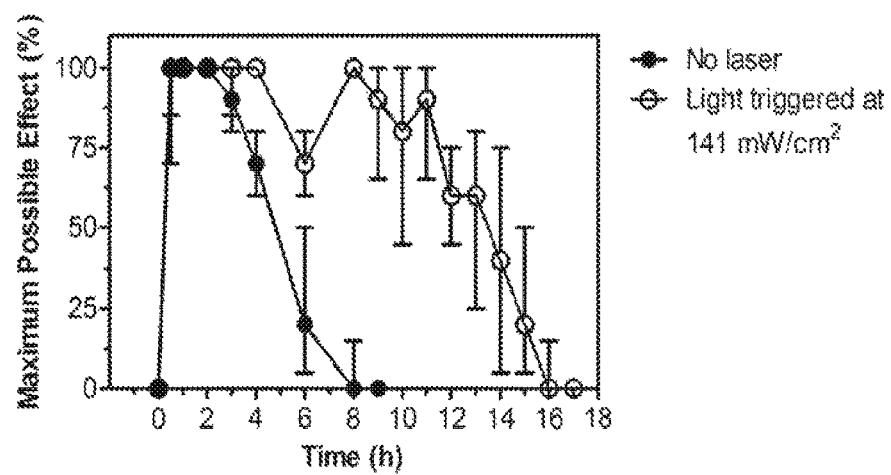
FIG. 10 are graphs showing duration (in hours) of local anesthesia, as a percentage of MPE, following injection of Lip-GNR-TD to the rat footpad, with no laser irradiation and four laser irradiations. Data are medians with 25$^{th}$ and 75$^{th}$ percentiles (n=6).
Figure 11:
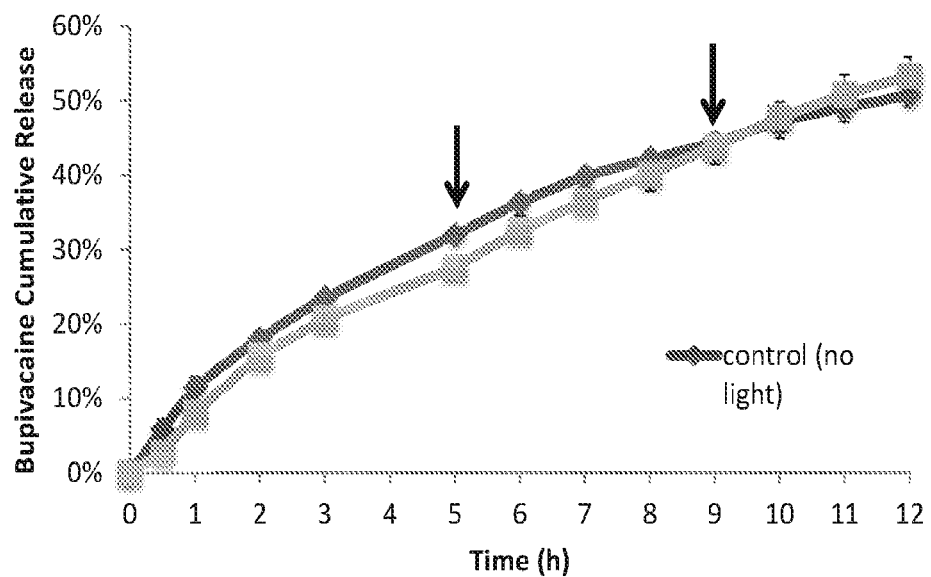
FIG. 11 are graphs showing percentage of bupivacaine release from PdPC(OBu)$_8$ liposomes at 37° C. with and without irradiation (730 nm, 50 mW/cm$^2$, 10 min) at time points indicated by arrows (n=4).

Injection of 100 μL of Lip-TD into the rat footpad induced a similar duration of local anesthesia (median duration of 6.0 h) as from the initial injection of Lip-GNR-TD, which could be due to the burst release of TTX/DMED. Lip-GNR-0 did not produce detectable nerve block. Irradiation (141 mW/cm$^2$ for 10 min) of the injection sites of rats injected with Lip-TD or Lip-GNR-0 24 h after injection produced no detectable local anesthesia (FIG. 8). These results indicated that laser irradiation itself did not trigger the release of TTX/DMED from Lip-TD in the absence of GNR and that localized heating by Lip-GNR-0 was not responsible for the local anesthesia. Phototriggerable release of R6G from Lip-GNR-R6G was visualized with an in vivo imaging system. The concentration of R6G in Lip-GNR-R6G was 2.33 mg/mL, displaying very low fluorescence because of self-quenching, which occurs when the concentration is higher than 31.25 μg/mL (FIG. 9A and FIG. 9B) (Magde, et al., Photochem. Photobiol., 75(4), 327-34 (2002)). Rat left footpads were imaged immediately before and after irradiation. Phototriggerable release of R6G from Lip-GNR-R6G resulted in brighter imaging since the released R6G was diluted outside of liposomes. The in vivo imaging of the rat footpad that received the Lip-GNR-R6G injection showed increased size and intensity of fluorescence after each triggering event although the extent of that increase tapered with progressive triggering events. The temporal arrangement of the triggered local anesthesia could also be altered by changing the timing of irradiation. For example, one could achieve prolonged continuous local anesthesia by irradiating the footpad of rats receiving Lip GNR-TD at 141 mW/cm$^2$ for 10 min whenever the % MPE dropped below 100% for four times in total. Individual irradiation events are not shown since their timing varied from rat to rat. In this way, the duration of local anesthesia was prolonged from 4.0 h (interquartile range: 4.0-5.5 h) to 13.0 h (interquartile range: 12.0-14.8 h, with four cycles of the triggering) (FIG. 10).

In this example, the phototriggerable local anesthesia device could be repeatedly triggered to provide local anesthesia at least four times over a five-day period, after the initial nerve block had worn off. Aside from the initial nerve block, there was minimal basal anesthetic effect in the absence of irradiation.

TABLE 3

The duration (h) of local anesthesia in the left rat footpad after injection of TTX/DMED loaded liposomes conjugated with gold nanorods (Lip-GNR-TD). Data are medians with 25th and 75th percentiles (n = 4-14).

| Time of injection (h) | Blockade duration (h) | | | | | |
|---|---|---|---|---|---|---|
| | 75 mW/cm$^2$ | | 141 mW/cm$^2$ | | 272 mW/cm$^2$ | |
| | Left foot | Right foot | Left foot | Right foot | Left foot | Right foot |
| 0 (Injection, no trigger) | 5.0 (4.0-7.2) | 0 (0-0) | 5.0 (4.0-7.2) | 0 (0-0) | 5.0 (4.0-7.2) | 0 (0-0) |
| 24 (trigger #1) | 0.5 (0-0.84) | 0 (0-0) | 1.5 (1.0-2.2) | 0 (0-0) | 3.0 (2.0-5.5) | 0 (0-0) |
| 48 (trigger #2) | 0.5 (0-0.84) | 0 (0-0) | 1.0 (0.8-2.0) | 0 (0-0) | 2.5 (1.2-3.8) | 0 (0-0) |
| 72 (trigger #3) | 0.5 (0-0.84) | 0 (0-0) | 1.0 (0.8-2.0) | 0 (0-0) | 1.5 (1.0-2.0) | 0 (0-0) |
| 96 (trigger #4) | 0.5 (0-0.84) | 0 (0-0) | 0.8 (0.4-1.0) | 0 (0-0) | 0.8 (0-1.8) | 0 (0-0) |

Example 5: Lip-GNR-TD with Repeated Laser Irradiation Caused No Tissue Injury

Methods
Histology.
All rats were euthanized with carbon dioxide 8 days after injection. All treated rat footpads were dissected and processed for histology.
Results
Rats receiving Lip-0 (no irradiation), Lip TD (no irradiation), Lip-GNR-TD (no irradiation), and Lip GNR-TD (4 cycles of laser irradiation at 141 mW/cm$^2$, 10 min) were euthanized 8 days after injection, and the footpads were dissected for histological study. Light microscopy images of hematoxylin/eosin-stained sections of these groups showed that there was no injury to the skin and underlying tissues (data not shown). Inflammation at the injection site, with macrophages and lymphocytes, occurred in all treatment groups, as is commonly seen with injected particles (Epstein-Barash, et al., Proc. Natl. Acad. Sci., 106(17), 7125-30 (2009); McAlvin, et al., Biomaterials, 35(15), 4557-64 (2014); Anderson, et al., Eur. J. Pharm. Biopharm, 40(1), 1-8 (1994)). Foamy macrophages were observed, likely reflecting uptake of the injected formulations (McAlvin, et al., Biomaterials, 35(15), 4557-64 (2014); Kohane, et al., J. Biomed. Mater. Res., 59(3), 450-9 (2002)). It is unlikely that there was significant neural injury given that we saw little tissue injury or inflammation: those phenomena occur well before there is any nerve injury, as we have documented in other sustained release formulations containing site 1 sodium channel blockers and other compounds (Epstein-Barash, et al., Proc. Natl. Acad. Sci., 106(17), 7125-30 (2009); Shichor, et al., Biomaterials, 33 (13), 3586-93 (2012)).

Example 6: Phototriggerable Liposomes Work Effectively with Site 1 Sodium Channel Blockers (S1SCBs) but not Conventional Local Anesthetics Methods
Preparation of Lip-GNR-BUP.
A lipid cake was produced as described by Shankarappa, et al., Proc. Natl. Acad. Sci. 109(43): 17555-60 (2012). DPPC, DPPG, cholesterol and HS-PEG-DSPE (molar ratio 6:2:3:0.2) were dissolved in a chloroform:methanol (v/v, 9:1) mixture and formed a lipid bilayer under reduced pressure. The bilayer was hydrated with tert-butanol and vacuum-dried to form a fluffy liposome cake. Then the cake was hydrated with 0.25 M ammonium sulfate solution containing GNR (0.04 wt %). The Lip-GNR-0 were homogenized at 10,000 rpm with a ⅜" MiniMicro workhead on a L4RT-A Silverson Laboratory Mixer (East Longmeadow, Mass.) for 10 minutes, then treated with 10 freeze-thaw cycles and dialysis (MWCO 50 KDa, Float-A-Lyzer® G2, Spectrum Laboratories, Inc., Rancho Dominguez, Calif.) against PBS (6 changes of buffer over three days). The Lip-GNR-0 solution was centrifuged at 1000×g for 10 minutes, and the supernatant was replaced by 30 mg/mL bupivacaine hydrochloride solution. Liposome suspensions with bupivacaine added were stirred at 50° C. for 30 min. Liposome suspensions were centrifuged at 1000×g for 10 minutes to remove free bupivacaine. Bupivacaine was quantitated after disruption of the liposome with octyl-β-D-glucopyranoside (100 mM, volume ratio of 2:1 to formulations). The concentration of bupivacaine was determined by HPLC (at 215 nm, Agilent 1260 series system).

Phototriggered Local Anesthesia In Vivo.

Animals were handled daily in a quiet room for up to 7 days before the treatments to familiarize them with the behavioral investigator, the experimental environment, and the specific experimental procedures. Lip-GNR-BUP (100 μL) was injected into the footpad of the rat under isoflurane-oxygen anesthesia. Nociceptive behavioral test was conducted by recording the audible vocalization as previous reports with modification (Bartlett, et al., *Anesthesiology*, 96(1), 109-16 (2002); Kayser, et al., *Pain*, 41(3), 353-63 (1990); Kayser, et al., *Brain Res*, 267(1), 131-8 (1983); Fletcher, et al., *Anesthesiology*, 84(5), 1129-37 (1996)). The behavior investigator was not aware of which anesthetic treatment was assigned to any given rat (i.e., he was "blinded"). The degree of infiltration anesthesia was measured by poking the rat footpad with TOUCH TEST® sensory evaluators (North Coast Medical, Inc., Gilory, Calif.), a series of filaments which provide a defined force (although expressed in gram units) when applied to the body surface. We assessed the force that elicited a vocal or motor (foot withdrawal) response from the animal when we poked the footpad. The greater the force required to elicit a response, the more intense ("dense") the local anesthesia. Filaments with a target force of 26 g, 60 g, 100 g, 180 g and 300 g were used. Forces above 300 g were not used, in order to avoid damage to the footpad (Kissin, et al., *Anesthesiology*, 88(1), 224-32 (1998)). In the absence of local anesthetic treatments, none of rats responded to the filament with 26 g target force. They began to respond to filaments with a target force of 60-100 g, and all responded to a filament with 180 g target force (Kayser, et al., *Brain Res*, 267(1), 131-8 (1983)). Consequently, 180 g was the force used in testing animals. Each rat was tested five times at each predetermined time point. The effectiveness of local anesthesia was expressed as the percentage (number of times out of 5×100) that a rat did not respond (vocalize and/or withdraw) in response to 180 grams force on the footpad. (No vocalization and/or foot withdrawal after five trials was defined as complete nociceptive block –100% of maximum possible effect [MPE]). The duration of nerve block was calculated as the time that nerve block was >50% MPE. The test was applied every 30 minutes for the first hour and then hourly thereafter until full recovery. Laser irradiation (808 nm CW NIR laser) at 141 mW/cm was conducted for 10 minutes on both feet at day 2 after injection.

PdPc(OBu)$_8$ Liposome Preparation.

Liposomes were prepared by the thin lipid film hydration method as reported (Shankarappa, et al., *Proc. Natl. Acad. Sci.* 109(43):17555-60 (2012)). The lipid formulation: 1,2-distearoyl-sn-glycero-3-phosphocholine (DSPC)(Avanti Polar Lipids, Alabaster, Ala.), 1,2-dilinoleoyl-sn-glycero-3-phosphocholine (DLPC)(Avanti Polar Lipids, Alabaster, Ala.), 1,2-distearoyl-sn-glycero-3-phosphatidylglycerol (DSPG) (Genzyme, Cambridge, Mass.), and cholesterol (Sigma, Milwaukee, Wis.) at molar ratio 3:3:2:3, along with 0.45 mol % (based on total lipid) PdPC(OBu)$_8$, was dissolved in a solution of chloroform:methanol 9:1. The solvent was then vaporized, and the lipid was redissolved in t-butanol, followed by lyophilization. The lipid cake was hydrated with a 0.25 M ammonium sulfate solution and homogenized at 10,000×g for 5 min using a ⅜" MiniMicro workhead on a L5M-A Silverson Laboratory Mixer. The solution was then dialyzed against PBS in a 50 kDa molecular mass cut-off dialysis tube (Spectrum Laboratories, Rancho Dominguez, Calif.) for 48 h. After centrifuging with 4000×g for 30 min, the supernatant was replaced by 30 mg/mL bupivacaine hydrochloride solution. Liposome suspensions with bupivacaine added were stirred at 50° C. for 30 min then dialyzed against PBS in a 50 kDa molecular mass cut-off dialysis tube (Spectrum Laboratories, Rancho Dominguez, Calif.) for 48 h.

Animal Studies.

Adult male Sprague-Dawley rats (Charles River Laboratories) weighing 325-400 g were housed in groups under a 6 am to 6 pm light-dark cycle.

After being anesthetized with isoflurane-oxygen, the animals were injected with 200 μL of liposomes using a 23G needle. The needle was introduced postero-medial to the greater trochanter, pointed in the antero-medial direction, and upon contact with bone, the liposomes were injected onto the sciatic nerve (7). The animals were irradiated with a 730 nm laser for 15 min at 330 mW/cm$^2$.

Sensory nerve block was examined at predetermined time points by a modified hotplate test (hind-paw thermal latency), as reported previously (Thalhammer et al., *Anesthesiology*, 82, 1013-1025; Kohane et al., *Anesthesiology*, 89, 119-131)). The plantar surface of the rat's hind paw was placed on a pre-heated hot plate at 56° C. The time until the animal withdrew its foot (the thermal latency) was recorded. Animals that did not retract their foot after 12 s were removed from the hotplate to prevent thermal injury. A thermal latency above 7 s was considered a successful nerve block for the purpose of calculating the duration of nerve block. Measurements were repeated 3 times at each time interval.

Motor nerve block was assessed by a weight-bearing test to determine the motor strength of the rat's hindpaw, as described previously (Thalhammer et al., *Anesthesiology*, 82, 1013-1025; Kohane et al., *Anesthesiology*, 89, 119-131)). In brief, the rat was positioned with one hindpaw on a digital balance and was allowed to bear its own weight. The maximum weight that the rat could bear without the ankle touching the balance was recorded, and motor block was considered achieved when the motor strength was less than half-maximal, as described previously (Thalhammer et al., *Anesthesiology*, 82, 1013-1025; Kohane et al., *Anesthesiology*, 89, 119-131)).

Durations of sensory block were calculated by the time required for thermal latency to return to 7 s, with 2 s as the baseline and 12 s as complete sensory block. The duration of motor block was defined as the time it took for the weight bearing to return halfway to normal from the maximal block (Kohane et al., *Anesthesiology*, 89, 119-131)).

Results

The phototriggerable release from these vehicles are dependent on the encapsulated drug. More specifically, the developed phototriggerable liposomes are highly effective in the encapsulation and release of site 1 sodium channel blockers, but they are ineffective when encapsulating and phototriggering the release of conventional local anesthetics, such as bupivacaine.

Two liposomal formulations utilizing different phototriggering mechanisms are demonstrated here to support this concept. Both liposomes contained tetrodotoxin (TTX), which is a site one sodium channel blocker that has ultrapotent local anesthetic properties. In the first formulation, the phototriggerable liposomes were made photo-labile by encapsulation of the photosensitizer $PdPC(OBu)_8$; irradiation at 730 nm led to peroxidation of liposomal lipids, allowing drug release. In vitro, 5.6% of TTX was released upon NIR irradiation, which could be repeated a second time. The formulations were not cytotoxic in cell culture. In vivo, injection of liposomes containing TTX and $PdPC(OBu)_8$ at the sciatic nerve caused an initial nerve block lasting 13.5±3.1 hours. Additional periods of nerve block could be induced by irradiation at 730 nm. The timing, intensity, and duration of nerve blockade could be controlled by adjusting the timing, irradiance, and duration of irradiation. Tissue reaction to this formulation and the associated irradiation was benign.

When the $PdPC(OBu)_8$ liposomes were loaded with bupivacaine, however, no phototriggerable release was shown in vitro (FIG. 11). Injection of bupivacaine loaded liposomes to rat sciatic nerve induced an initial nerve block with blockade less than 1 h, much shorter than the TTX-loaded liposomes, and irradiation showed no effect (FIG. 12). These results demonstrate that the phototriggerability of $PdPC(OBu)_8$ liposomes were limited to a specific group of drugs (site 1 sodium channel blockers).

Gold nanorods (GNRs) that can convert near infrared (NIR) light into heat were attached to liposomes (Lip-GNRs), enabling light-triggered phase transition of their lipid bilayers with a consequent release of payload. Lip-GNRs containing the site 1 sodium channel blocker tetrodotoxin and the $\alpha_2$-adrenergic agonists dexmedetomidine (Lip-GNR-TD) were injected subcutaneously in the rat footpad. Irradiation with an 808 nm continuous wave NIR laser at 141 $mW/cm^2$ for 10 minutes produced on-demand and repeated infiltration anesthesia in the rat footpad with minimal toxicity.

Bupivacaine-loaded phototriggerable release was shown in vitro at a higher irradiance than the irradiation for in vitro drug release from Lip-GNR-TD. When irradiated with 25 $mW/cm^2$, the same irradiance as in the in vitro experiments for Lip-GNR-TD, negligible (~1%) of drug was released (FIG. 13). Irradiation of bupivacaine-loaded liposomes was achieved at 75 $mW/cm^2$, which induced a 20-30% release of bupivacaine and could be repeated for a second time (FIG. 13). Injection of bupivacaine-loaded liposomes into the rat footpad induced an initial nerve block with blockade of 2 h, shorter than the initial nerve blockade of Lip-GNR-TD (5.5 h) (FIG. 14). Upon irradiation, the intensity of nerve blockade was 60%, whereas Lip-GNR-TD showed 100% of nerve blockade upon irradiation (FIG. 14). Bupivacaine loaded GNR liposomes are phototriggerable, but less effective than Lip-GNR-TD.

The ability to achieve on-demand and repeated local anesthesia could be very beneficial in the management of pain. In addition, the phototriggerable liposomal formulations were specific to site 1 sodium channel blockers, encapsulating local anesthetics such as bupivacaine showed ineffective encapsulation and loss of phototriggerability.

Example 7: Co-Delivery of Dexmedetomidine (DMED) Reduced the Photo-Energy Threshold Required for Triggered Nerve Blockade, Enabled Light-Emitting Diodes (LEDs) as a Light Source, and Allowed More Triggerable Events of Local Anesthesia Materials and Methods Preparation of Liposomes Loaded with Different Agents Photosensitizer (PS) 1,4,8,11,15,18,22,25-octabutoxyphthalocyaninato-palladium(II) ($PdPC(OBu)_8$) was synthesized as reported (Rwei A Y, et al., *Proc. Natl. Acad. Sci. USA,* 112:15719-15724 (2015)). 1,4,8,11,15,18,22,25-octabutoxy-29H,31H-phthalocyanine (Aldrich) was dissolved in anhydrous dimethylformamide and mixed with $PdCl_2$ (Aldrich) in a 1:3 molar ratio. The solution was purged with nitrogen for 30 min, followed by stirring at 120° C. for 24 h. Purification was achieved with the addition of excess $H_2O$. The end product was characterized by UV-Vis absorption and had an absorption peak at 734 nm in dichloromethane.

TTX and $PdPC(OBu)_8$ were co-loaded into liposomes (Lipo-PS-TTX) that contained the unsaturated lipid 1,2-dilinoleoyl-sn-glycero-3-phosphocholine (DLPC) as in Example 6.

DMED was loaded into separate liposomes with the same lipid composition (Lipo-DMED).

Specifically, liposomes were prepared following a thin film hydration method. DSPC (Avanti Polar Lipids), DLPC (Avanti Polar Lipids), DSPG (Genzyme), and cholesterol (Sigma) in the molar ratio 3:3:2:3 were dissolved in a chloroform:methanol 9:1 solution. PS was added at 0.45 mol % (of total lipid) for the preparation of PS-loaded liposomes. The solvent was evaporated to form a lipid thin film, which was redissolved in t-butanol and further lyophilized. The lipid cake was hydrated with PBS, TTX solution (0.3 mg/mL PBS; Abcam), DMED solution (1 mg/mL PBS with 1M HCl 18 μL/mL; Sigma), or sulforhodamine B solution (10 mg/mL PBS; Aldrich). The suspension was homogenized with a ⅜-in MiniMicro workhead (Silverson) on an L5M-A Laboratory Mixer (Silverson) at 10,000×g for 5 min. The suspension was then dialyzed against PBS for 48 h in a 1000 kDa MWCO dialysis tube (Spectrum Laboratories). Liposomes were imaged by cryo-TEM for morphology evaluation. The size of the liposomes was characterized by a Beckman Coulter Multisizer 3. TTX liposomal content was measured by ELISA (Reagen) after lipid removal using the Bligh and Dyer method (Bligh E G and Dyer W J, *Can. J. Biochem. Physiol.,* 37:911-917 (1959)). DMED content was measured by HPLC with a mobile phase of 70% $H_2O$ with 0.1% trifluoroacetic acid and 30% Acetonitrile with 0.1% trifluoroacetic acid. Sulforhodamine B content was determined by UV-Vis absorption at 565 nm.

TTX Release Studies In Vitro

TTX release was studied by incubating liposome samples at 37° C. and placing 200 μL samples into Amicon Ultra-0.5 mL centrifugal filters (100 kDa MWCO) at predetermined time points, and centrifuging them at 5000×g for 15 min. The filtrate was collected and analyzed by ELISA.

DMED Release Studies In Vitro

The DMED release study was performed by placing 100 μL of liposome sample into a Slide-A-Lyzer MINI dialysis device (Thermo Fisher) with a 20 kDa MWCO and dialyzing it against 1.4 mL PBS at 37° C. The dialysis solution was replaced with fresh, pre-warmed PBS at predetermined time intervals. Irradiation was performed with a 730-nm laser (100 mW/cm2, 10 min) at the 0 h and 24 h time points. The concentration of DMED was determined by HPLC.

Cytotoxicity of Diffusible Components from Liposomes

100 μL of liposomes (Lipo-DMED+Lipo-PS-TTX 1:1 vol mixture) were placed in the upper well of Transwell® systems, with cells in the lower well in 600 μL of media, following which irradiation (730 nm, 100 mW/cm$^2$, 10 min) was performed.

Pharmacokinetic Studies

Animals were anesthetized with isoflurane-oxygen and injected with 50 μL of 10 mg/mL sulforhodamine B PBS solution at the sciatic nerve co-injected with or without 50 μL of 50 μg/mL DMED. At predetermined time points (15 min, 30 min, 1 h, 2 h, 4 h, 6 h), blood was harvested by tail-bleeding and centrifuged at 4000×g for 15 min. The supernatant was collected and methanol was added at a 1:1 vol ratio. Samples were left at 4° C. overnight then centrifuged at 20,000×g for 15 min, and the supernatant was collected. The concentration of sulforhodamine B was analyzed by fluorescence (excitation/emission: 560/580 nm).

Liposomal pharmacokinetics studies were performed by co-injecting 200 μL of Lipo-PS-Srho with 200 μL of Lipo or Lipo-DMED at the sciatic nerve. At predetermined time points (30 min, 3 h, 7 h and 10 h), blood was harvested by tail-bleeding.

Phototriggered Nerve Block In Vivo

Under brief isoflurane-oxygen anesthesia, animals were co-injected with 200 μl of Lipo-PS-TTX or Lipo-PS and 200 μL of Lipo-DMED or Lipo at the sciatic nerve using a 23-G needle. Sciatic nerve injection followed procedures that were previously reported (McAlvin J B, et al., *Biomaterials*, 35:4557-4564 (2014)). Animals were irradiated using a 730-nm laser or a 725-755 nm LED at the timing, irradiance and duration indicated in the Results section.

Nerve block was examined by a modified hotplate test as reported by Kohane D S, et al., *Anesthesiology*, 89:119-131 (1998); and Thalhammer J G, et al., *Anesthesiology*, 82:1013-1025 (1995). In brief, the plantar surface of the animal's hindpaw was placed onto a 56° C. hotplate, and the thermal latency (defined as the time the animal allowed its paw to remain on the hotplate) was measured: the time (s) at which the animal withdrew its hindpaw. Animals that did not withdraw their paw after 12 s were removed from the hotplate. The average of three measurements was used. A thermal latency of 2 s indicated no nerve block (baseline), and a thermal latency of 12 s indicated deep nerve block. (Hindpaws were removed from the hotplate by the operator after 12 s to prevent thermal injury.) Successful nerve block was defined as blocks achieving a thermal latency above 7 s (half-way between a baseline of 2 s and a maximum latency of 12 s). Duration of nerve block was calculated as the time required for thermal latency to return to 7 s.

Histology

Animals were euthanized by carbon dioxide 4 d after the last irradiation event. The sciatic nerve and surrounding tissue were harvested and H&E staining was performed. The samples were scored for inflammation and myotoxicity. The observer was blinded to the nature of the individual samples. The inflammation score was scaled from 0 to 4, where 0 was normal and 4 was severe inflammation. The myotoxicity score was scaled from 0 to 6 as previously reported (5, 50): 0=normal; 1=perifascicular internalization; 2=deep internalization (more than five cell layers); 3=perifascicular regeneration; 4=deep tissue regeneration (more than five cell layers); 5=hemifascicular regeneration; 6=holofascicular regeneration.

The tissues were sectioned, processed for hematoxylin-eosin staining, and the inflammation and myotoxicity were scored (Table 4).

TABLE 4

Tissue reaction to Lipo-PS-TTX + Lipo-DMED

|  | No Light | Irradiated*** |
|---|---|---|
| Inflammation* | 1 (1-1) | 1 (1-1) |
| Myotoxicity** | 0 (0-1) | 0 (0-0.25) |

*Inflammation scores (0 = normal to 4 = severe inflammation; see Methods). Data are medians ± quartiles, n = 4. P = 0.32 comparing Lipo-PS-TTX + Lipo-DMED groups with and without irradiation.
**Myotoxicity scores (0 = normal to 6 = severe myotoxicity). Data are medians ± quartiles, n = 4. P = 0.50 comparing Lipo-PS-TTX + Lipo-DMED groups with and without irradiation.
***Rats were exposed to nine separate and consecutive 5-min irradiation events with a 730-nm laser at 75 mW/cm$^2$, 41 h after injection of formulation.

Cell Viability

C2C12 mouse myoblasts [American Type Culture Collection (ATCC) CRL-1772] and PC12 rat adrenal gland pheochromocytoma cells (ATCC, CRL-1721) were cultured as reported (Epstein-Barash H, et al., *Proc. Natl. Acad. Sci. USA*, 106:7125-7130 (2009); Zhan C, et al., *Nano Lett*, 16:177-181 (2016)). C2C12 cells were cultured with DMEM (20% FBS, 1% Penicillin Streptomycin) medium and seeded into 24-well plates at 25,000 cells/well. Cells were then differentiated to myotubules in DMEM (2% horse serum, 1% Penicillin Streptomycin) medium for 10-14 days. PC12 cells were cultured with DMEM (12.5% horse serum, 2.5% FBS, 1% Penicillin Streptomycin) medium and seeded into 24-well plates at 2,000 cells/well. The cells were differentiated in DMEM with 1% horse serum, 1% Penicillin Streptomycin, and 50 ng/mL nerve growth factor (Life technologies) for 7 days.

The cytotoxicity of the diffusible components from the liposomes was evaluated. Liposomes of 100 μL/well were exposed to cells by a 24-well TRANSWELL® membrane (Costar 3495, pore size 0.4 rpm) and were irradiated with a 730-nm laser (100 mW/cm$^2$, 10 min). Cell viability was determined by the MTS assay 96 h after exposure to liposomes.

Statistical Analysis

Histological scoring (inflammation and myotoxicity) was described with medians and quartiles due to its ordinal character, and statistical comparisons were done with the Mann-Whitney U test. All other data groups were described with means and standard deviations and compared with the Student t-test.

Results

Characterization of Liposomes

The mean size of Lipo-PS-TTX was 4.9±3.0 μm, and the loading efficiency was 25%. Lipo-DMED had a mean size of 6.3±4.4 μm and a loading efficiency of 36%.

Effect of DMED and Lipo-DMED on Local Drug Distribution

It was hypothesized that DMED would induce local vasoconstriction, limiting drug redistribution from the injection site. To validate this hypothesis, the pharmacokinetics in blood of a hydrophilic fluorescent dye, sulforhodamine B (Srho), was studied after co-injection with DMED in vivo at the sciatic nerve. FIG. 15 shows co-injection of Srho and DMED decreased the peak Srho plasma concentration by 27.5%, and delayed the time to that peak level from 30 min to 60 min after injection.

To demonstrate that Lipo-DMED could have the same effect, it was co-injected with Srho-loaded liposomes (Lipo-Srho) at the sciatic nerve, and the pharmacokinetics of Srho was studied. FIG. 16 shows co-injection of Lipo-DMED and Lipo-Srho (1:1 vol) decreased the Srho peak plasma concentration by 79.6%, and the Srho plasma concentration was significantly lower for up to 7 h after injection compared with co-injection of blank liposomes (Lipo) and Lipo-Srho. There was no significant difference in Srho plasma concentration 10 h after injection.

These results indicated that DMED, free or encapsulated, significantly reduced the redistribution of Srho from the injection site into the systemic circulation, trapping the dye at the local site of injection.

In Vitro Phototriggered Release

The release of TTX from a Lipo-DMED+Lipo-PS-TTX (FIG. 17A; 1:1 vol, here and in all subsequent studies in this Example) mixture was studied by determining the concentration of non-encapsulated TTX in filtrate from a centrifugal filter at predetermined intervals at 37° C. FIG. 17B shows in the absence of irradiation, 3% of total TTX was released in the first 3 hours, followed by slow release. Irradiation (730 nm, 10 min, 100 mW/cm$^2$) at the 0 h time point released 20% of TTX within the first hour, after which a return to slower release was observed; further irradiation events at the 4 and 8 h time points released 11% and 25% within the subsequent hours respectively, followed by a return to slower release. These results demonstrated that the release of TTX from the Lipo-PS-TTX+Lipo-DMED mixture was controllable by light.

DMED release from the Lipo-DMED+Lipo-PS-TTX mixture was studied by dialyzing 100 μL of the liposomal mixture against 1.4 mL of PBS. FIG. 17C shows irradiation at the 0 h and 24 h time points showed no significant difference in release kinetics when compared with the non-irradiated group, demonstrating that DMED release was not phototriggerable.

To examine whether DMED had any effect on the release of TTX from particles, release from Lipo-PS-TTX+Lipo-DMED was compared to that from Lipo-PS-TTX+blank liposomes (Lipo), both irradiated with a 730 nm laser (10 min, 50 mW/$cm^2$), at 37° C. after the initial TTX release was completed. FIG. 18 shows no significant difference was observed, indicating that an observed biological effects would be due to drug effects in tissue rather than differences in release kinetics.

Cytotoxicity

The cytotoxicity of diffusible components from Lipo-DMED+Lipo-PS-TTX with and without irradiation was assessed in two different cell lines relevant to local anesthetic-related tissue injury: C2C12, a myotube cell line, and PC12, a pheochromacytoma cell line frequently used for the assessment of neurotoxicity. FIGS. 19A and 19B show there was no significant decrease in cell viability in any group in either cell line.

Sciatic Nerve Blockade

Liposomal formulations were injected at the sciatic nerve in vivo, followed by neurobehavioral testing. FIG. 20A shows co-injection of Lipo-DMED and Lipo-PS-TTX caused an initial nerve block lasting 32.9±7.1 h. Starting at the 41 h time point, i.e. after return to baseline latency, the injection site was irradiated (730 nm, 5 min, 75 mW/$cm^2$). If the irradiation event resulted in nerve block, it was allowed to resolve before the next irradiation was performed. The first seven irradiation events achieved effective nerve block (thermal latency>7 s). The 8th and the 9th induced an increase in thermal latency, but without exceeding 7 s (6.2 s and 4.5 s respectively).

FIG. 20A also shows co-injection of Lipo-PS-TTX and Lipo (no DMED) induced an initial nerve block of 16.8±1.5 h, followed by a return to baseline latency. Irradiation (730 nm, 5 min, 75 mW/$cm^2$) did not produce nerve block, indicating that Lipo-DMED was necessary for the induction of nerve blockade at low irradiance with short duration. Co-injection of PS-loaded liposomes (Lipo-PS) and Lipo-DMED did not result in initial or triggered nerve block, demonstrating that it was not irradiation itself and/or Lipo-DMED that resulted in nerve block. Lipo-PS-TTX was necessary for the induction of nerve block.

To demonstrate that the duration of triggered nerve block could be adjusted by controlling the duration of irradiation, Lipo-PS-TTX+Lipo-DMED were co-injected at the sciatic nerve and irradiation was performed 41 h after injection, after the thermal latency had returned to baseline from the initial block. FIG. 20B shows the duration of nerve block increased with increasing duration of irradiation. FIG. 20C shows there was a linear relationship between the irradiated energy density (the product of irradiation duration and irradiance) and nerve block duration for both the Lipo-PS-TTX only and Lipo-PS-TTX+Lipo-DMED groups, demonstrating that therapeutic effects can be modulated by adjusting the irradiance and/or duration of irradiation. This relationship could allow patients to conveniently adjust the onset, intensity, and duration of pain relief at will, according to their changing pain conditions, providing a personalized approach towards pain relief. Co-injection of Lipo-PS-TTX and Lipo-DMED decreased by 94% the irradiation threshold that was necessary for nerve block compared with animals injected with Lipo-PS-TTX only. In addition, the slope of the nerve block duration with respect to energy density, which reflects the therapeutic effectiveness per unit of irradiation energy (J/$cm^2$), increased by 2.9 fold with the addition of Lipo-DMED.

Tissue Reaction

The sciatic nerve and surrounding tissues were collected 4 days after the last irradiation event. All animals injected with PS-loaded liposomes had green particle deposits surrounding the sciatic nerve, whereas animals injected with non-PS-loaded liposomes had white particle deposits. These results showed that the liposomes were deposited at the target site and the injections were performed accurately. The tissues did not appear edematous, discolored, or with other signs of tissue injury.

The tissues were sectioned, processed for hematoxylin-eosin staining, and the inflammation and myotoxicity were scored. All animals injected with liposomes showed mild inflammation (median inflammation score=1), consistent with findings upon injections of other particulates (Kohane D S, et al., *J Biomed. Mater. Res.,* 59:450-459 (2002); Anderson J M, *Eur. J. Pharm. Biopharm,* 40:1-8 (1994)). Foamy macrophages were observed, indicating uptake of liposomes. No significant myotoxicity (median inflammation score=0) or other tissue injury was observed in animals injected with liposomes, whether or not irradiated for nine separate and consecutive 5-min irradiation events.

LED-Triggered Sciatic Nerve Block

The evidence that repeated nerve block could be achieved with low irradiances from a 730-nm laser indicated that a LED could be effective. Lipo-PS-TTX+Lipo-DMED was injected at the sciatic nerve. FIG. 21A shows that 41 hours later, i.e. after the initial nerve block wore off, irradiation with a 725-755 nm LED at 50 mW/$cm^2$ for 15 min induced a nerve block of 47±19 min. LED irradiation of animals with Lipo-PS-TTX+Lipo (no DMED) induced a slight increase in thermal latency that did not exceed 7 s. Irradiation with an LED was less effective than with a laser, as FIG. 21B shows that animals injected with Lipo-PS-TTX+Lipo-DMED and irradiated with a laser (50 mW/cm$^2$, 15 min) 41 h after injection developed a nerve block lasting 85±26 min.

Discussion

Improving photoresponsive systems (greater sensitivity, more effect from a given irradiance) was achieved by co-encapsulating a second drug that affected the efficacy of the first. Lipo-PS-TTX were effective in triggering nerve block in vivo but required 330 mW/cm$^2$ over 15 min to do so (Rwei A Y, et al., *Nano Today*, 10:451-467 (2015)). With the addition of DMED, effective triggering could be achieved with 75 mW/cm$^2$ over 5 min, an energy so low that it was ineffective with Lipo-PS-TTX. The threshold for achieving nerve block was 76 J/cm$^2$ with Lipo-PS-TTX, and the addition of Lipo-DMED decreased that threshold by 94% to 4 J/cm$^2$, i.e. much less irradiance was required to achieve therapeutic effect. Moreover, the increase in therapeutic effect for a given increase in irradiance was improved by addition of DMED, as evidenced by the ~3-fold steeper slope of the relationship between irradiance and effect. That improvement in therapeutic effect was due to an effect of DMED on tissue, not on the formulation itself Another consequence of the DMED was the enhanced therapeutic effect of released TTX—and therefore that less TTX was required to have a given effect. Consequently, more nerve block events could be triggered; nine (two of which did not achieve our criteria for nerve block) compared to two for Lipo-PS-TTX (Rwei A Y, et al., *Nano Today*, 10:451-467 (2015)).

Injection before the procedure would provide approximately one day of local/regional anesthesia, which would then wear off over the ensuing twelve hours. At any point, the patient could irradiate the site of injection to achieve nerve block to the desired degree. This could be repeated at will until a total of at least 2.5 days of analgesia had been achieved—which covers the most painful period for many procedures. Potentially, triggering less often or with less irradiance would allow more triggering events because there would be less depletion of TTX, although that would have to be balanced against loss of TTX through slow untriggered release.

A potential mechanism for DMEM to prolong the effects of local anesthetics is analgesic effects mediated by $\alpha_2$-adrenergic agonism or blockade of hyperpolarization-activated cation currents (Kosugi T, et al., *Br. J. Pharmacol.*, 160:1662-1676 (2010); Brummett C M, et al., *Anesthesiology*, 115:836-843 (2011); Brummett C M, et al., *Anesthesiology*, 109:502-511 (2008); Brummett C M, et al., *Anesthesiology*, 111:1111-1119 (2009); Yoshitomi T, et al., *Anesth. Analg.*, 107:96-101 (2008); McAlvin J B, et al., *Invest. Ophthalmol. Vis. Sci.* 56:3820-3826 (2015)). A second mechanism is $\alpha_2$-adrenergic receptor mediated vasoconstriction (Yabuki A, et al., *Reg. Anesth. Pain Med.*, 39:133-136 (2014); Afonso J, et al., *Revista Brasileira De Anestesiologia*, 62:118-133 (2012); Kohane D S, et al., *Reg. Anesth. Pain Med*, 26:239-245 (2001)), which would restrict the redistribution of local anesthetics from the injection site. Data show that vasoconstriction played a role with these formulations. 10 h after injection, the plasma concentration of Srho from Lipo-Srho+Lipo was similar to that from Lipo-Srho+Lipo-DMED, suggesting that DMED-induced vasoconstriction was no longer in effect, even though the effect of DMED lasted on nerve block was observed >40 h after injection of Lipo-DMED+Lipo-PS-TTX. This indicated that ongoing vasoconstriction may not have been responsible to the enhancement of nerve block at later time points. Vasoconstrictive effects indicate caution regarding the use of this formulation near end arteries (fingers, eyes, etc.), or perhaps in patients with poor peripheral circulation (e.g. diabetics). However, a similar improvement of nerve blockade might be achievable by co-delivering TTX with agents which enhance its effect without significant vasoconstriction, such as conventional local anesthetics (Adams H J, et al., *Anesth. Analg.*, 55:568-573 (1976)).

A major limitation of many phototriggerable drug delivery systems is the high dosage of light necessary for drug release or other therapeutic effects to be activated. This problem is exacerbated by attenuation as light passes through tissues in vivo, and can have deleterious effects on effectiveness and safety. Such attenuation of light may make the amount of therapeutic released within the body insufficient to have an effect. Conversely, increasing the irradiance to the point where it is effective may cause burns. NIR light between 700 nm-900 nm penetrates deeper into tissue than do UV and visible light (Steiner R, et al., *Springer, Berlin,* 2011, chap. 2, pp. 23-36), but can still be considerably attenuated (Henderson T A, et al., *Neuropsychiatr. Dis. Treat.*, 11:2191-2208 (2015); Jagdeo J R, et al., *PLoS ONE,* 7, 347460 (2012)). Consequently, it is important for NIR-responsive systems to be as sensitive to irradiation at the appropriate wavelength as possible, and to have the greatest possible therapeutic effect from a given drug release event (i.e. from a given amount of irradiation), especially when targeting deeper tissues.

LEDs have the advantage of low cost, light weight, and requiring less energy to operate compared to laser systems. Being triggerable by LEDs is likely to be an advantageous feature for clinical translation as there can be safety and cost concerns related with laser systems for outpatient treatment.

The phototriggered drug delivery system presented here seemed suitable for the timeframe of perioperative but likely not for chronic pain unless fairly frequent injections were contemplated. Even were the drug loading and basal drug release increased, it remains likely that the particles themselves would be degraded/removed within two weeks. It may be that systems with larger reservoir capability would be necessary for long-term therapy.

Example 8: Co-Delivered Liposomal Bupivacaine, Liposomal Dexamethasone, and Liposomal DMED Enhanced the Duration of Sciatic Nerve Block An approach to prolong the duration of anesthesia is to combine local anesthetics molecules that enhance their effect. For example, the $\alpha_2$ adrenergic receptor agonist dexmedetomidine (DMED) enhances the effect of epidural bupivacaine (Yektas A and Belli E, *Pain Res Manag*, 19:75-81 (2014); Castillo J, et al., *Anesthesiology*, 85:1157-1166 (1996); An K, et al., *PLoS ONE*, 10(4):e0123459, (2015)). However, the effect of such combination on sciatic nerve block was modest (Helal S M, et al., *Saudi Journal of Anaesthesia*, 10:18-24 (2016)).

Materials and Methods

Liposome Preparation

Using thin lipid film hydration (Helal S M, et al., *Saudi Journal of Anaesthesia*, 10:18-24 (2016); Castillo J, et al., *Anesthesiology*, 85:1157-1166 (1996)), liposomes were prepared with DSPC (Avanti Polar Lipids) and cholesterol (Sigma) at molar ratio of 4:1. Once lyophilized, the lipid cakes were hydrated with DMED 50 mg/mL or dexamethasone solution 1 mg/mL in PBS. For liposomal loading of bupivacaine, the remote loading technique with $(NH_4)_2SO_4$ was used (Tufek A, et al., *Clin Invest Med*, 36:E95-102 (2013)).

Animal Studies

After being anesthetized with isoflurane-oxygen, combinations of liposomes containing bupivacaine, DMED, or dexamethasone were injected into the rats at the sciatic nerve. Sensory nerve block was examined by a modified hotplate test as reported previously, by an examiner blinded as to the treatment groups (Brummett C M, et al., *Anesthesiology*, 109:5022-511 (2008); Lavand'homme P M and Eisenach J C, *Pain*, 105:247-254 (2003)). The time until the animal withdrew its foot was recorded as the hind-paw thermal latency, on which a maximum of 12 s was imposed to prevent thermal injury. A thermal latency above 7 s was considered a successful nerve block, and durations of sensory block were calculated by the time required for thermal latency to return to 7 s.

Histology

Animals were euthanized by carbon dioxide 4 d after the injection. The sciatic nerve and surrounding tissue were harvested and underwent standard procedures to produce H&E-stained slides. The samples were scored for inflammation (0-4) and myotoxicity (0-6), as reported (Padera R F, et al., *Muscle Nerve*, 34(6):747-753 (2006)). The myotoxicity score was determined by the nuclear internalization and regeneration of myocytes, two representative characteristics of local anesthetics' myotoxicity.

Results

Liposome Size and In Vitro Drug Release

The average size of the DMED, dexamethasone, and bupivacaine liposomes was determined to be 2.4±0.8 µm (mean±SD). In vitro drug release study confirmed that encapsulating the drugs within the liposomes produced sustained release.

Nerve Blocks

The combination of liposomal DMED or dexamethasone with liposomal bupivacaine yielded nerve blocks that lasted about 50% longer than those from the control injections of liposomal bupivacaine co-injected with PBS liposomes. Co-injection of liposomal bupivacaine with liposomal DMED and liposomal dexamethasone produced a nerve block that lasted almost three times as long as the control. Combinations of liposome-encapsulated local anesthetics for prolonged duration local anesthesia increased sciatic nerve block from 5.5 h (liposomal bupivacaine) to 16.2 h (co-injection of liposomal bupivacaine, liposomal dexamethasone and liposomal dexmedetomidine). Liposomal PBS, DMED, and dexamethasone alone did not cause nerve block in the absence of bupivacaine.

Tissue Reaction

Injection of liposomal bupivacaine resulted in moderate inflammation and myotoxicity. Co-injection of liposomal dexamethasone and liposomal DMED with liposomal bupivacaine did not increase the inflammation and myotoxicity profile compared with liposomal bupivacaine.

Liposomal dexamethasone and DMED prolonged the duration of block from liposomal bupivacaine, enhancing its therapeutic effectiveness with no additional negative impact on tissue toxicity. The combination should be useful for the treatment of acute pain, such as perioperative or postoperative analgesia.

Example 9: Liposomes Encapsulating Sonosensitizer for Ultrasound Triggered Local Anesthesia Many of the current ultrasound-triggerable drug delivery systems, such as micelles (Li F, et al., *Ultrason. Sonochem.*, 30:9-17 (2016)), liposomes (Lin C Y, et al., *Nanomedicine*, 10:67-76 (2014)), composites (Kim H J, et al., *Adv. Mater.*, 18:3083-3088 (2006)), and hybrid (Adams H J, et al., *Anesth Analg*, 55:568-573 (1976)) materials, are responsive to the thermal and mechanical effects of ultrasound waves. Ultrasound can also induce sonochemistry, the use of ultrasound to carry out chemical reactions (Cintas P, et al., *Ultrason. Sonochem.*, 25:8-16 (2015)). Ultrasound has been used for treating tissue depths of 2.3 to 5 cm (Hayes B T, et al., *Journal of Athletic Training*, 39:230-234 (2004)). This shows that ultrasound has the ability to (1) reach relatively deep organs, and (2) allow the application of lower ultrasonic energy for the treatments of superficial tissues, ensuring a more suitable safety profile. In this context, sonodynamic therapy (SDT) has been proposed as an analogous strategy to photodynamic therapy (PDT), in which a sonosensitizer is activated by acoustic energy to generate reactive oxygen species (ROS) (Wood A K and Sehgal C M, *Ultrasound Med. Biol.*, 41:905-928 (2015)) However, the generation of ROS by this effect remains largely unexplored for triggering the release of drugs (Shi J, et al., *ACS Appl. Mater. Interfaces*, 7:28554-28565 (2015)).

Materials and Methods

Ultrasound and NIR Light Tissue Penetration Ex Vivo

The penetration depth of ultrasound and NIR light was evaluated ex vivo with bovine muscle as the model tissue. Tissues were cut and stacked to indicated thicknesses for the measurements. The amount of NIR light (light source: 160 mW/cm$^2$, 730 nm laser) that penetrated through tissue was quantified by a power meter (PM100USB, Thorlabs, NJ, USA).

Ultrasound penetration at each tissue depth was determined by an Olympus 5072PR (set on receiver mode) with a 1 MHz transducer connected to an Oscilloscope (Tektronix 2012B). A calibration curve was obtained with ultrasound intensities (New Pocket Sonovit, New Age Italia Srl, Italy) plotted against the amplitude of the wave received in the oscilloscope. The ultrasound parameter used for tissue penetration measurements was 1 MHz, 3 W/cm$^2$, continuous application.

Liposome Preparation

Liposomes were prepared by the thin-film hydration method, using a formulation. Briefly, the lipid formulation [DSPC (Avanti Polar Lipids), DLPC (Avanti Polar Lipids), DSPG (Genzyme), and cholesterol (Sigma) at molar ratio 3:3:2:3], along with the indicated amount of the sonosensitizer PPIX, was dissolved in a solution of chloroform: methanol 9:1. The solvent was then evaporated under reduced pressure, and the lipid was redissolved in t-butanol, followed by freeze-drying. The lipid cake was hydrated with PBS, TTX solution (0.375 mg/mL PBS; Abcam, MA, USA), or sulforhodamine B solution (10 mg/mL PBS; Aldrich). After 10 freeze-thaw cycles, the solution was dialyzed against PBS for 48 h in a dialysis tube with a molecular mass cut-off of 1000 kDa. The dialysis media were changed with fresh PBS at least twice a day. Lipo-DMED was made following the same procedure, with PPIX not included in the formulation and hydration with 1 mg/mL of DMED in PBS-HCl solution (18 µM final concentration HCl in PBS).

Liposome Characterization

Liposome size was determined with Beckman Coulter Multisizer 3. Liposomal sulforhodamine B content was determined by UV-Vis absorption (λmax=565 nm) after disrupting the liposomes with octyl β-D-glucopyranoside (OGP) (Sigma-Aldrich, Milwaukee, Wis., USA). Liposomal PPIX content was determined by UV-Vis absorption at 402 nm after disrupting the liposomes in ethanol. Liposomal TTX content was determined by ELISA (Reagen, Moorestown, N.J., USA) after removing the lipid fraction using the Bligh and Dyer method (Bligh E G and Dyer W Y, *Can. J. Biochem. Physiol.*, 37:911-917 (1959)). The effect of PPIX loading on ultrasound triggerability of liposomes was evaluated in liposomes encapsulating the fluorescent dye sulforhodamine B using a previously reported method (Zhan C, et al., *Nano Lett*, 16:177-181 (2016); Carter K A, et al, *Nature Communications*, 5, article number 3546, (2014)).

Reactive Oxygen Species (ROS) Detection

A general ROS fluorescent indicator, Carboxy-H2DCFDA (Molecular Probes, OR, USA), was dissolved in ethanol and diluted 100 fold in PBS, followed by the addition to liposome suspension to a final concentration of 10 µM. The fluorescence emission at 527 nm (excitation: 493 nm) was monitored after applying ultrasound to 1 mL of the solution at 3 W/cm$^2$ for 10 min.

Lipid Peroxidation

To determine the degree of lipid peroxidation in the system, a Fe-based colorimetric method was used. Briefly, 0.9 mL of a methanolic solution of xylenol orange (100 µM), Fe$^{2+}$ (250 µM), H$_2$SO$_4$ (25 mM) and butylated hydroxytoluene (4 mM) was incubated with 100 µL of sample for 30 min at room temperature. The absorbance at 560 nm was measured.

In Vitro Release of Fluorescent Dye

Sulforhodamine B (SRho) was encapsulated at a concentration where self-quenching resulted in low fluorescence; once SRho was released, its fluorescence increased, which was measured to determine SRho release from liposomes. Self-quenching sulforhodamine B was used as a hydrophilic model dye. To measure ultrasound-triggered release, sulforhodamine B liposomes were diluted 200 fold in PBS. 1 mL of the suspension was placed in a 20-mL glass vial and sealed with a latex membrane. Ultrasonic gel was then placed between the latex membrane and the ultrasonic source. Ultrasound was applied at the reported power and duration. The fluorescent intensity (excitation/emission: 560/580 nm) was recorded. The release of dye from liposomes upon ultrasound exposure was quantified according to the following equation:

$$\text{Cumulative Release (\%)} = \frac{F - F_0}{F_{break} - F_0} \times 100$$

F=Fluorescence of solution upon ultrasound exposure
F$_0$=Fluorescence of liposome solution prior to ultrasound exposure F$_{break}$=Fluorescence of surfactant (octyl β-D-glucopyranoside)-disrupted liposome solution.

In Vivo Imaging with Dye-Loaded Liposomes

The feasibility of the formulation to achieve ultrasound-triggered release in vivo was studied as follows. Lipo-PPIX-SRho (150 µL) was injected subcutaneously and the dye release upon ultrasound application was measured by fluorescence. Fluorescent intensity was detected and quantified using an in vivo imaging system (IVIS spectrum, Caliper Life Sciences) before and after ultrasound application (3 W/cm$^2$, 10 min, 1 MHz) with excitation and emission wavelengths of 535 nm and 580 nm.

In Vitro TTX Release

Drug release experiments were performed by placing 150 µL of TTX-loaded liposomes into a Slide-A-Lyzer MINI dialysis device (Thermo Scientific, Tewksbury, Mass., USA) with a 20,000 MW cut-off. The sample was dialyzed against 14 mL PBS and incubated at 37° C. on a platform shaker (New Brunswick Innova 40, 150 rpm). At predetermined intervals, the dialysis solution was exchanged with fresh PBS. To measure the ultrasound-triggerability of the liposomes, ultrasound was applied (3 W/cm$^2$, 1 MHz) for 10 min at the 5-h time point. TTX concentration was determined by ELISA (Reagen LLC, NJ, USA).

Cell Culture

Cell culture with C2C12 mouse myoblasts (American Type Culture Collection (ATCC) CRL-1772) and PC12 rat adrenal gland pheochromocytoma cells (ATCC, CRL-1772) was carried out as previously reported. In brief, C2C12 cells were cultured in DMEM (20% FBS, 1% Penicillin Streptomycin (Invitrogen)) and seeded onto a 24-well plate at 25,000 cells/mL. To induce myotubule differentiation, the seeded cells were incubated in DMEM (2% horse serum and 1% Penicillin Streptomycin) for 10-14 days.

PC12 cells were grown in DMEM (12.5% horse serum, 2.5% FBS and 1% Penicillin Streptomycin) and seeded onto a 24 well-plate. Nerve growth factor (final concentration 50 ng/mL, Invitrogen) was added 24 h after seeding.

Cell Viability

To determine the cytotoxicity of the formulation's diffusible components after ultrasound exposure, 100 µL of liposomes with and without pre-exposure to ultrasound (1 MHz, 3 W/cm$^2$, 10 min) were exposed to cells by a 24-well Transwell® membrane (Costar 3495, pore size 0.4 µm) inserted into the cell culture well plates. Cell viability was evaluated by the MTS assay (Promega, WI, USA) 24 h after exposure to liposomes.

Animal Studies

Animal studies were performed according to protocols approved by the Boston Children's Hospital Animal Care and Use Committee following the guidelines of the International Association for the Study of Pain. Adult male Sprague-Dawley rats (Charles River Laboratories) weighing 300-400 g were housed in groups under a 12-h/12-h light/dark cycle with lights on at 7:00 AM. After being anesthetized with isoflurane-oxygen, the animals were injected with 200 µL of liposomes with or without 200 µL of Lipo-DMED, using a 23G needle. The injection was performed perineural at the sciatic nerve as previously described (the needle was introduced posteromedial to the greater trochanter, injection was performed upon contact with bone). The animals were exposed to ultrasound for the reported timing and durations (New Pocket Sonovit, New Age Italia Srl, Italy).

Sensory nerve block was examined at different time points by a modified hotplate test (hind-paw thermal latency). The rat's hindpaw was placed on a preheated hot plate at 56° C. The time until the animal withdrew its paw foot (the thermal latency) was recorded. Animals that did not retract the paw after 12 s were removed manually to prevent thermal injury. 2 s was considered baseline. Durations of sensory block were calculated as the time required for thermal latency to return to 7 s (the middle point between baseline and maximum possible thermal latency). The principal metric of nerve block was the thermal latency (the length of time a rat would leave its hindpaw on a hotplate; 2 s was baseline and 12 s was maximal nerve block). In general, block was considered successful if latency was >7 s. Duration of nerve block was defined as the time for thermal latency to return to 7 s, the mid-point between baseline and maximal block. Measurements were repeated three times at each time point, and the median was used for further data analysis.

Histology

Rats were euthanized by carbon dioxide 4 d after the last ultrasound exposure. The sciatic nerve and surrounding tissue were harvested and underwent standard procedures to produce H&E-stained slides. Inflammation and myotoxicity of the samples were scored. All scoring and other histological assessments were performed by an observer (A.Y.R.) blinded as to the nature of the individual samples. The inflammation score was a subjective quantification of severity in which 0 was normal and 4 was severe inflammation. The myotoxicity score was determined based on nuclear internalization and regeneration of myocytes, which are representative characteristics of local anesthetics' myotoxicity. Nuclear internalization was characterized by myocytes having nuclei located away from their usual location at the periphery of the cell. Regeneration was characterized by the presence of shrunken myocytes with basophilic cytoplasm. The scoring scale was as follows: 0=normal; 1=perifascicular internalization; 2=deep internalization (more than five cell layers); 3=perifascicular regeneration; 4=deep tissue regeneration (more than five cell layers); 5=hemifascicular regeneration; 6=holofascicular regeneration.

Nerve tissue was processed with toluidine blue staining. In brief, the sciatic nerve tissues were fixed in Karnovsky's KII Solution (2.5% glutaraldehyde, 2.0% paraformaldehyde, 0.025% calcium chloride in 0.1 M cacodylate buffer, pH 7.4), followed by postfixation with osmium tetroxide. Samples were then stained with uranyl acetate, dehydrated in graded ethanol solutions, and infiltrated with propylene oxide/TAAB 812 Resin (TAAB Laboratories, Calleva Park, United Kingdom) mixtures. Tissue sections were stained with toluidine blue.

Ultrasound Imaging

The Visualsonics Vevo 2100 (VisualSonics Inc., Toronto, ON, Canada) with an MS-550D 40 MHz transducer at B-mode was used for sonography. In vitro imaging was achieved by applying 100 μL of liposome or water on top of a layer of ultrasonic gel, and covering it with another layer of gel. The top layer gel was in contact with the transducer. Sprague-Dawley rats of 300-400 g were anesthetized with isoflurane-oxygen and positioned under the ultrasound transducer. Ultrasonic gel was applied between the transducer and the rat. A 23G needle was used to inject 200 μL of Lipo-PPIX. The needle was placed beside the sciatic nerve as shown from the real-time sonogram prior to liposome administration.

Statistical Analysis

Statistical comparisons were performed using the student t-test unless stated otherwise. Inflammation and myotoxicity scores were reported by medians and quartiles due to its ordinal character. All other data were described by means and standard deviations.

Results

Liposome In Vitro Characterizations

PPIX was encapsulated in liposomes consisting of unsaturated lipid (1,2-dilinoleoyl-sn-glycero-3-phosphocholine; DLPC), saturated lipid (1,2-distearoyl-sn-glycero-3-phosphocholine; DSPC), 1,2-distearoyl-sn-glycero-3-phosphatidylglycerol (DSPG), and cholesterol. FIG. 22 shows the mean size was 3.1±0.9 μm and ultrasound application did not induce statistically significant changes in liposome size (p=0.95, N=4).

The effect of PPIX loading on ultrasound triggerability of liposomes was evaluated in liposomes encapsulating the fluorescent dye sulforhodamine B (Lipo-PPIX-SRho). FIG. 23A shows the greatest dye release under ultrasound application (3 W/cm$^2$, continuous application, 1 MHz, 10 min) occurred at 0.3% loading (mg PPIX/mg lipid) concentration (or at 0.42 mM). The decrease in ultrasound triggerability of higher PPIX concentrations than 0.3% could be attributed to an increase in formulation stability due to the hydrophobicity of the PPIX included in the lipid bilayer, or to another possible explanation that after a certain concentration of PPIX, there was a self-quenching effect that diminished its efficacy in ROS generation. FIG. 23B shows the greatest generation of ROS under insonation also occurred at 0.3% PPIX. Consequently, 0.3% PPIX was used in all subsequent experiments in this Example. The formulation that produced the highest amount of ROS was the same formulation that had the highest ultrasound-triggered dye release. These results indicate a dual mechanism, in which both the stability of the formulation and the self-quenching effect of sonosensitizers were involved. In liposomes made with DSPC instead of the unsaturated and peroxidizable DLPC, dye release from insonation was greatly reduced. Lipid peroxidation was measured with a previously reported Fe-based colorimetric method, where lipid peroxide-mediated oxidation of $Fe^{2+}$ to $Fe^{3+}$ formed a chromophore with the colorimetric indicator xylenol orange and yielded a strong absorption at 560 nm. FIGS. 23C-23F show the release of dye from Lipo-PPIX-SRho was dependent on the frequency, duration, intensity and duty cycle of the ultrasound exposure.

FIG. 24 shows the dye release could be repeatedly triggered from liposomes by application of ultrasound (3 W/cm$^2$, 1 MHz, 5 min), with up to 4 triggerable events releasing of 4.3%±0.8%, 4.5%±0.9%, 8.2%±2%, and 6.0%±0.9% respectively. Ultrasound for 10 min resulted in greater release at each repeat and fewer release events (2.5 release events). Insonation increased liposomal dye release by 5.1±1.0, 9.1±1.0, 18.0±1.5, and 22.0±0.4 folds compared with the release profile of liposomes without ultrasound, after each ultrasound event.

In Vivo Dye Release

Ultrasound-triggered release of dye from subcutaneously injected Lipo-PPIX-SRho was demonstrated in vivo with an animal fluorescence imaging system. Imaging analysis showed upon ultrasound exposure (3 W/cm$^2$, 1 MHz, 10 min), the fluorescence in the injection area increased by 56%±9% (N=4; p=0.001).

Ultrasound-Triggered TTX Release In Vitro

TTX was encapsulated in PPIX-loaded liposomes (Lipo-PPIX-TTX) with a mean size of 2.8±0.5 μm analyzed from cryo-transmission electron microscopic images. Table 5 shows the loading efficiencies of TTX and PPIX were 22.2±0.2% and 79.1±8.5% respectively, comparable to results from previous studies of TTX loading in liposomes (Rwei A Y, et al., *Proc. Natl. Acad sCI. usa,* 112:15719-15724 (2015)).

TABLE 5

Loading efficiencies of TTX and PPIX in liposomes.

| | Compound concentration | | | Loading efficiency (%) | | |
|---|---|---|---|---|---|---|
| | PPIX (μg/ml) | SRho (mg/ml) | TTX (μg/ml) | PPIX | SRho | TTX |
| Lipo-PPIX-TTX | 197.7 ± 21.2 | — | 83.3 ± 0.5 | 79.1 ± 8.5 | — | 22.2 ± 0.2 |
| Lipo-TTX | — | — | 78.2 ± 7.4 | — | — | 20.9 ± 2.0 |
| Lipo-PPIX-Srho | 185.3 ± 27.3 | 2.6 ± 0.2 | — | 74.1 ± 10.9 | 26.1 ± 1.8 | — |
| Lipo-Srho | — | 2.4 ± 0.2 | — | — | 23.9 ± 1.6 | — |

In vitro TTX release was assessed by dialyzing 150 μL of Lipo-PPIX-TTX against 14 mL of PBS. FIG. 25A shows 7.1±1.0% of TTX was released within the first 4 h, followed by a slower baseline release of approximately 0.4%, and ultrasound (3 W/cm$^2$, 1 MHz, 10 min) applied at the 5 h time point induced a mean release of 5.4±2.6% of TTX over the next 4 h. Without ultrasound the mean release was 1.4±1.0% over the same period. Liposomes loaded with TTX but without PPIX (Lipo-TTX) had comparable TTX loading to Lipo-PPIX-TTX as shown in Table 5, but TTX release was faster in the absence of PPIX: initial release was 19.6±5.7% in the first 4 h, after which release leveled off as shown in FIG. 25B. FIG. 25B also shows ultrasound applied to Lipo-TTX at the 5 h time point did not trigger TTX release. These results showed that PPIX was necessary for ultrasound-triggered TTX release.

Ultrasound-Triggered Sciatic Nerve Blockade

FIG. 26A and Table 6 show Lipo-PPIX-TTX induced an initial nerve block with a mean duration of 8.3±4.7 h (N=4; Table S2).

TABLE 6

Duration of nerve block from Lipo-PPIX-TTX with or without Lipo-DMED repeated ultrasound (US) applications

| | Initial Block | US 1 | US 2 | US 3 | US 4 |
|---|---|---|---|---|---|
| TTX | 8.3 ± 4.7 | 0.7 ± 0.2 | 0.2 ± 0.2 | 0 ± 0 | — |
| TTX + DMED | 32.9 ± 4.6 | 1.9 ± 1.1 | 0.9 ± 0.3 | 0.5 ± 0.2 | *0 ± 0 |

*Peak thermal latency between 4 s and 7 s after ultrasound event.
Data are means ± SD, N = 4. Ultrasound (3 W/cm$^2$, 1 MHz, 10 min) was applied after the previous nerve block returned to 4 s.

Ultrasound application (3 W/cm$^2$, 1 MHz, 10 min) after the thermal latency returned below 4 s resulted in a return of nerve block for 0.7±0.2 h. FIG. 26B shows a second application of ultrasound, applied after the thermal latency returned to 4 s again, caused a return of nerve block with a duration of 0.2±0.2 h. No nerve block was observed after a third ultrasound application. There was no animal mortality or increase in contralateral latency on this group, indicating no observable systemic toxicity. (Contralateral latency was baseline, below 4 s for all time points) However, 50% of animals injected with Lipo-TTX (3 of 6) died within 10 h after injection, possibly a reflection of the more rapid TTX release in this group as shown in FIG. 25B. In the 3 animals that survived as shown in FIG. 26C, Lipo-TTX induced an initial nerve block of 17.2±11.3 h, but insonation after the thermal latency returned below 4 s did not induce nerve block as shown in FIG. 26D, demonstrating that PPIX was necessary for the increase in hind-paw thermal latency upon ultrasound irradiation.

To further enhance the number and duration of ultrasound-triggerable nerve blocks, dexmedetomidine-loaded liposomes (Lipo-DMED) were co-administered with Lipo-PPIX-TTX at a 1:2 (Lipo-DMED:Lipo-PPIX-TTX) volume ratio. DMED, an $\alpha_2$-adrenergic agonists, was shown to prolong the local anesthetic effects of TTX (McAlvin J B, et al., *Invest. Ophthalmol. Vis. Sci.*, 56:3820-3826 (2015)). FIG. 27A and Table 6 show Lipo-PPIX-TTX+Lipo-DMED caused an initial nerve block of 32.9±4.6 h, a longer duration than Lipo-PPIX-TTX.

FIG. 27B shows repeated insonation (3 W/cm$^2$, 1 MHz, 10 min) after the return to 4 s latency triggered three separate consecutive nerve blocks with durations of 1.9±1.1 h, 0.9±0.3 h, and 0.5±0.2 h respectively. The fourth ultrasound application induced an increase in hind-paw thermal latency to a mean of 5.9±0.6 s. These results demonstrate that the co-administration of Lipo-DMED and Lipo-PPIX-TTX enhanced the repeatability and duration of nerve block compared to Lipo-PPIX-TTX alone.

The intensity and duration of the ultrasound-triggered nerve blocks could be controlled by varying the duration of insonation applied after the initial nerve block from the administration of Lipo-DMED+Lipo-PPIX-TTX wore off. FIG. 27C shows insonation pulses of 10-min, 5-min and 2-min induced nerve blocks with a mean duration of 1.8±1.2 h, 0.5±0.2 h and 0.2±0.2 h respectively. Table 7 shows up to five separate consecutive ultrasound-triggerable nerve blocks were achieved by 5-min ultrasound irradiations.

TABLE 7

Duration of nerve block from co-administration of Lipo-PPIX-TTX + Lipo-DMED and after subsequent application of ultrasound with varying durations.

| | Initial Block (h) | US 1 (h) | US 2 (h) | US 3 (h) | US 4 (h) | US 5 (h) | US 6 (h) |
|---|---|---|---|---|---|---|---|
| 2 min | 33.4 ± 3.7 | 0.2 ± 0.2 | *0 ± 0 | — | — | — | — |
| 5 min | 27.0 ± 2.4 | 0.5 ± 0.2 | 0.4 ± 0.1 | 0.4 ± 0.1 | 0.3 ± 0.1 | 0.3 ± 0.1 | *0 ± 0 |
| 10 min | 32.9 ± 4.6 | 1.9 ± 1.1 | 0.9 ± 0.3 | 0.5 ± 0.2 | *0 ± 0 | — | — |

*Peak thermal latency between 4 s and 7 s after ultrasound event. Data are means ± SD, N = 4. Ultrasound (3 W/cm$^2$, 1 MHz, 10 min) was applied after the previous nerve block returned to 4 s.

The mean peak thermal latency was 12 s for both 10-min and 5-min insonation and 7.3±1.4 s for the 2-min insonation. The survival rate for all rats injected with Lipo-PPIX-TTX (with and without Lipo-DMED) was 100% (20 animals in total) and no increase in contralateral latency was observed, indicating that no observable systemic toxicity assessed via contralateral latency was shown in rats injected with Lipo-PPIX-TTX (with and without Lipo-DMED).

FIG. 27D shows the duration of the ultrasound-triggered nerve block had a sigmoidal relationship to the duration of ultrasound application. The relationship indicated nerve block could be effectively controlled by simply adjusting the duration of ultrasound application.

In Vitro Cytotoxicity and In Vivo Tissue Reaction

The cytotoxicity of the formulation's diffusible components was tested the in vitro in cell types relevant to the in vivo milieu: C2C12 mouse myotubes (muscle toxicity) and PC12 rat adrenal gland pheochromocytoma cells (neurotoxicity) upon exposure to ultrasound-treated liposomes. FIGS. 28A and 28B show no significant difference in cell viability was found in Lipo-DMED or Lipo-PPIX-TTX when compared with untreated cells, with or without ultrasound.

In all animals that underwent neurobehavioral testing, the sciatic nerve and surrounding tissues were collected 4 days after the last ultrasound application. Animals administered with PPIX-loaded liposomes had reddish-brown liposome deposits surrounding the sciatic nerve, demonstrating accurate liposome injection at the target site. Collected tissues were processed into hematoxylin & eosin-stained slides. All animals injected with liposomes showed mild inflammation at the injection site consistent with previous reports of perineural microparticle injection (Kohane D S, J Biomed. Mater. Res., 59:450-459 (2002); Anderson J M, Eur. J. Pharm. Biophar., 40:1-8 (1994)), but minimal inflammation was seen in the adjacent muscle. All slides were scored for inflammation (0-4) and myotoxicity (0-6). Table 8 shows all groups had median inflammation scores of 1.

TABLE 8

Tissue reaction 4 days after injections.

| | Inflammation Score | Myotoxicity Score |
|---|---|---|
| Lipo-PPIX-TTX | 1 (1, 1) | 0 (0, 0) |
| Lipo-PPIX-TTX + US | 1 (1, 1) | 0 (0, 0) |
| Lipo-TTX + US | 1 (0.5, 1) | 0 (0, 0.5) |
| Lipo-PPIX-TTX + Lipo-DMED + US | 1 (0.8, 1) | 0 (0, 0) |

Data are medians (quartiles). N = 4 for all groups except for Lipo-TTX (data are from 3 of 6 rats that survived).

No significant myotoxicity was observed in animals injected with liposomes, with or without ultrasound. The median myotoxicity score was 0 in all groups. The co-administration of Lipo-DMED and Lipo-PPIX-TTX did not show significant differences in myotoxicity from Lipo-PPIX-TTX administration alone.

Sciatic nerves were stained with toluidine blue and sectioned. No significant sciatic nerve neurotoxicity was observed from animals injected with Lipo-PPIX-TTX with and without the co-administration of Lipo-DMED upon application of ultrasound.

Ultrasound-Guided Injection and Sonography of Liposomes

Ultrasound-guidance has become a standard of practice for peripheral nerve blockade (Marhofer P, et al., British Journal of Anaesthesia, 104:673-683 (2010)). It would be advantageous if ultrasound could be used both for procedural imaging and subsequent triggering. Lipo-PPIX could be visualized by ultrasound. PPIX-loaded liposomes (Lipo-PPIX) were placed between two layers of ultrasonic gel in vitro and were imaged with high frequency ultrasound (40 MHz, $I_{SPTA}$<0.08 W/cm$^2$). Ultrasonography showed the liposome layer showed dense granular patterns of brightness whereas the same volume of water did not.

In anesthetized animals, the sciatic nerve was identified under sonography at a tissue depth of approximately 7 mm. A 23G needle was then advanced beside the sciatic nerve, and Lipo-PPIX was injected. A bright liposome deposit was observed on the sonogram after injection, showing successful injection and imaging of liposomes at the target site.

A single ultrasound device as described herein can be used by the clinician for pain treatments: using a diagnostic ultrasound setup (higher frequency, lower power) during injection, followed by formulation imaging, and using a therapeutic setup (lower frequency, higher power) to trigger further anesthetic events post-injection, easing the clinical translation of such strategies. The drug delivery system studied may combine the therapeutics and diagnostics aspect of ultrasound by using precise injections and imaging via its diagnostic settings and triggering nerve block upon therapeutic ultrasound exposure.

Discussion

The co-administration of Lipo-DMED with Lipo-PPIX-TTX enhanced the nerve block duration by 3-fold upon ultrasound administration (3 W/cm$^2$, 1 MHz, 10 min) when compared with the Lipo-PPIX-TTX only group. The enhancement in nerve block duration was accompanied by an increase in the number of effective ultrasound-triggerable nerve blocks, indicating greater possible therapeutic effects for a given ultrasound dosage upon co-administration. One potential mechanism was through the DMED inhibition of hyperpolarization-activated cation current (Brummett C M, et al, Anesthesiology, 115:836-843 (2011); Kosugi T, et al., Br. J. Pharmacol., 160:1662-1676 (2010)). Another contributing factor was the $\alpha_2$-adrenergic receptor mediated vasoconstriction at the local site, which inhibited redistribution of the local anesthetic to systemic circulation, thereby maintaining a high local concentration at the target tissue. Upon ultrasound application of animals co-injected with Lipo-PPIX-TTX and Lipo-DMED, the trapping of TTX at the local site by DMED and the blockade of hyperpolarization-activated cation current may have enhanced the therapeutic effectiveness of Lipo-PPIX-TTX.

The repeatability and adjustability of the triggered nerve blocks indicated that after a single injection of the formulation, pain relief could be adjusted within 48 h after injection in a personalized pattern according to the patient's changing condition using non-invasive ultrasound.

As the ultrasound parameters used in this Example were currently used in the clinics for therapeutic ultrasound, and therefore was not toxic to tissues. From histology results, the ROS that was produced from sonosensitization did not induce myotoxicity. The main ROS that are involved in sonosensitization are hydroxyl radicals and singlet oxygen, the former has a half-life of $10^{-9}$ S and diffusion distance of 0.06 nm (Forkink M, et al., Biochim. Biophys. Acta, Bioenerg., 1797:1034-1044 (2010); Roots R, et al., Radiat. Res., 64:306-320 (1975); Pryor W A, et al., Annu. Rev. Physiol., 48:657-667 (1986)), the latter has a half-life of $10^{-6}$ S and diffusion distance of 268 nm (Skovsen E, et al., J. Phys. Chem. B., 109:8570-8573 (2005)). These distances were small compared with the length scale of tissue, indicating that their effects may not be significant, as supported by the results of this study.

Example 10: Applying Ultrasound and Microbubbles with Local Anesthetics Enhanced Drug Flux and Nerve Block Effectiveness, Prolongation and Consistency Methods Microbubble Preparation.

As described in Kheirolomoom A, et al., *J Control Release*, 118(3):275-84 (2007)), 1,2 Distearoyl-sn-glycero-3-phosphatidylcholine (DSPC) and 1,2 distearoyl-sn-glycero-3-phosphoethanolamine-N-[Methoxy (Polyethylene glycol)-2000] (DSPE-PEG2k; 90:10, molar ratio) were combined and dissolved in chloroform. Chloroform was then removed by evaporation under vacuum for 2 hours. The lipids were dissolved in a 100 mM Tris buffer (pH 7.4) with glycerol:propyleneglycol (80:10:10, volume ratio) to create a lipid concentration of 1 mM. The suspension was mixed well and sonicated with bath sonicator (20 kHz for 3 minutes), followed by sonication by probe sonicator (40 kHz, 16 seconds). Fluorobutane gas was then slowly injected into a glass vial for 20 seconds and the glass vial was immediately capped. Microbubbles were quantification and analyzed for size using coulter counter. Microbubbles were diluted with PBS to a concentration of $1 \times 10^7$/mL.

Sciatic Nerve Block Using TTX Assisted with Ultrasound and Microbubbles.

Young adult male Sprague-Dawley rats (350-420 g) were obtained from Charles River Laboratories (Wilmington, Mass.) and housed in groups of two per cage on a 7 a.m. to 7 p.m. light/dark cycle. All animals were cared for in accordance with protocols approved by the Animal Care and Use Committee at Boston Children's Hospital, as well as the Guide for the Care and use of Laboratory Animals of the US National Research Council. Rats were anesthetized using isoflurane in oxygen (3.5%) and then shaved to provide coupling surface for ultrasound application. Injections were performed on the left sciatic nerve as described previously in Kohane D S, et al., *Anesthesiology*, 89(5): 1199-208 (1998)). A 23-gauge needle was introduced posteromedial to the greater trochanter of the femur pointed in an anteromedial direction, 0.3 mL of the drug including TTX was injected upon contacting bone, depositing the drug over the sciatic nerve. All injections were performed by the same experimenter, who demonstrated >99% successful sciatic nerve blocks with 0.1 ml of 0.5% bupivacaine, to ensure any difference observed in subsequent assessments reflect actual differences in the effects of drug treatments. After the drug was deposited on the sciatic nerve by injection, the ultrasound transducer was held posteromedial to the greater trochanter of the femur pointed in an antero-medial direction for 5 minutes. A manually controlled ultrasonic pulser-receiver, model 5072PR (Olympus Corporation), with a 1 MHz 1.125 inch diameter transducer was used with the electrical power set to 0.02 W/cm². Ultrasound gel was used for coupling. The pulser-receiver remained connected to an oscilloscope to provide visual conformation of the electrical signal throughout the application of the ultrasound.

Rats were administered with one of the following treatments:

(1) co-injection of TTX in 300 μL microbubbles followed by 5 minutes of ultrasound at 1 MHz, denoted as TTX+US+MB, where TTX was injected at 25 μM (N=7), 30 μM (N=9), or 35 μM (N=7);

(2) injection of TTX in 300 μL PBS followed by 5 minutes of ultrasound at 1 MHz, denoted as TTX+US, where TTX was injected at 25 μM (N=4), 30 μM (N=9), or 35 μM (N=8);

(3) co-injection of TTX in 300 μL microbubbles without ultrasound treatment, denoted as TTX+MB, where TTX was injected at 25 μM (N=8), 30 μM (N=8), or 35 μM (N=6); and (4) injection of TTX alone in 300 μL PBS, denoted as TTX, at 25 μM (N=4), 30 μM (N=8), or 35 μM (N=7).

TTX stock solutions were made by dissolving 1 mg (>98% purity, Abcam, Cambridge, Mass.) in 10 ml of 20 nM citrate solution (pH 4.5). A TTX dose response curve (15-35 μM, n=4 per group) was generated with each new stock solution, prior to any experiments. Each drug solution and microbubble solution was prepared on the same day of injections.

The effect of ultrasound on duration of nerve block produced by bupivacaine was evaluated by injecting rats with 0.5% bupivacaine, diluted in PBS (diluted in 300 μL of PBS, or 300 μl of microbubbles) with and without 5 minutes of ultrasound at 1 MHz (n=4 per group).

Assessment of Sciatic Nerve Blockade.

In all experiments, the experimenter was blinded as to what treatment any given rat had received. Presence and extent of nerve blockade was investigated as described in Padera R F, et al., *Muscle Nerve*, 34(6):747-753 (2006), Kohane D S, et al., *Regional Anesthesia and Pain Medicine*, 26(3):239-245 (2001), Kohane D S, et al., *Anesthesiology*, 89(5):1199-208 (1998), and Masters D B, et al., *Anesthesiology*, 79:340-346 (1993)). Animals that did not survive the injection were excluded from percentage of animals blocked, duration of sensory/motor block analysis, and assessment of contralateral block, but were included in the estimation of systemic toxicity and death:

(1) Calculate Success of Nerve Blockade.

This was performed at the sole of the foot, which was a distal site in dermatomes innervated by the sciatic nerve. The uninfected leg served as the control.

(2) Duration of Thermal Nociception Blockade.

Hind paws were exposed in sequence (left then right) to a 56° C. hot plate (Model 39D Hot Plate Analgesia Meter, IITC Inc., Woodland Hills, Calif.). The time until paw withdrawal was measured with a stopwatch. This test was repeated three times and the average time in seconds was calculated. If the animal did not remove its paw from the hot plate within 12 seconds, it was removed by the experimenter to avoid injury to the animal or the development of hyperalgesia. Testing was conducted every 30 minutes until the nerve blockade resolved. Latencies longer than 7 seconds, which was the midpoint between baseline thermal latency 2 seconds and maximum latency 12 seconds, were considered to represent effective blocks. The duration of thermal nociceptive block was calculated as the time for thermal latency to return to a value of 7 seconds.

(3) Duration of Motor Nerve Blockade.

Motor nerve block was assessed by a weight-bearing test to determine the motor strength of the rat's hindpaw, as described previously (Thalhammer J G, et al., *Anesthesiology*, 82(4): 1013-1025 (1995), Kohane D S, et al., *Anesthesiology*, 89(1):119-131 (1998)). In brief, the rat was positioned with one hindpaw on a digital balance and was allowed to bear its own weight. The maximum weight that the rat could bear without the ankle touching the balance was recorded, and motor block was considered achieved when the motor strength was less than half-maximal.

(4) Systemic Symptoms Assessed in Contralateral Nerve Blockade and Respiratory Distress.

Assessment of Local Side Effects.

Animals were euthanized with carbon dioxide, and the sciatic nerves and adjacent tissues were harvested for histology. Tissues were fixed in 10% formalin, embedded in paraffin, sectioned, and stained with hematoxylin and eosin using standard techniques. Tissues were all harvested at 4 days and 14 days after nerve injections. Muscle samples were scored for inflammation (0-4 points) and myotoxicity (0-6 points) as described previously Padera R F, et al., *Muscle Nerve*, 34(6):747-753 (2006).

Results

As shown in FIG. 29, rats injected with TTX followed by ultrasound treatment (TTX+US) and rats injected with TTX dissolved in a solution containing microbubbles without the application of ultrasound (TTX+MB) had blockade success percentages that were not statistically different from that of rats injected with TTX alone. In contrast, animals receiving a co-injection of TTX and microbubbles followed by ultrasound treatment (TTX+US+MB) had a significant increase in the percentage of nerve blockade success compared to all three control groups at each concentration of TTX tested: at 25 µM of TTX, 86% (TTX+US+MB) compared to 0-25% (TTX+US, TTX+MB, or TTX); at 30 µM of TTX, 100% (TTX+US+MB) compared to 40-62% (TTX+US, TTX+MB, or TTX); and at 35 µM, 100% (TTX+US+MB) compared to 57-75% (TTX+US, TTX+MB, or TTX).

The treatment combination of TTX with microbubbles followed by application of ultrasound (TTX+US+MB) resulted in a significant prolongation of both nociceptive block at all concentrations of 25 µM, 30 µM, and 35 µM of TTX (FIG. 30) and motor nerve block at 30 µM and 35 µM of TTX (FIG. 31A and FIG. 31B). In control groups where animals were treated with TTX alone, TTX+US, or TTX+MB, the duration of nociceptive and motor blockade increased with increasing concentrations of TTX, but the durations of block among these groups were not statistically different. With respect to thermal nociception blockade, at 35 µM of TTX, rats treated with TTX+US+MB had a greater than 3-fold increase in duration of nociceptive blockade compared to control groups (TTX+US, TTX+MB, and TTX), as the median duration of nerve block in TTX+US+MB was 157 minutes with $25^{th}$ and $75^{th}$ percentiles of 133 minutes and 190 minutes, respectively. The control groups had median durations of nerve block between 37 minutes and 57 minutes. With respect to motor strength, at 35 µM of TTX, rats treated with TTX+US+MB had a median duration of motor nerve block that lasted 134 minutes ($25^{th}$ and $75^{th}$ percentiles of 132 and 157, respectively) compared to a median time of 0 minutes (interquartile range 0-82 minutes) of animals treated with TTX only, and 36 minutes (interquartile range 0-80 minutes) of animals treated with TTX+MB. Animals injected with 35 µM of TTX followed by ultrasound treatment (TTX+US) had a median duration of motor nerve block (113 minutes) notably longer than other control groups, albeit with large interquartile range $25^{th}$ to $75^{th}$ of 0-120 minutes. At other concentrations of TTX tested, the effect of ultrasound treatment in the absence of microbubbles was not apparent, either, which could be due to the sample size.

Also as shown in FIGS. 30, 31A, and 31B, the standard deviations of the duration of thermal or motor block were large relative to the median values for each control group (TTX only, TTX+MB, or TTX+US) at all concentrations of TTX tested, showing the great extent of variability in duration of thermal or motor block. Compared with the control groups, the standard deviations of duration thermal and motor block in animals treated with both microbubbles and ultrasound (TTX+US+MB) were smaller, demonstrating the increased consistency in nerve block using anesthetics in combination with microbubbles and ultrasound.

Rats treated with TTX+US+MB also had a greater frequency of contralateral nerve block than those treated without ultrasound or microbubbles. As shown in Table 9, rats treated with TTX+US+MB had 50%, 77%, and 100% contralateral nerve block compared to 0, 20%, or 25% in the groups treated with TTX alone at 25 µM, 30 µM, or 35 µM of TTX, respectively.

TABLE 9

Frequency of successful nerve block with contralateral block.

| TTX (µM) | TTX | TTX + Ultrasound | TTX + MB | TTX + Ultrasound + MB |
|---|---|---|---|---|
| 15 | — | N/A | N/A | N/A |
| 25 | 0/1 | N/A | 0/1 | 3/6 |
| 30 | 1/5 | 1/4 | 0/3 | 7/9 |
| 35 | 1/4 | 5/5 | 4/5 | 7/7 |

Treating animals with TTX, ultrasound and microbubbles also resulted in an increased rate of systemic distress when higher concentrations of TTX were injected. At 30 µM, 72% of animals treated with TTX+US+MB developed signs of systemic distress; including respiratory distress compared to 0-12% in control groups (Table 10). Any animal with signs of respiratory distress in treatment or control groups was treated with oxygen therapy for 30 minutes or until resolution of symptoms. The time to symptom resolution did not vary among treatment and control groups.

TABLE 10

Frequency of systemic distress.

| TTX (µM) | TTX | TTX + Ultrasound | TTX + MB | TTX + Ultrasound + MB |
|---|---|---|---|---|
| 15 | — | 0/4 | 0/4 | 0/4 |
| 25 | 0/4 | 0/4 | 0/8 | 0/7 |
| 30 | 1/8 | 0/9 | 0/8 | 8/11 |
| 35 | 2 8 | 3/8 | 6/8 | 7/8 |

At the highest concentration of TTX tested, 35 µM, there was a modest increase in systemic distress when animals were treated with either TTX+US or TTX+MB compared to animals treated with TTX only. 100% of animals developed contralateral block and 37.5% developed systemic distress in the TTX+US group, while 80% developed contralateral nerve block and 75% developed systemic distress in the TTX+MB group. This is in comparison to 25% contralateral block and 25% systemic distress in animals treated with TTX alone (Tables 9 and 10).

Despite an increase in systemic side effects with ultrasound and microbubble combination therapy, there was only a slight increase in mortality. As shown in Table 11, three of the 30 (10%) animals treated with TTX+US+MB at increasing concentrations of TTX died, compared with 5% with TTX alone, 0% with TTX+MB, and 7% with TTX+US.

TABLE 11

Frequency of mortality.

| TTX (µM) | TTX | TTX + Ultrasound | TTX + MB | TTX + Ultrasound + MB |
|---|---|---|---|---|
| 15 | — | 0/4 | 0/4 | 0/4 |
| 25 | 0/4 | 0/4 | 0/8 | 0/7 |
| 30 | 0/8 | 0/9 | 0/8 | 2/11 |
| 35 | 1/8 | 0/8 | 2/8 | 7/8 |

Local side effects were determined by microscopic evaluation of the injected nerve and surrounding muscle at 4 and 14 days post-injection, for optimal analysis on inflammation response and mytotoxicity. As expected, animals treated with TTX alone developed minimal levels of inflammation (score of 1 out of 8) and no myotoxicity (score 0 out of 4) at 4 days (FIG. 32A and FIG. 32B). Coinjecting TTX with microbubbles or treating with ultrasound after the injection of TTX resulted in scores similar to TTX alone. When animals were coinjected with increasing concentrations of TTX plus microbubbles and then treated with ultrasound, the average score of inflammation at 4 days appeared to be greater than the average score of control groups. There was no myotoxicity detected at 4 days in any of the groups tested (FIG. 32B).

The effects of contralateral block and respiratory distress were likely secondary to greater drug flux across biological barriers surrounding the peripheral nerve, which was supported by the fact that lower concentrations of TTX achieved consistent nerve block of prolonged duration compared to control groups. Therefore, ultrasound-microbubble mediated anesthetic dosing allows lower concentrations of anesthetics (e.g., TTX) to be required for anesthesia and to avoid systemic toxicity. Systemic toxicity observed may be reduced when larger animal models are used, as toxicity is in direct proportion to the mass and volume of distribution of the recipient (Kohane D S, et al., *Anesthesiology*, 89(5): 1199-208 (1998)). In model systems with a greater volume of distribution, for example human recipients, it is believed they may have higher tolerance to ultrasound-assisted drug delivery when larger doses of anesthetics are administered.

Although ultrasound is capable of inducing both thermal and non thermal forces such as acoustic cavitation, radiation, and convection, the electrical power used in this experiment was 0.02 W/cm$^2$, which was likely below the threshold of spontaneous cavitation. Since poorer consistency and prolongation in nerve block was observed in animals treated with ultrasound alone without the addition of microbubbles, the enhanced consistency and prolongation of nerve blockade in TTX+US+MB treatment may be mediated by cavitation, or at least in part by the interaction between acoustic waves and microbubbles.

Low intensity ultrasound (0.1-100 mW/cm$^2$ or 0.0001-0.1 W/cm$^2$) is often used for diagnostic imaging and is also likely below spontaneous cavitation threshold. (Dubinsky T J, et al., *Am J Roentgenology*, 190(1): 191-199 (2008)). It is believed conventional clinical imaging ultrasounds may also be used for drug delivery purposes with the addition of exogenous microbubbles.

We claim:

1. A pharmaceutical composition comprising
   triggerable liposomes, particles or microbubbles encapsulating at least one site 1 sodium channel blocker,
   wherein the site 1 sodium channel blocker is repeatably released upon exposure to a triggering agent in an amount effective to produce anesthesia,
   wherein the triggerable liposomes, particles or microbubbles comprise one or more triggerable elements selected from the group consisting of gold nanorods, gold nanoshells, gold nanostars, gold nanocages, photosensitizers, and sonosensitizers.

2. The pharmaceutical composition of claim 1, wherein the triggering agent is selected from the group consisting of near-infrared irradiation, ultraviolet and visible light, ultrasound and magnetic field.

3. The pharmaceutical composition of claim 1, comprising liposomes or particles containing one or more triggerable elements.

4. The pharmaceutical composition of claim 1, comprising liposomes, wherein the triggerable elements are in an amount effective to disrupt the lipid membrane bilayer to release the encapsulated content in response to any of the triggering agents.

5. The pharmaceutical composition of claim 1, further comprising one or more agents selected from the group consisting of alpha-2-adrenergic agonists, local anesthetics, and vasoconstrictors encapsulated in liposomes or particles.

6. The pharmaceutical composition of claim 4, wherein the triggerable element is a gold nanoparticle selected from the group consisting of gold nanorods, gold nanoshells, gold nanostars and gold nanocages.

7. The pharmaceutical composition of claim 6, wherein the gold nanoparticle is gold nanorods.

8. The pharmaceutical composition of claim 7, wherein the gold nanorods have an aspect ratio ranging from 1.5 to 10 for which the surface plasmon absorption maxima are between 600 and 1300 nm.

9. The pharmaceutical composition of claim 7, wherein the gold nanorods have a concentration of between 0.001 and 1 wt %.

10. The pharmaceutical composition of claim 3, wherein the triggerable element is a photosensitizer.

11. The pharmaceutical composition of claim 10, wherein the photosensitizer comprises 1,4,8,11,15,18,22,25-octabutoxyphthalocyaninato-palladium.

12. The pharmaceutical composition of claim 11 comprising liposomes formed of unsaturated lipids selected from the group consisting of L-α-phosphatidylcholine and 1,2-dilinoleoyl-sn-glycerol-3-phosphocholine in combination with at least one of a lipid selected from the group consisting of 1,2-distearoyl-sn-glycero-3-phosphocholine, 1,2-dioctadecanoyl-sn-glycero-3-phospho-(1'-rac-glycerol) and cholesterol.

13. The pharmaceutical composition of claim 3, wherein the triggerable element comprises a sonosensitizer.

14. The pharmaceutical composition of claim 13, wherein the sonosensitizer comprises protoporphyrin IX.

15. The pharmaceutical composition of claim 1, comprising liposomes having a phase transition temperature that is between 33 and 43° C.

16. The pharmaceutical composition of claim 15, wherein the liposome comprises 1,2-Dipalmitoyl-sn-glycero-3-phosphocholine (DPPC), 1,2 dipalmitoyl-sn-glycero-3-phospho-(1'-rac-glycerol) (DPPG), cholesterol, and thiolated PEG-DSPE (HS-PEG-DSPE).

17. The pharmaceutical composition of claim 16, wherein the total lipid composition comprises a molar ratio of 1,2-Dipalmitoyl-sn-glycero-3-phosphocholine (DPPC) to 1,2 dipalmitoyl-sn-glycero-3-phospho-(1'-rac-glycerol) (DPPG) to cholesterol to thiolated PEG-DSPE (HS-PEG-DSPE) of about 6:2:3:0.2.

18. The pharmaceutical composition of claim 1, wherein the site 1 sodium channel blocker is selected from the group consisting of tetrodotoxin, saxitoxin, decarbamoyl saxitoxin, neosaxitoxin, gonyautoxins, and conotoxins.

19. The pharmaceutical composition of claim 18, wherein the site 1 sodium channel blocker is tetrodotoxin.

20. The pharmaceutical composition of claim 5 comprising an alpha-2-adrenergic agonist selected from the group consisting of xylazine, flutonidine, moxonidine, tramazoline, tolonidine, piclonidine, tiamenidine, clonidine and dexmedetomidine.

21. The pharmaceutical composition of claim 20, wherein the alpha-2-adrenergic agonist is dexmedetomidine.

22. The pharmaceutical composition of claim 1, further comprising a pharmaceutically acceptable carrier.

\* \* \* \* \*